United States Patent
Hergenrother

(10) Patent No.: US 10,525,056 B2
(45) Date of Patent: Jan. 7, 2020

(54) PROCASPASE-ACTIVATING COMPOUNDS AND METHODS

(71) Applicant: The Board of Trustees of the University of Illinois, Urbana, IL (US)

(72) Inventor: Paul J. Hergenrother, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 16/037,812

(22) Filed: Jul. 17, 2018

(65) Prior Publication Data

US 2018/0360824 A1 Dec. 20, 2018

Related U.S. Application Data

(60) Continuation of application No. 14/581,470, filed on Dec. 23, 2014, now Pat. No. 10,022,371, which is a division of application No. 13/652,164, filed on Oct. 15, 2012, now Pat. No. 8,916,705.

(60) Provisional application No. 61/547,135, filed on Oct. 14, 2011.

(51) Int. Cl.
*A61K 31/495* (2006.01)
*C07D 295/15* (2006.01)

(52) U.S. Cl.
CPC .......... *A61K 31/495* (2013.01); *C07D 295/15* (2013.01)

(58) Field of Classification Search
CPC .................................... A61K 31/495
USPC ...................................... 544/400
See application file for complete search history.

(56) References Cited

U.S. PATENT DOCUMENTS

| | | | |
|---|---|---|---|
| 6,303,329 B1 | 10/2001 | Heinrikson et al. | |
| 6,403,765 B1 | 6/2002 | Alnemri | |
| 6,534,267 B1 | 3/2003 | Wang et al. | |
| 6,762,045 B2 | 7/2004 | Krebs et al. | |
| 6,878,743 B2 | 4/2005 | Choong et al. | |
| 2004/0077542 A1 | 4/2004 | Wang et al. | |
| 2004/0180828 A1 | 9/2004 | Shi | |
| 2005/0197511 A1 | 9/2005 | Hergenrother et al. | |
| 2007/0049602 A1* | 3/2007 | Hergenrother ....... | A61K 31/495 514/252.12 |
| 2011/0257398 A1 | 10/2011 | Hergenrother et al. | |
| 2012/0040995 A1 | 2/2012 | Hergenrother et al. | |

FOREIGN PATENT DOCUMENTS

| | | |
|---|---|---|
| WO | 2006128173 A2 | 11/2006 |
| WO | 2007008529 A3 | 8/2007 |
| WO | 2008134474 A2 | 11/2008 |

OTHER PUBLICATIONS

Lippard, S.J., "The Art of Chemistry: Chemical Synthesis," Nature, 415:487, Apr. 2002.
Peterson et al., "Procaspase-3 Activation as an Anti-Cancer Strategy: Structure-Activity Relationship of Procaspase-Activating Compound 1 (PAC-1) and its Cellular Co-Localization with Caspase-3," J Med Chem., 52(18):5721-5731, Sep. 2009.
Vogelstein et al., "Cancer Genes and the Pathways They Control," Nat Med., 10(8):789-799, Aug. 2004.

* cited by examiner

*Primary Examiner* — Savitha M Rao
*Assistant Examiner* — Taina D Matos Negron
(74) *Attorney, Agent, or Firm* — Haukaas Fortius PLLC; Michael H. Haukaas

(57) ABSTRACT

The invention provides compounds and compositions useful for the modulation of certain enzymes. The compounds and compositions can induce of cell death, particularly cancer cell death. The invention also provides methods for the synthesis and use of the compounds and compositions, including the use of compounds and compositions in therapy for the treatment of cancer and selective induction of apoptosis in cells.

16 Claims, 5 Drawing Sheets

PROCASPASE-ACTIVATING COMPOUNDS AND METHODS

RELATED APPLICATIONS

This application is Continuation of U.S. patent application Ser. No. 14/581,470, filed Dec. 23, 2014, issued as U.S. Pat. No. 10,022,371, which is a Divisional of U.S. patent application Ser. No. 13/652,164, filed Oct. 15, 2012, issued as U.S. Pat. No. 8,916,705, which application claims priority under 35 U.S.C. § 119(e) to U.S. Provisional Patent Application No. 61/547,135, filed Oct. 14, 2011, which applications are incorporated herein by reference in their entirety.

GOVERNMENT SUPPORT

This invention was made with government support under R01-CA120439 awarded by the National Institutes of Health. The United States Government has certain rights in the invention.

BACKGROUND OF THE INVENTION

Apoptosis is a process used by higher organisms to maintain homeostasis by removing cells that are in excess, damaged, or potentially dangerous. Critical to apoptosis is the activation of caspase enzymes, a class of cysteine proteases that cleave cellular substrates after recognition sequences with C-terminal aspartate residues. There are two canonical apoptotic pathways, differing in that the apoptosis-initiating stimulus is intracellular (intrinsic pathway) or extracellular (extrinsic pathway). These pathways converge at the cleavage of procaspase-3 to form the active caspase-3, the key "executioner" caspase that catalyzes the hydrolysis of hundreds of protein substrates, leading to cell death.

One of the hallmarks of cancer is the ability of cancer cells to evade apoptosis, allowing for unchecked proliferation. As such, reactivation of apoptosis in cells with defective apoptotic pathways is a promising anticancer strategy. Compounds such as p53-MDM2 disruptors (Nutlins), Bcl-2 inhibitors (ABT-737), and inhibitors of XIAP (SM-164) all act directly on proteins in the apoptotic cascade, inducing apoptosis and leading to death of cancer cells.

Complementary to the strategies described above, the direct activation of procaspase-3 with a small molecule has potential for the personalized treatment of cancer. Procaspase-3 levels are elevated in certain cancers, including lymphomas, leukemias, melanomas, pancreatic cancer, liver cancers, lung cancers, breast cancers, and colon cancers. Due to the elevated levels of procaspase-3 in cancer cells, the requirement of caspase-3 activation for apoptosis, and the relative downstream location of procaspase-3 in the apoptotic cascade, induction of apoptosis by the direct activation of procaspase-3 is being actively explored as a personalized anticancer strategy. Accordingly, there is a need for new compounds that modulate procaspase-3 activity.

SUMMARY

Procaspase-Activating Compound 1 (PAC-1) is an ortho-hydroxy N-acyl hydrazone that enhances the enzymatic activity of procaspase-3 in vitro and induces apoptosis in cancer cells. An analogue of PAC-1, called S-PAC-1, was evaluated in a veterinary clinical trial in pet dogs with lymphoma and found to have considerable potential as an anticancer agent. With the goal of identifying more potent compounds in this promising class of experimental therapeutics, a combinatorial library based on PAC-1 was created, and the compounds were evaluated for their ability to induce death of cancer cells in culture. For library construction, 31 hydrazides were condensed in parallel with 27 aldehydes to create 837 PAC-1 analogues, with an average purity of 91%. The compounds were evaluated for their ability to induce apoptosis in cancer cells, and through this work, six compounds were discovered to be substantially more potent than PAC-1 and S-PAC-1. These six "hits" were further evaluated for their ability to relieve zinc-mediated inhibition of procaspase-3 in vitro. In general, the newly identified compounds are two- to four-fold more potent than PAC-1 and S-PAC-1 in cell culture, and thus can provide therapeutics for treatment of the many cancers that have elevated expression levels of procaspase-3.

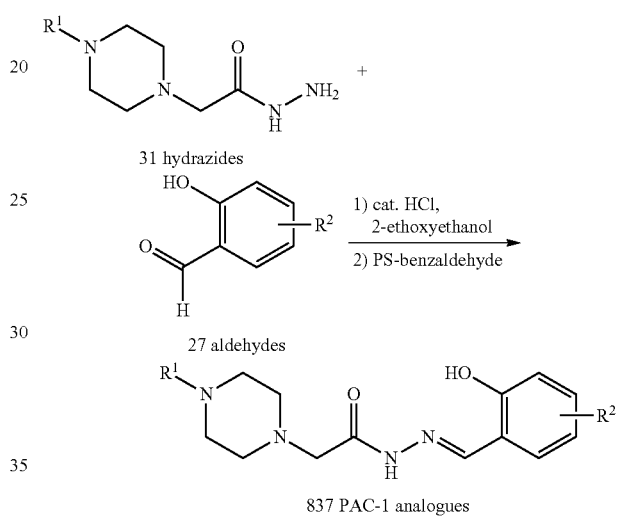

Compounds capable of activating enzymes that are often overexpressed in their inactive form in cancer cells have been discovered. The compounds can induce programmed cell death (apoptosis) in cancer cells, including those that have upregulated procaspase-3. Many cancers resist standard chemotherapy. The compounds described herein can take advantage of biological targets that may be upregulated in cancer cells and thus can be effective even in cells with defects in their apoptotic machinery. These compounds can also be successful in targeted cancer therapy by selectively killing cancer cells with comparably reduced adverse reactions to non-cancerous cells having lower levels of procaspase-3. These adverse reactions can include toxicity, particularly neurotoxicity.

Accordingly, the invention provides compounds of compound of Formula I:

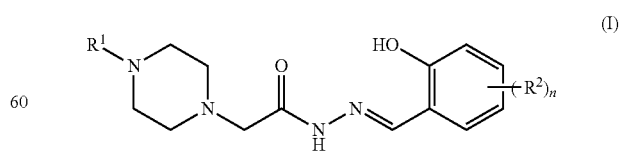

wherein $R^1$ is an optionally substituted phenyl or (aryl)methylene, or (aryl)methine wherein the methine carbon is optionally substituted with phenyl;

n is 1, 2, 3, or 4; and each $R^2$ is independently H, alkyl, alkoxy, hydroxy, halo, amino, alkylamino, dialkylamino, trifluoromethoxy, benzyl, benzyloxy, nitro, 2-propenyl, acetylene, N-alkyl-triazole, or N-benzyl-triazole; or two $R^2$ groups form an ortho-fused benzo group;

or a pharmaceutically acceptable salt or solvate thereof.

In some embodiments, n is 1 or 2. In other embodiments, n is 3 or 4. The variables $R^2$ can be ortho, meta, or para to the hydroxyl group of Formula I, or a combination thereof.

In some embodiments, $R^2$ is methyl, t-butyl, methoxy, hydroxy, fluoro, chloro, bromo, iodo, amino, ethylamino, diethylamino, trifluoromethoxy, benzyl, benzyloxy, nitro, 2-propenyl, acetylene, N-methyl-triazole, or N-benzyl-triazole. In various embodiments, n is 2 and two $R^2$ groups form an ortho-fused benzo group. In some embodiments, a substituent on an $R^1$ phenyl group can be a substituent $R^2$. In various embodiments, $R^2$ can be a substituent on an $R^1$ aryl group.

In some embodiments, n is 2 and each $R^2$ is t-butyl.

In some embodiments, n is 1 and $R^2$ is 2-propenyl.

In some embodiments, $R^1$ is a methoxy-benzyl; dimethoxy-benzyl; benzyloxy-benzyl; t-butyl-benzyl; naphthylmethylene; or ethyl-benzyl.

In certain specific embodiments, $R^1$ is 4-methoxy-benzyl; 2,5-dimethoxy-benzyl; 4-benzyloxy-benzyl; 4-t-butyl-benzyl; 2-naphthylmethylene; or 4-ethyl-benzyl.

In certain other specific embodiments, $R^1$ is:

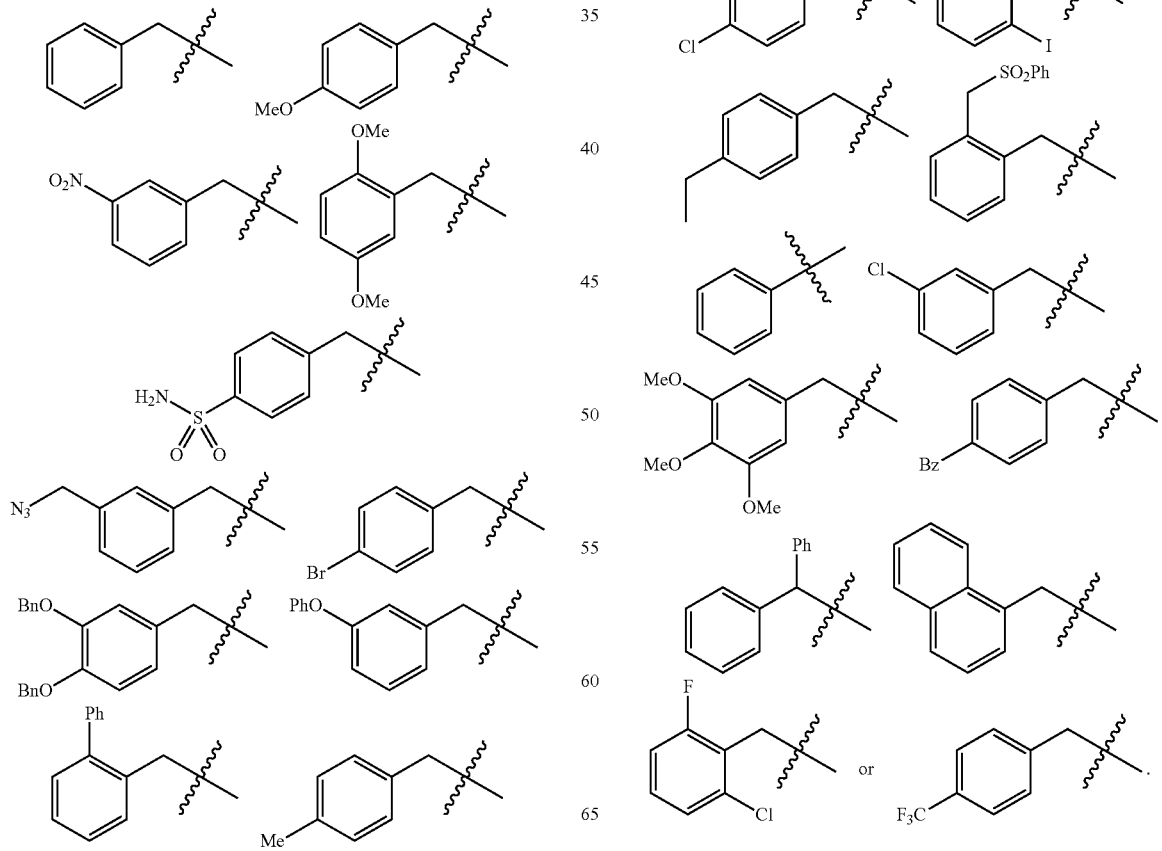

In various specific embodiments, the compound is one or more of:

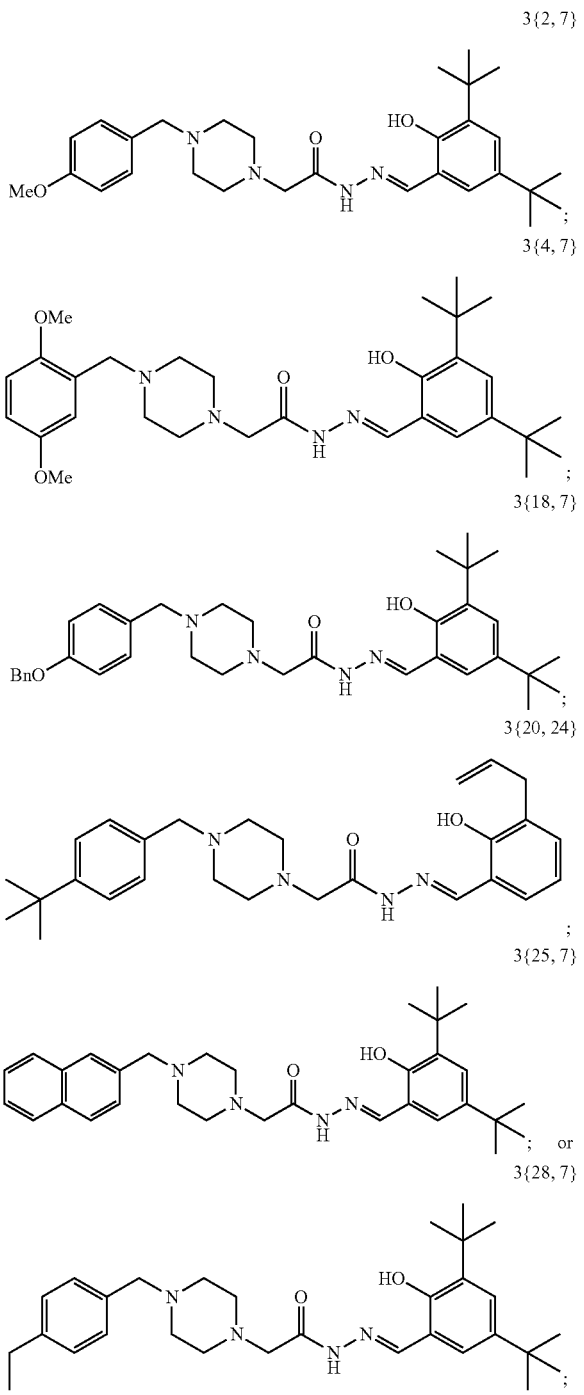

or a pharmaceutically acceptable salt or solvate thereof.

The invention also provides a pharmaceutical composition comprising a compound described herein and a pharmaceutically acceptable diluent, excipient, or carrier. In some embodiments, the compound induces death of cancer cells in culture.

The invention further provides a method of treating a cancer cell comprising (a) identifying a susceptibility to treatment of a cancer cell with a procaspase activator compound; and (b) exposing a cancer cell to an effective amount of the procaspase activator compound; wherein the procaspase activator compound is a compound described herein.

The invention additionally provides a method of inducing apoptosis in a cell comprising administering to a cell an effective amount of a compound described herein.

In some embodiments, the invention provides compounds and methods involving effective concentrations, such as about 10 nM to about 100 µM of the compound or formula. In some embodiments, the effective concentrations are from about 200 nM to about 5 µM. In another embodiment, the effective concentration is a value such as a 50% activity concentration in a direct procaspase activation assay, in a cell apoptosis induction assay, or in an animal clinical therapeutic assessment. In another embodiment, such value is less than about 200 µM. In various embodiments, the value is less than about 10 µM.

The invention therefore provides compounds, compositions, and methods of therapeutic treatment. In some embodiments, the inventions are applicable in the context of a variety of cancer diseases and cancer cell types such as breast, lymphoma, adrenal, renal, melanoma, leukemia, neuroblastoma, lung, brain, among others.

The invention provides the novel compounds described herein and the compounds of the Formulas described herein, intermediates for the synthesis of such compounds, as well as methods of preparing the compounds. The invention also provides compounds that are useful as intermediates for the synthesis of other useful compounds.

The also invention provides for the use of the compositions described herein for use in medical therapy. The medical therapy can be treating cancer, for example, lymphomas, leukemias, melanomas, pancreatic cancer, liver cancers, lung cancers, breast cancers, and colon cancers. The invention also provides for the use of a composition as described herein for the manufacture of a medicament to treat a disease in a mammal, for example, cancer in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
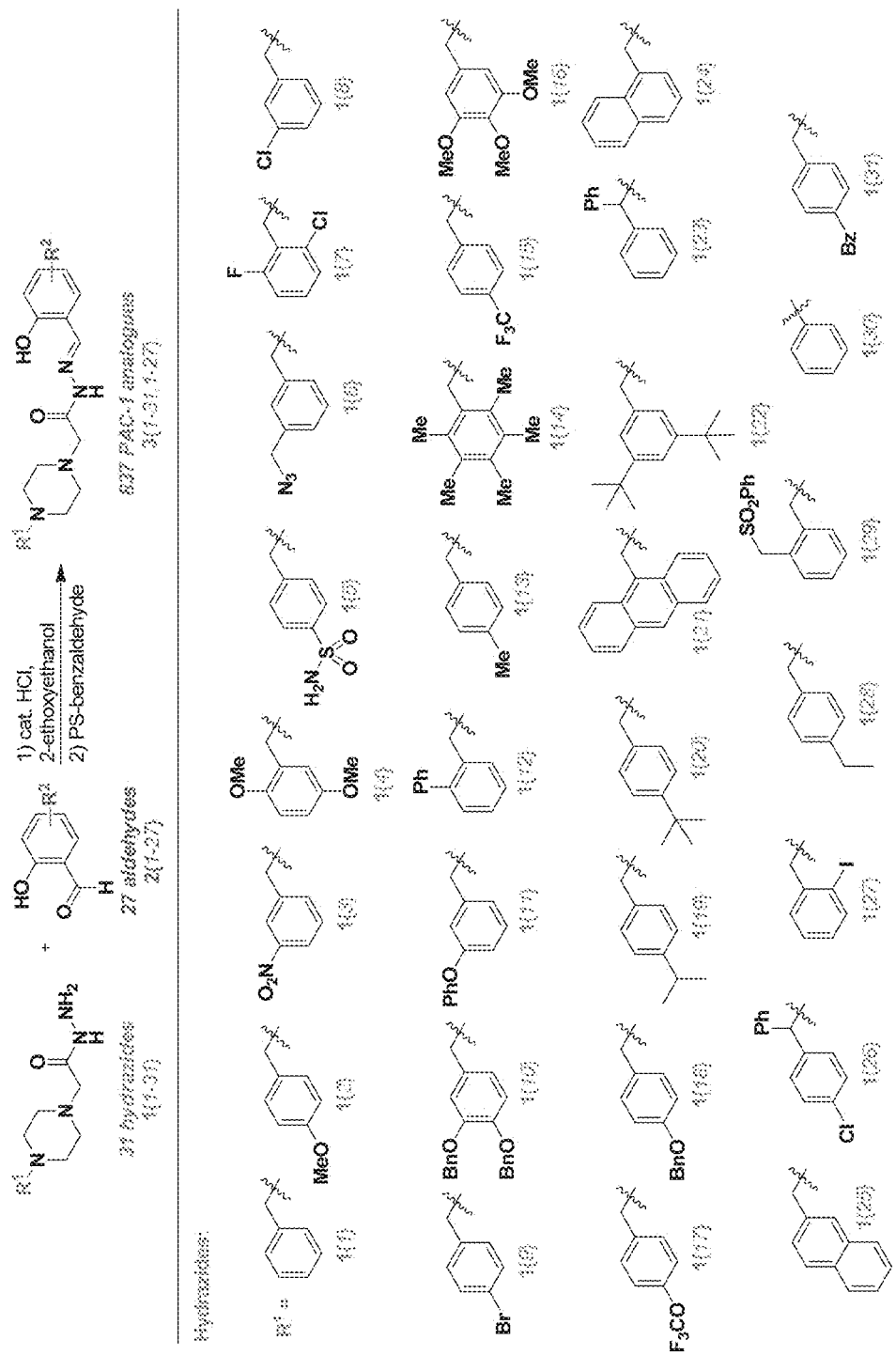
FIG. 1. Hydrazides used to construct 837-membered combinatorial library of PAC-1 analogues.

In 2006, the discovery of Procaspase-Activating Compound 1 (PAC-1, Scheme A) was reported (Putt et al., *Nat Chem Biol* 2006, 2, 543-550). PAC-1 enhances the enzymatic activity of procaspase-3 in vitro, induces apoptotic cell death in cancer cells, and shows efficacy in multiple murine tumor models. Structure-activity relationship studies revealed that the activity of PAC-1 in vitro and in cell culture is dependent on the presence of the ortho-hydroxy N-acyl hydrazone moiety (Scheme A), a functional group known to participate in metal chelation. Indeed, zinc is a powerful inhibitor of procaspase-3 enzymatic activity, and the mechanism by which PAC-1 activates procaspase-3 in vitro is through chelation of inhibitory zinc from procaspase-3, which allows procaspase-3 to process itself to the active form. This same basic mechanism appears to be operational in cell culture as well: approximately 10% of cellular zinc is not bound tightly but exists as the "labile zinc pool". As zinc from the labile pool has been shown to co-localize with procaspase-3, it appears that PAC-1 chelation of this labile zinc inside the cells enhances procaspase-3 activity, leading to apoptosis.

Scheme A: PAC-1 and S-PAC-1, with the ortho-hydroxy N-acyl hydrazone motif.

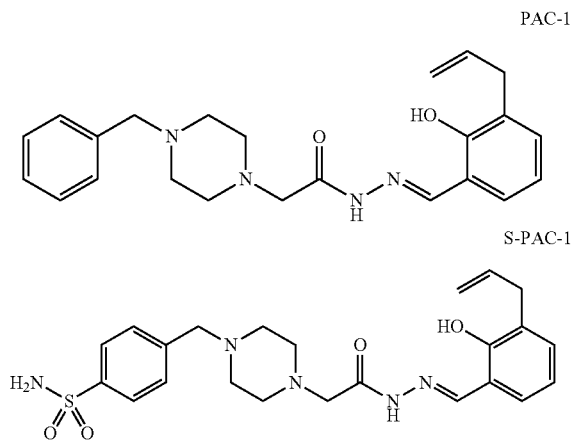

PAC-1 can be safely administered to mice and research dogs at doses that give serum concentrations of ~10 μM for 48 hours. A sulfonamide-containing derivative of PAC-1, called S-PAC-1 (Scheme A), can be safely administered at doses that provide very high serum concentrations in mice (~3.5 mM). Encouragingly, a veterinary clinical trial of S-PAC-1 (administered as a 24- or 72-hour continuous IV infusion) in pet dogs with spontaneously-occurring lymphoma revealed this compound to be safe in all veterinary patients and effective at reducing or stabilizing tumor growth in 4 out of 6 patients. This result provides proof-of-concept for the notion that procaspase-3 activation via small molecule chelation of labile zinc can be a safe and effective anticancer strategy. In the continued search for more potent derivatives of PAC-1, we report herein the parallel synthesis of a combinatorial library of 837 PAC-1 analogues, the evaluation of these compounds for their ability to induce death of cancer cells in culture, and further characterization of six analogues of PAC-1 with enhanced potency.

Design and Synthesis of Combinatorial Library Based on PAC-1.

A library of PAC-1 analogues was designed with the goal of identifying compounds capable of eliciting potent death of cancer cells in culture. As the maximal cytotoxicity of S-PAC-1 is not reached until at least 24 hours, and both PAC-1 and S-PAC-1 exhibit short half-lives of 1-2 hours in vivo, a secondary goal of this study was to identify PAC-1 analogues that could induce apoptosis more rapidly. Reported synthetic routes to PAC-1 and S-PAC-1, as well as other PAC-1 analogues, utilize the condensation of a hydrazide and an aldehyde as the final step in the synthetic scheme (U.S. Patent Publication No. 2007/0049602) (WO 2008/134474 (Hergenrother et al.)). This modular nature of the PAC-1 synthesis allows for a diverse array of functional groups to be conveniently incorporated into the PAC-1 scaffold without altering the core ortho-hydroxy N-acyl hydrazone motif essential for procaspase-3 activation and induction of apoptosis.

Figure 2:
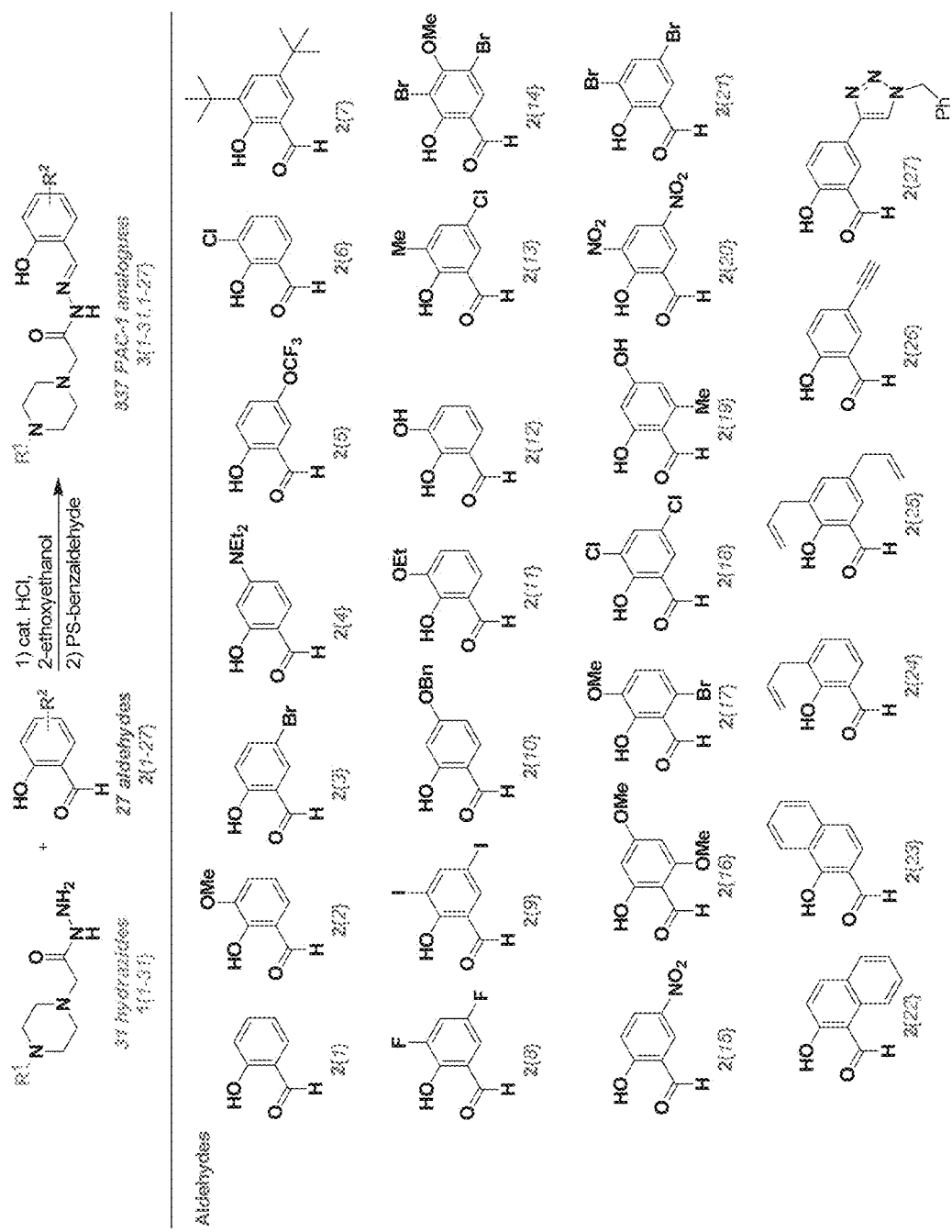
FIG. 2. Aldehydes used to construct 837-membered combinatorial library of PAC-1 analogues.

As shown in FIGS. 1 and 2, 31 hydrazides (1{1-31}) and 27 aldehydes (2{1-27}) were selected for building the library of 837 PAC-1 analogues. The hydrazides were constructed from commercially available benzyl halide starting materials. The syntheses of hydrazides 1{1-6} have been reported previously (Putt et al., *Nat Chem Biol* 2006, 2, 543-550; Peterson et al., *J Med Chem* 2009, 52, 5721-5731; Peterson et al., *Cancer Res* 2010, 70, 7232-41). Hydrazides 1{7-27} were synthesized according to Scheme 1. Substituted benzyl halides 4{7-27} first reacted with piperazine to form substituted benzylpiperazines 5{7-27}. A second alkylation of the piperazine ring with ethyl chloroacetate gave disubstituted piperazines 6{7-27}, and the esters were then converted to hydrazides 1{7-27} by reaction with hydrazine.

Scheme 1: Synthesis of hydrazides 1{7-27}.

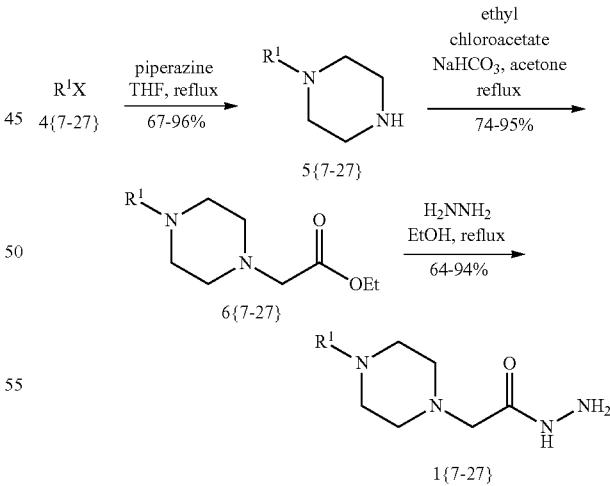

The synthetic routes toward hydrazides 1{28-31} are detailed in Scheme 2. Synthesis of hydrazide 1{28} began by the alkylation of piperazine with 4-vinylbenzyl chloride (7) to form monosubstituted piperazine 8 (Scheme 2, equation 1). A second alkylation with ethyl chloroacetate formed ester 9, and reaction with hydrazine formed the hydrazide and reduced the olefin, giving hydrazide 1{28}. The reduction of olefins with hydrazine typically involves the addition of an oxidizing agent (Miller, C. E., Hydrogenation with Diimide. *J Chem Educ* 1965, 42, 254), but the presence of atmospheric oxygen was sufficient to achieve this transformation.
Scheme 2: Synthesis of hydrazides 1 {28-31}.
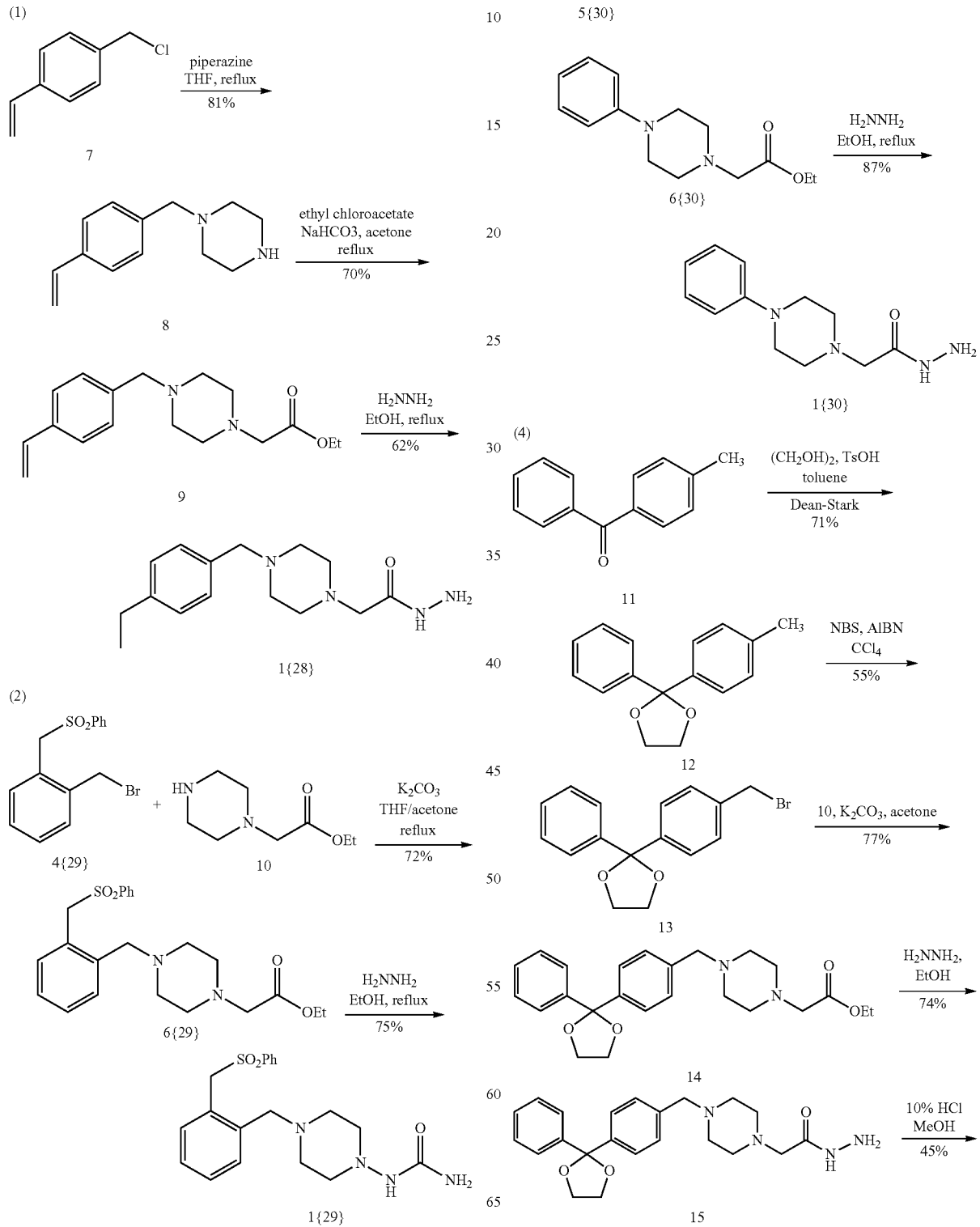

-continued

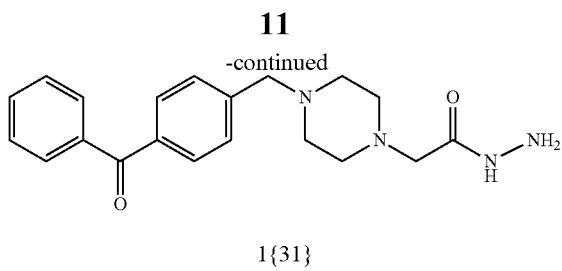

1{31}

Synthesis of hydrazide 1{29} (Scheme 2, equation 2) began with the reaction of ethyl 2-(piperazin-1-yl)acetate (10) with benzyl bromide 4{29} to form intermediate 6{29}. Reaction of 6{29} with hydrazine then formed hydrazide 1{29}. Hydrazide 1{30} (Scheme 2, equation 3) was synthesized beginning with the reaction of 1-phenylpiperazine (5{30}) with ethyl chloroacetate to give disubstituted piperazine 6{30}, and reaction with hydrazine formed hydrazide 1{30}. Hydrazide 1{31}, was synthesized by first protecting 4-methylbenzophenone (11) as the ethylene acetal (12), as shown in Scheme 2, equation 4. This compound was brominated under radical conditions to give benzyl bromide 13. Reaction with monosubstituted piperazine 10 gave intermediate 14, and reaction with hydrazine gave hydrazide 15. Deprotection of the acetal with aqueous acid gave hydrazide 1{31}.

The structure-activity relationship of PAC-1 derived from the synthesis and evaluation of ~30 compounds demonstrated the necessity of the ortho-hydroxyl group, so 27 salicylaldehyde building blocks were selected for library construction. Aldehydes 2{1-23} were obtained from commercial sources, and the syntheses of aldehydes 2{24-26} have been reported previously (Peterson et al., *J Med Chem* 2009, 52, 5721-5731; Peterson et al., *Cancer Res* 2010, 70, 7232-41; Chang et al., *Dalton Trans* 2004, 1731-8). Aldehyde 2{27} was synthesized via copper-catalyzed cycloaddition of aldehyde 2{26} with benzyl azide, as shown in Scheme 3.

Scheme 3: Synthesis of aldehyde 2{27}.

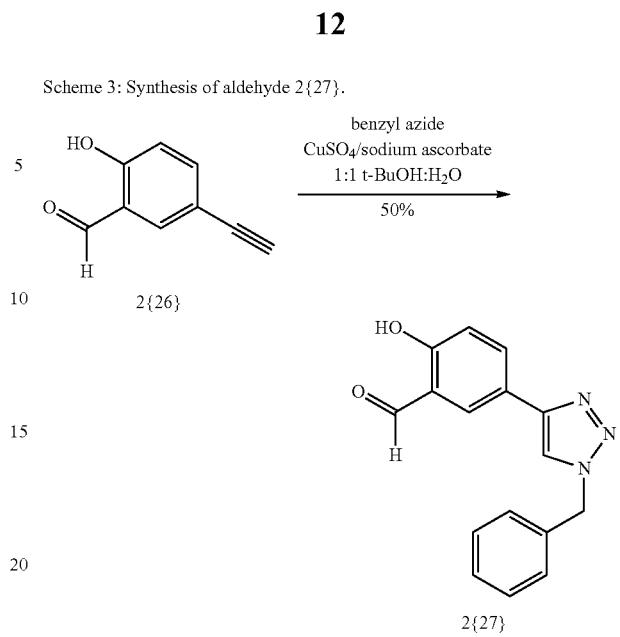

Using a Büchi Syncore parallel synthesizer, each hydrazide was condensed with each aldehyde, with over 80 reactions performed simultaneously. Each aldehyde (5-15 mg) was allowed to react with excess hydrazide (1.7 equiv), and mass spectrometry was used to monitor the disappearance of the aldehyde from the reaction mixture. When the aldehyde had reacted completely, polystyrene-bound benzaldehyde was added as a scavenger resin to react with and remove the excess hydrazide. When mass spectrometry showed no hydrazide remaining, the beads were filtered, and the solutions were dried under high vacuum. Each of the 837 compounds was assessed by HPLC/MS. The purity of each compound is listed in Table A. The library members had an average purity of 91%.

TABLE A

Purity of PAC-1 analogs as determined by LC/MS.

| | 2{1} | 2{2} | 2{3} | 2{4} | 2{5} | 2{6} | 2{7} | 2{8} | 2{9} | 2{10} | 2{11} | 2{12} | 2{13} | 2{14} |
|---|---|---|---|---|---|---|---|---|---|---|---|---|---|---|
| 1{1} | 91% | 93% | 90% | 85% | 91% | 92% | 98% | 96% | 92% | 95% | 99% | 96% | 95% | 96% |
| 1{2} | 92% | 91% | 90% | 91% | 93% | 95% | 99% | 96% | 95% | 92% | 96% | 94% | 99% | 93% |
| 1{3} | 91% | 94% | 91% | 95% | 79% | 88% | 97% | 89% | 91% | 91% | 97% | 83% | 99% | 99% |
| 1{4} | 93% | 98% | 96% | 99% | 96% | 98% | 99% | 96% | 90% | 99% | 100% | 91% | 94% | 92% |
| 1{5} | 94% | 96% | 97% | 93% | 90% | 97% | 100% | 98% | 90% | 98% | 97% | 93% | 61% | 96% |
| 1{6} | 98% | 98% | 97% | 72% | 95% | 100% | 97% | 90% | 94% | 95% | 98% | 96% | 95% | 96% |
| 1{7} | 93% | 98% | 93% | 98% | 93% | 96% | 98% | 98% | 96% | 98% | 100% | 97% | 100% | 94% |
| 1{8} | 89% | 93% | 91% | 90% | 90% | 94% | 96% | 95% | 90% | 95% | 93% | 92% | 97% | 93% |
| 1{9} | 92% | 90% | 88% | 92% | 82% | 91% | 96% | 92% | 94% | 92% | 92% | 93% | 92% | 90% |
| 1{10} | 92% | 88% | 84% | 90% | 93% | 90% | 93% | 91% | 89% | 84% | 90% | 93% | 91% | 83% |
| 1{11} | 91% | 92% | 86% | 90% | 89% | 91% | 96% | 92% | 90% | 89% | 93% | 96% | 96% | 92% |
| 1{12} | 84% | 86% | 83% | 87% | 95% | 85% | 95% | 86% | 87% | 87% | 83% | 96% | 89% | 85% |
| 1{13} | 95% | 86% | 86% | 92% | 89% | 91% | 96% | 95% | 90% | 86% | 93% | 91% | 90% | 89% |
| 1{14} | 99% | 90% | 95% | 93% | 92% | 97% | 93% | 94% | 98% | 96% | 92% | 95% | 99% | 89% |
| 1{15} | 98% | 87% | 85% | 99% | 94% | 86% | 92% | 93% | 82% | 88% | 93% | 99% | 95% | 82% |
| 1{16} | 95% | 95% | 88% | 85% | 87% | 91% | 92% | 95% | 85% | 93% | 90% | 87% | 94% | 74% |
| 1{17} | 86% | 95% | 89% | 73% | 84% | 92% | 95% | 92% | 86% | 82% | 89% | 97% | 93% | 80% |
| 1{18} | 82% | 100% | 85% | 85% | 100% | 100% | 100% | 100% | 85% | 94% | 100% | 94% | 100% | 100% |
| 1{19} | 93% | 99% | 100% | 70% | 100% | 92% | 94% | 94% | 87% | 99% | 93% | 98% | 100% | 93% |
| 1{20} | 99% | 98% | 93% | 86% | 84% | 96% | 90% | 85% | 92% | 90% | 91% | 89% | 100% | 98% |
| 1{21} | 88% | 80% | 89% | 85% | 93% | 85% | 88% | 90% | 100% | 86% | 99% | 100% | 92% | 92% |
| 1{22} | 88% | 96% | 85% | 86% | 89% | 90% | 86% | 90% | 86% | 87% | 91% | 95% | 90% | 86% |
| 1{23} | 88% | 86% | 84% | 87% | 91% | 85% | 98% | 92% | 93% | 98% | 87% | 88% | 96% | 81% |
| 1{24} | 89% | 91% | 98% | 96% | 97% | 94% | 99% | 92% | 96% | 97% | 95% | 95% | 89% | 86% |
| 1{25} | 100% | 96% | 96% | 93% | 95% | 96% | 98% | 91% | 91% | 95% | 97% | 95% | 92% | 92% |
| 1{26} | 90% | 93% | 88% | 87% | 83% | 88% | 96% | 86% | 93% | 90% | 94% | 91% | 97% | 90% |
| 1{27} | 93% | 92% | 92% | 87% | 80% | 94% | 95% | 91% | 89% | 90% | 92% | 92% | 91% | 88% |
| 1{28} | 86% | 83% | 98% | 82% | 86% | 97% | 86% | 94% | 87% | 84% | 66% | 88% | 86% | 86% |

TABLE A-continued

Purity of PAC-1 analogs as determined by LC/MS.

| | | | | | | | | | | | | | |
|---|---|---|---|---|---|---|---|---|---|---|---|---|---|
| 1{29} | 86% | 91% | 93% | 88% | 86% | 94% | 98% | 90% | 94% | 89% | 91% | 93% | 83% | 91% |
| 1{30} | 87% | 92% | 85% | 86% | 90% | 90% | 95% | 90% | 93% | 83% | 91% | 92% | 86% | 85% |
| 1{31} | 82% | 83% | 83% | 90% | 82% | 86% | 96% | 83% | 86% | 90% | 92% | 94% | 84% | 91% |

| | 2{15} | 2{16} | 2{17} | 2{18} | 2{19} | 2{20} | 2{21} | 2{22} | 2{23} | 2{24} | 2{25} | 2{26} | 2{27} |
|---|---|---|---|---|---|---|---|---|---|---|---|---|---|
| 1{1} | 98% | 86% | 95% | 98% | 93% | 97% | 95% | 95% | 95% | 97% | 99% | 99% | 100% |
| 1{2} | 91% | 86% | 90% | 93% | 93% | 90% | 91% | 95% | 93% | 93% | 71% | 96% | 96% |
| 1{3} | 85% | 90% | 87% | 86% | 80% | 90% | 87% | 87% | 87% | 92% | 86% | 88% | 91% |
| 1{4} | 93% | 90% | 95% | 91% | 88% | 95% | 89% | 90% | 88% | 96% | 86% | 93% | 98% |
| 1{5} | 98% | 90% | 96% | 97% | 91% | 97% | 97% | 88% | 88% | 88% | 89% | 90% | 89% |
| 1{6} | 92% | 100% | 100% | 95% | 92% | 92% | 97% | 95% | 92% | 90% | 80% | 83% | 89% |
| 1{7} | 98% | 83% | 96% | 97% | 86% | 92% | 100% | 93% | 99% | 93% | 97% | 89% | 96% |
| 1{8} | 94% | 81% | 90% | 94% | 85% | 98% | 97% | 96% | 96% | 93% | 96% | 85% | 84% |
| 1{9} | 92% | 92% | 90% | 90% | 96% | 93% | 89% | 82% | 90% | 88% | 90% | 82% | 87% |
| 1{10} | 91% | 77% | 85% | 83% | 88% | 85% | 87% | 89% | 92% | 97% | 90% | 91% | 90% |
| 1{11} | 91% | 90% | 88% | 94% | 89% | 90% | 91% | 95% | 91% | 92% | 88% | 90% | 88% |
| 1{12} | 81% | 86% | 86% | 94% | 86% | 100% | 90% | 87% | 90% | 90% | 82% | 88% | 83% |
| 1{13} | 94% | 91% | 85% | 84% | 90% | 100% | 86% | 90% | 90% | 90% | 91% | 83% | 98% |
| 1{14} | 87% | 95% | 85% | 90% | 87% | 86% | 92% | 95% | 99% | 95% | 94% | 82% | 88% |
| 1{15} | 87% | 84% | 90% | 88% | 92% | 100% | 91% | 91% | 90% | 93% | 96% | 93% | 98% |
| 1{16} | 87% | 59% | 82% | 88% | 88% | 91% | 83% | 85% | 86% | 93% | 80% | 93% | 93% |
| 1{17} | 84% | 86% | 86% | 90% | 87% | 100% | 81% | 86% | 88% | 89% | 89% | 80% | 97% |
| 1{18} | 100% | 52% | 100% | 100% | 85% | 100% | 94% | 88% | 100% | 100% | 83% | 91% | 95% |
| 1{19} | 92% | 83% | 88% | 97% | 66% | 100% | 92% | 75% | 99% | 98% | 90% | 87% | 98% |
| 1{20} | 90% | 86% | 89% | 99% | 86% | 99% | 95% | 86% | 99% | 98% | 92% | 90% | 87% |
| 1{21} | 100% | 85% | 100% | 96% | 67% | 95% | 92% | 84% | 93% | 93% | 92% | 92% | 86% |
| 1{22} | 90% | 72% | 84% | 85% | 87% | 92% | 87% | 86% | 86% | 89% | 88% | 95% | 85% |
| 1{23} | 88% | 90% | 86% | 96% | 90% | 100% | 97% | 83% | 84% | 98% | 85% | 81% | 90% |
| 1{24} | 94% | 81% | 89% | 84% | 86% | 96% | 81% | 97% | 97% | 96% | 93% | 96% | 95% |
| 1{25} | 95% | 82% | 90% | 90% | 87% | 94% | 90% | 93% | 94% | 94% | 86% | 92% | 88% |
| 1{26} | 83% | 89% | 87% | 85% | 91% | 97% | 89% | 88% | 91% | 94% | 91% | 89% | 92% |
| 1{27} | 94% | 89% | 90% | 90% | 91% | 94% | 90% | 88% | 89% | 90% | 95% | 82% | 95% |
| 1{28} | 93% | 85% | 96% | 91% | 85% | 100% | 86% | 55% | 85% | 81% | 94% | 88% | 90% |
| 1{29} | 90% | 90% | 87% | 86% | 89% | 98% | 87% | 95% | 95% | 89% | 87% | 84% | 88% |
| 1{30} | 93% | 82% | 97% | 91% | 80% | 88% | 88% | 82% | 93% | 89% | 90% | 81% | 98% |
| 1{31} | 79% | 84% | 89% | 80% | 84% | 95% | 89% | 91% | 87% | 91% | 99% | 93% | 90% |

Evaluation of the PAC-1 Combinatorial Library.

With 837 PAC-1 analogues in hand, compounds were evaluated for their ability to induce apoptosis in cell culture. U-937 human lymphoma cells were exposed to the compounds for 24 hours at a concentration of 20 µM. Both PAC-1 and S-PAC-1 display moderate potency (~50% cell death) versus this cell line under these conditions. Apoptotic cell death was assessed by flow cytometry, using Annexin V-FITC/propidium iodide staining. Through this screening process, six compounds were identified and confirmed to induce >80% cell death under these conditions.

Cell Death Induction and Relief of Zinc-Mediated Inhibition of Procaspase-3 by Hit Compounds.

After re-synthesis of the hits (3{2, 7}, 3{4, 7}, 3{18,7}, 3{20,24}, 3{25,7}, and 3{28,7}), analytically pure samples of the compounds were evaluated in further biological assays. These structures and the biological results are shown in Table 1. The compounds were evaluated, at a range of concentrations, for their ability to induce cell death in U-937 cells, as well as their ability to activate procaspase-3 in vitro. All six of these hits were found to be 2-4 fold more potent in cell culture than PAC-1 and S-PAC-1 in a 72-hour treatment.

TABLE 1

Six library compounds induce potent cell death of U-937 cells (human lymphoma) in both 24 and 72 hour experiments, with biomass quantified using the sulforhodamine B assay.

| | 72-hour IC$_{50}$ (µM) | % Cytotoxicity (24 hours at 7.5 µM) | Procaspase-3 (% Activity at 3.5 µm) |
|---|---|---|---|
| | 3.8 ± 0.4 | 21 | 42 ± 1.8 |

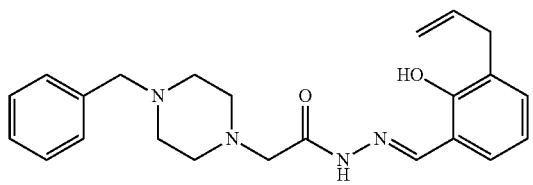 [SMILES: C=CCc1cccc(/C=N/NC(=O)CN2CCN(Cc3ccccc3)CC2)c1O]

PAC-1

TABLE 1-continued
Six library compounds induce potent cell death of U-937 cells (human lymphoma) in
both 24 and 72 hour experiments, with biomass quantified using the sulforhodamine B assay.
| | 72-hour IC$_{50}$ (μM) | % Cytotoxicity (24 hours at 7.5 μM) | Procaspase-3 (% Activity at 3.5 μm) |
|---|---|---|---|
| 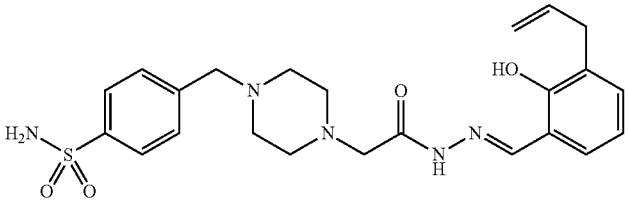 [SMILES: C=CCc1cccc(/C=N/NC(=O)CN2CCN(Cc3ccc(S(N)(=O)=O)cc3)CC2)c1O] S-PAC-1 | 4.4 ± 0.7 | 23 | 4 ± 0.6 |
| 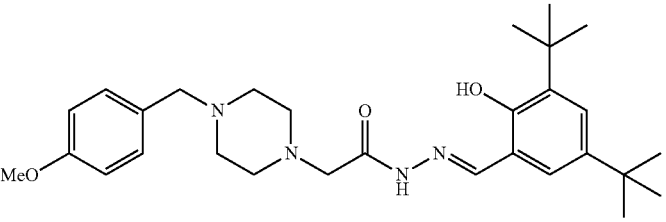 [SMILES: COc1ccc(CN2CCN(CC(=O)N/N=C/c3cc(C(C)(C)C)cc(C(C)(C)C)c3O)CC2)cc1] 3{2,7} | 1.8 ± 0.2 | 90 | 53 ± 4.1 |
| 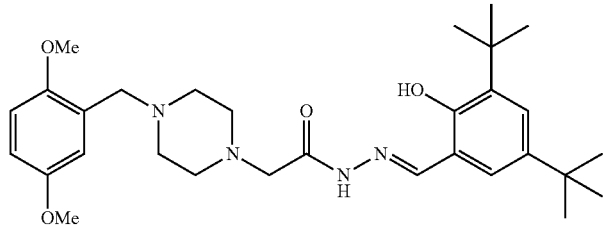 [SMILES: COc1ccc(OC)c(CN2CCN(CC(=O)N/N=C/c3cc(C(C)(C)C)cc(C(C)(C)C)c3O)CC2)c1] 3{4,7} | 1.6 ± 0.2 | 53 | 64 ± 2.5 |
| 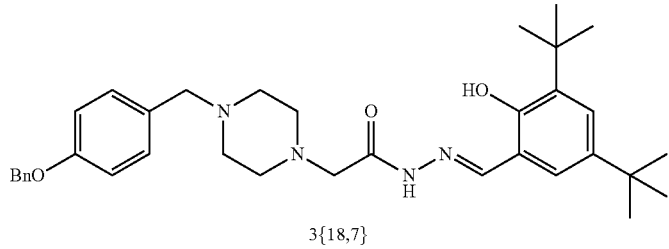 3{18,7} | 1.4 ± 0.2 | 97 | 36 ± 1.6 |
| 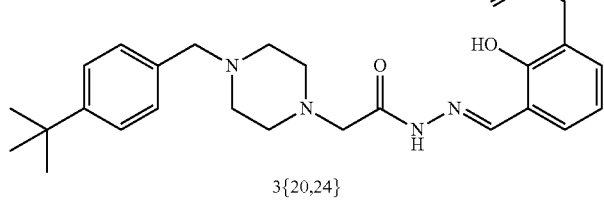 3{20,24} | 0.9 ± 0.03 | 83 | 82 ± 2.4 |
| 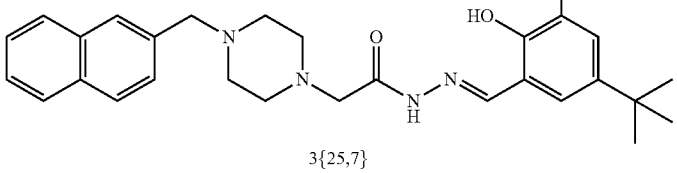 3{25,7} | 1.0 ± 0.04 | 50 | 69 ± 5.3 |

TABLE 1-continued

Six library compounds induce potent cell death of U-937 cells (human lymphoma) in both 24 and 72 hour experiments, with biomass quantified using the sulforhodamine B assay.

| | 72-hour IC$_{50}$ (μM) | % Cytotoxicity (24 hours at 7.5 μM) | Procaspase-3 (% Activity at 3.5 μm) |
|---|---|---|---|
| | 2.0 ± 0.2 | 70 | 60 ± 2.4 |

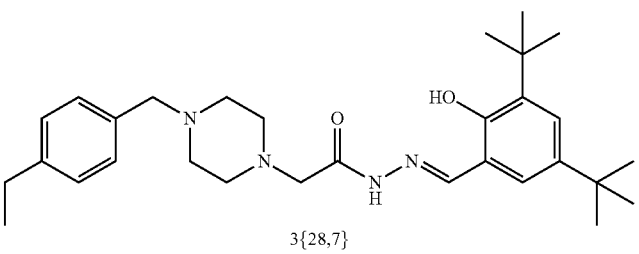

3{28,7}

Figure 3:
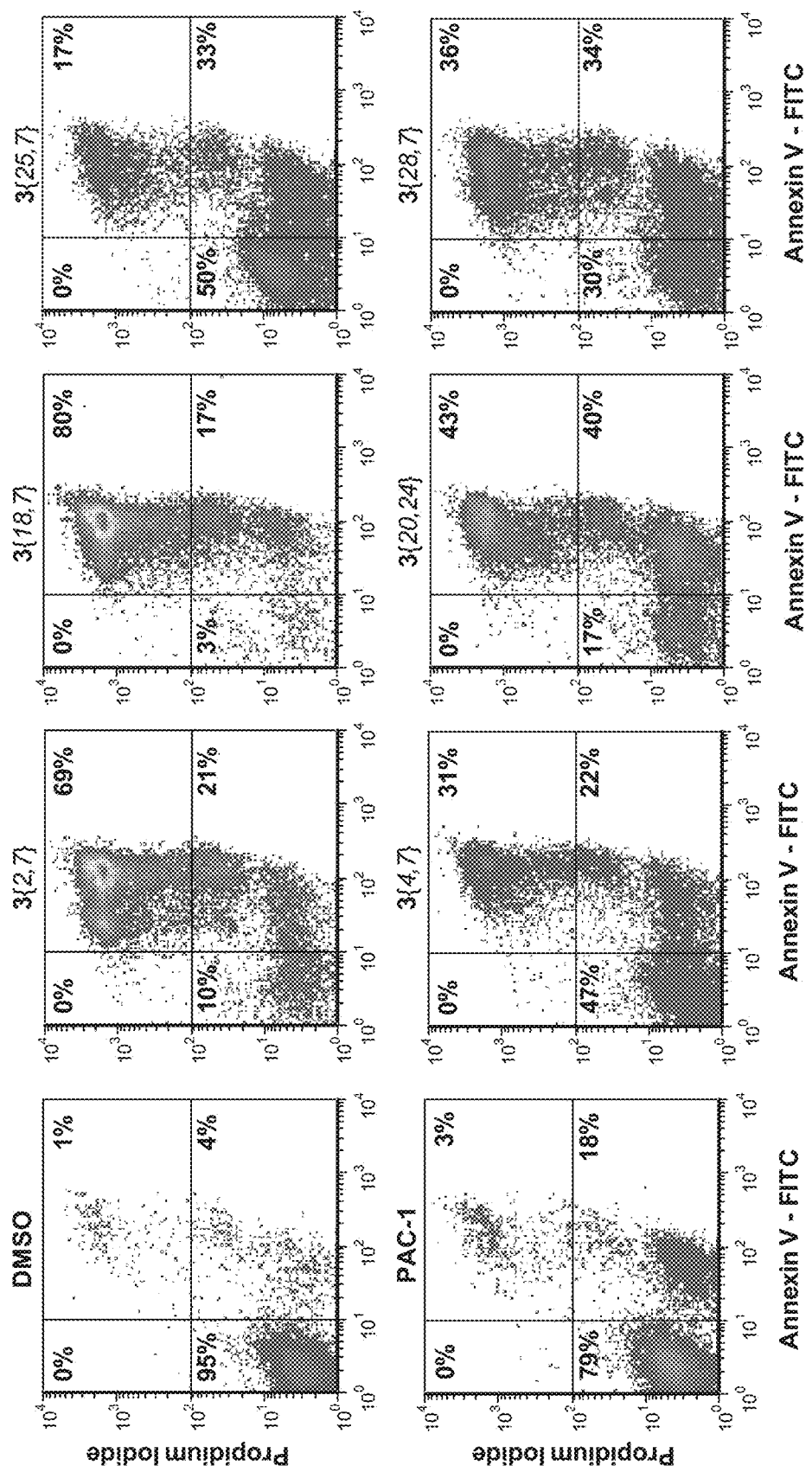
FIG. 3. Annexin V-FITC/propidium iodide staining of U-937 cells treated with 7.5 µM of each compound for 24 hours.

In a second experiment, flow cytometry analysis with Annexin V-FITC/propidium iodide was performed on U-937 cells that were exposed to the compounds at a single concentration (7.5 μM) for 24 hours (Table 1 and FIG. 3). As demonstrated by the histograms in FIG. 3, within 24 hours the majority of the compound treated cells were undergoing apoptosis (cells in the lower right quadrant of the histogram—Annexin V positive, propidium iodide negative), or were in a late apoptotic/necrotic stage (upper right quadrant—Annexin V positive, propidium iodide positive). The novel analogues were found to be more potent than PAC-1 under these 24 hour conditions.

Figure 4:
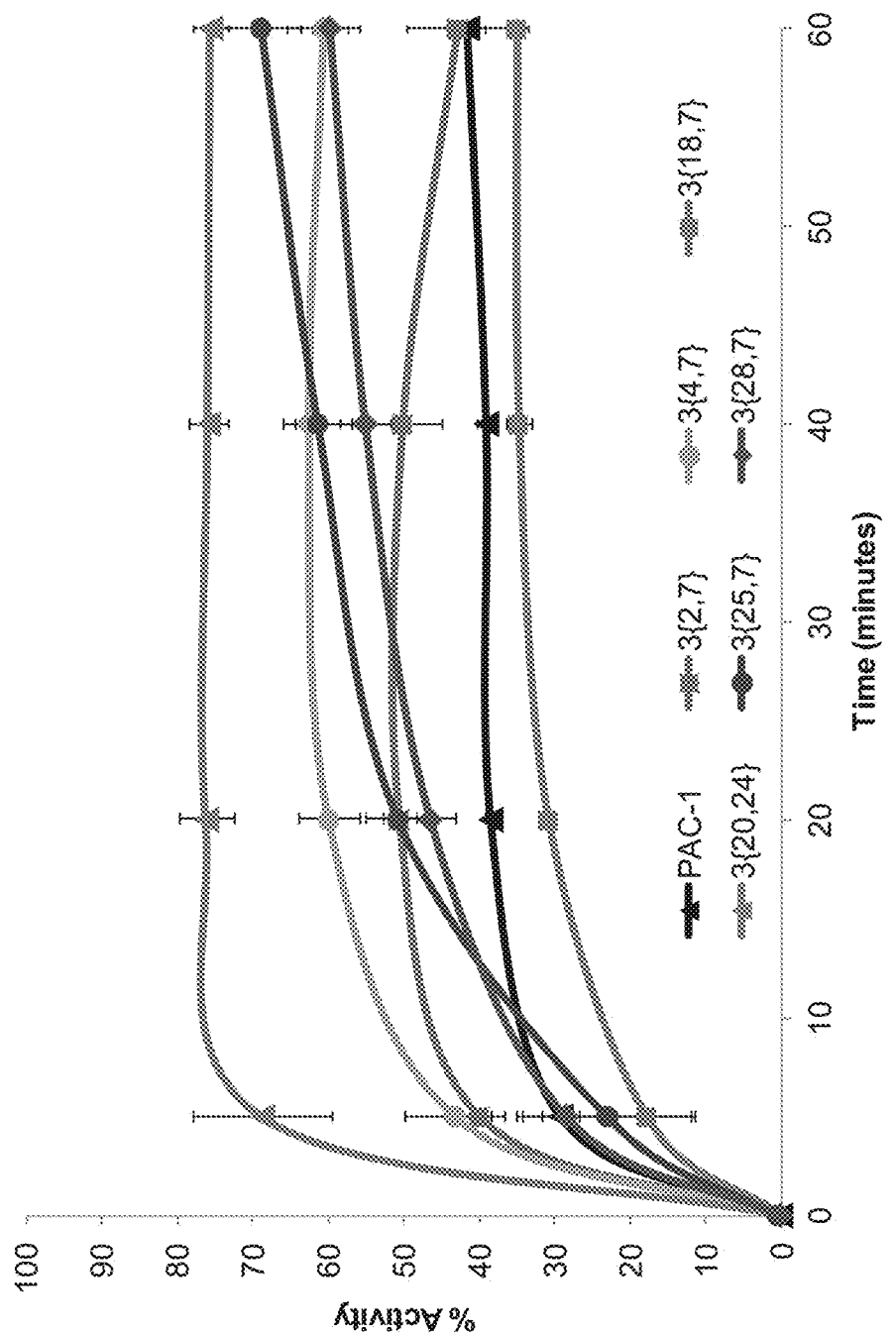
FIG. 4. Relief of zinc-mediated inhibition of 1 µM procaspase-3 by PAC-1 and hit compounds, as measured by the processing of the Ac-DEVD-pNA substrate. Compounds were tested at a concentration of 50 µM with 3.5 µM $ZnSO_4$ and normalized to a DMSO-treated control (0%) and a zinc-free control (100%), and substrate cleavage was monitored at 405 nm.

The six confirmed hits were then evaluated in vitro for their ability to relieve zinc-mediated inhibition of procaspase-3 (Table 1 and FIG. 4). In this experiment, procaspse-3 was incubated with ZnSO$_4$, conditions in which procaspase-3 has no enzymatic activity. All compounds were able to enhance procaspase-3 enzymatic activity under these conditions (as assessed by the cleavage of the colorimetric caspase-3 substrate Ac-DEVD-pNA, synthesized as previously reported (Peterson et al., Nat Protoc 2010, 5, 294-302)), and five of the six hit compounds showed greater activity than PAC-1 in this assay. These data indicate that the compounds enhance the activity of procaspase-3 in vitro through chelation of inhibitory zinc, and suggest that in the cell the compounds chelate zinc from the labile pool, allowing procaspase-3 to be processed to active caspase-3, leading to apoptotic cell death.

The direct modulation of apoptotic proteins is a practical anticancer strategy. PAC-1 and its derivative S-PAC-1, which chelate labile cellular zinc and induce apoptosis in cancer cells, have been effective in various preclinical anti-tumor models. However, derivatives that induce cell death more rapidly and more potently would be even more attractive as therapeutics. Using parallel synthesis and guided by the known SAR, we constructed 837 PAC-1 analogues and evaluated them for their cell death inducing properties. The six compounds shown in Table 1 emerged from this effort. These compounds are two- to four-fold more potent than PAC-1 at induction of cancer cell death in both 24-hour and 72-hour assays.

Given the general hydrophobicity of the hit compounds relative to PAC-1, the enhanced potency and enhanced rate of cell death may be driven by enhanced cell permeability. These qualities are likely to be advantageous as the compounds are moved forward in vivo. In addition, other members of this library will likely emerge as viable in vivo candidates as alternate properties (such as propensity to cross the blood-brain barrier, improved metabolic stability, improved solubility/formulation for in vivo studies, etc.) are examined. Thus, this library of 837 compounds will be a rich source from which to develop next-generation procaspase-3 activating compounds.

Definitions

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "cancer cell" encompasses definitions as broadly understood in the art. In one embodiment, the term refers to an abnormally regulated cell that can contribute to a clinical condition of cancer in a human or animal. In some embodiments, the term can refer to a cultured cell line or a cell within or derived from a human or animal body. A cancer cell can be of a wide variety of differentiated cell, tissue, or organ types as is understood in the art, and also as described herein.

The terms alkyl, cycloalkyl, alkenyl, alkenyl, aryl, amino groups, alkoxy, halo, haloalkyl, heteroaryl, heterocycle, and ester are well known in the art and have their art-recognized definitions, such as described in U.S. Patent Publication No. 2012/0040995 (Hergenrother et al.).

The compounds of this invention include all novel stereochemical isomers arising from the substitution of disclosed compounds.

Pharmaceutical Formulations

The compounds described herein can be used to prepare therapeutic pharmaceutical compositions. The compounds may be added to the compositions in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 2% to about 60% of the weight of a given unit dosage form. The amount of active compound in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

For topical administration, compounds may be applied in pure form, e.g., when they are liquids. However, it will generally be desirable to administer the active agent to the skin as a composition or formulation, for example, in combination with a dermatologically acceptable carrier, which may be a solid or a liquid.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds described herein can be effective anti-tumor agents and have higher potency and/or reduced toxicity as compared to PAC-1. Preferably, compounds of the invention are more potent and less toxic than PAC-1, and/or avoid a potential site of catabolic metabolism encountered with PAC-1, i.e., they have a different metabolic profile than PAC-1.

The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known. In addition, ability of a compound to treat cancer may be determined using the tests as described below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. General Procedure for the Synthesis of PAC-1 Analogues

To a 16×150 mm test tube were added hydrazide (1.7 equiv), aldehyde (1.0 equiv), 2-ethoxyethanol (1 mL), and 1.2 M HCl (10 mol %). The tubes were shaken on a Büchi Syncore parallel synthesizer at 110° C. until all aldehyde had reacted (as monitored by ESI-MS). The reaction mixture was cooled to room temperature (~23° C.), and polystyrene-benzaldehyde (3.5 equiv) was added. The reaction mixture was shaken at 25-80° C. until no hydrazide remained (as monitored by ESI-MS). The reaction mixture was cooled to room temperature, and the resin was filtered and washed with 2-ethoxyethanol. The filtrate was dried under high vacuum to afford the PAC-1 analogue.

Example 2. Parallel Synthesis of 837 Analogues of PAC-1

Reactions requiring anhydrous conditions were conducted under a positive atmosphere of nitrogen or argon in oven-dried glassware. Standard syringe techniques were used for anhydrous addition of liquids. Unless otherwise noted, all starting materials, solvents, and reagents were acquired from commercial suppliers and used without further purification. Flash chromatography was performed using 230-400 mesh silica gel. Compounds 1{1}, 1{2}, 1{3}, 1{4}, 1{5}, 1{6}, 2{24}, 2{25}, 2{26}, and PAC-1 were synthesized as previously reported.

Compound Analysis. NMR experiments were recorded either in CDCl$_3$ (Sigma), CD$_3$OD (Sigma) or (CD$_3$)$_2$CO (Sigma) on a Varian Unity 400 MHz or 500 MHz spectrometer with residual undeuterated solvent as the internal reference for $^1$H-NMR and $^{13}$C-NMR experiments and 1% CFCl$_3$/CDCl$_3$ as the external reference for $^{19}$F-NMR experiments. Chemical shift, δ (ppm); coupling constants, J (Hz); multiplicity (s=singlet, d=doublet, t=triplet, q=quartet, m=multiplet, br=broad); and integration are reported. High-resolution mass spectral data was recorded on a Micromass Q-Tof Ultima hybrid quadrupole/time-of-flight ESI mass spectrometer at the University of Illinois Mass Spectrometry Laboratory.

General Procedure A: Synthesis of 1-benzylpiperazines

Anhydrous piperazine (6.0 equiv.) was suspended in THF (0.45 M benzyl halide). The mixture was heated to reflux until piperazine fully dissolved. Upon dissolution, the substituted benzyl halide (1.0 equiv.) was added to the reaction mixture. A white solid immediately formed. The reaction mixture was stirred at reflux for 2.5 hours. The mixture was cooled to room temperature. The solid was filtered and washed with THF and EtOAc. The combined filtrates were concentrated to 10% of the original volume. The concentrate was poured into a separatory funnel with 5% brine/H$_2$O made basic (pH>12) with KOH. The aqueous layer was extracted with DCM and EtOAc. The organic layers were combined, dried over Na$_2$SO$_4$, and concentrated. The crude product was purified by silica gel column chromatography to yield pure 1-benzylpiperazine.

General Procedure B: Synthesis of Ethyl Esters

The substituted 1-benzylpiperazine (1.0 equiv.) was dissolved in acetone (0.5 M), and chloroform was added to some reaction mixtures as needed to fully dissolve the 1-benzylpiperazine. NaHCO$_3$ (1.25 equiv.) was added, and the mixture was stirred at room temperature. Ethyl chloroacetate (1.1 equiv.) was then added dropwise. The reaction mixture was stirred overnight at reflux. The reaction mixture was cooled to room temperature. The solid was filtered and washed with acetone. The filtrate was concentrated. The crude product was purified by silica gel column chromatography to yield pure ethyl ester.

General Procedure C: Synthesis of Hydrazides

The substituted ethyl 2-(4-benzylpiperazin-1-yl)acetate (1.0 equiv.) was dissolved in EtOH (0.5 M). The solution was stirred, and anhydrous hydrazine (3.0-4.0 equiv.) was added dropwise. The reaction mixture was stirred at reflux overnight. The reaction mixture was cooled to room temperature and concentrated. The concentrate was transferred to a separatory funnel containing 1:1 brine:H$_2$O made basic (pH>12) with KOH. The aqueous layer was extracted with DCM (3×) and EtOAc (1×). The combined organic layers were dried over MgSO$_4$ and concentrated. The crude product was purified by silica gel column chromatography or recrystallization to yield pure hydrazide.
Scheme B
Starting materials used for synthesis of hydrazides.
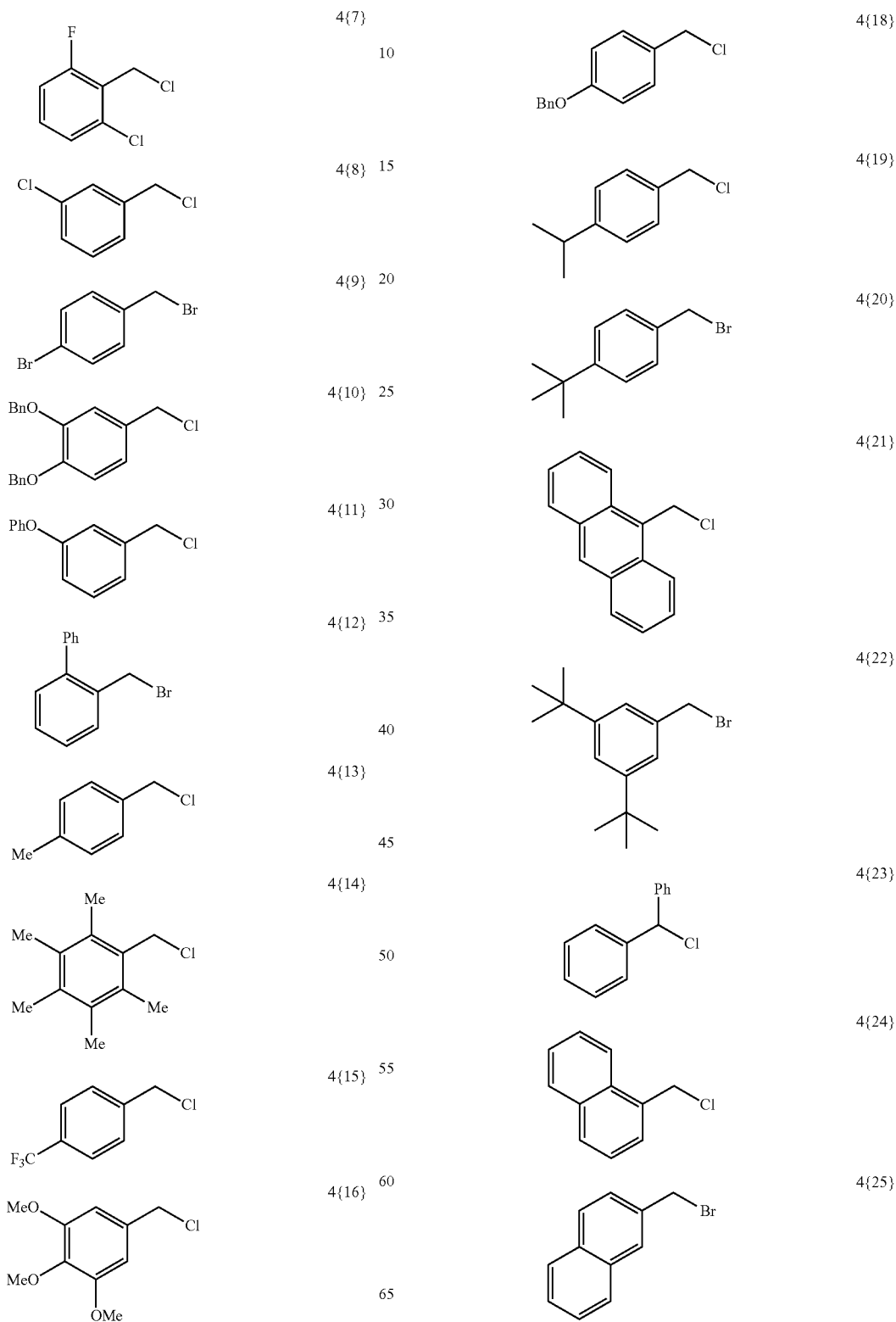

4{26}

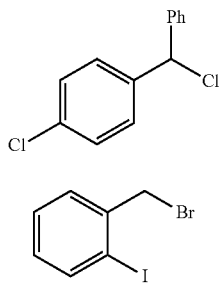

4{27}

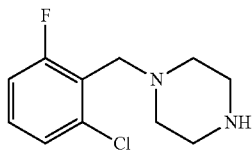 [SMILES: Fc1cccc(Cl)c1CN1CCNCC1]

1-(2-chloro-6-fluorobenzyl)piperazine (5{7})

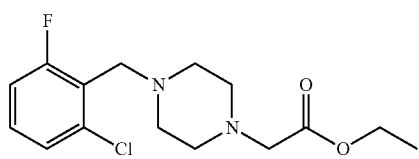 [SMILES: CCOC(=O)CN1CCN(Cc2c(F)cccc2Cl)CC1]

Synthesized according to General Procedure A: 2-chloro-6-fluorobenzyl chloride (4{7}, 5 mL, 39.1 mmol, 1 equiv.), piperazine (20.2 g, 234.8 mmol, 6 equiv.), THF (85.4 mL). Purification with flash column chromatography on silica gel (4:1 EtOAc:MeOH) afforded 5{7} (6.92 g, 77%) as a white solid. $^1$H-NMR (400 MHz, CDCl$_3$): δ 7.14-7.08 (m, 2H), 6.94-6.86 (m, 1H), 3.62 (d, 2H, J=2.0 Hz), 2.78 (t, 4H, J=4.8 Hz), 2.44 (br s, 4H), 1.40 (br s, 1H). $^{13}$C-NMR (100 MHz, CDCl$_3$): δ 161.8 (d, J$_{C-F}$=247.5 Hz), 136.4 (d, J$_{C-F}$=6.0 Hz), 128.8 (d, J$_{C-F}$=9.6 Hz), 125.2, 123.6 (d, J$_{C-F}$=18.0 Hz), 113.7 (d, J$_{C-F}$=23.3 Hz), 54.0, 52.8, 45.9.

Ethyl 2-(4-(2-chloro-6-fluorobenzyl)piperazin-1-yl)acetate (6{7})

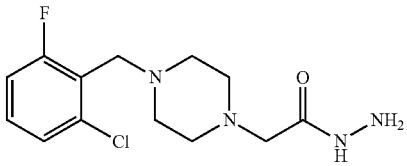 [SMILES: NNC(=O)CN1CCN(Cc2c(F)cccc2Cl)CC1]

Synthesized according to General Procedure B: 5{7} (6.78 g, 29.6 mmol, 1 equiv.), ethyl chloroacetate (3.49 mL, 32.6 mmol, 1.1 equiv.), NaHCO$_3$ (3.11 g, 37.0 mmol, 1.25 equiv.), acetone (59.2 mL). Purification with flash column chromatography on silica gel (1:1 hexanes:EtOAc) afforded 6{7} (8.65 g, 93%) as a yellow liquid. $^1$H-NMR (400 MHz, CDCl$_3$): δ 7.16-7.10 (m, 2H), 6.94-6.89 (m, 1H), 4.12 (q, 2H, J=7.2 Hz) 3.69 (d, 2H, J=2.0 Hz), 3.12 (s, 2H), 2.59 (br s, 4H), 2.52 (br s, 4H), 1.20 (t, 3H, J=7.2 Hz). $^{13}$C-NMR (100 MHz, CDCl$_3$): δ 170.1, 161.9 (d, J$_{C-F}$=247.6 Hz), 136.5 (d, J$_{C-F}$=5.8 Hz), 128.9 (br), 125.2 (br), 123.5 (d, J$_{C-F}$=18.2 Hz), 113.8 (d, J$_{C-F}$=22.9 Hz), 60.4, 59.3, 52.9, 52.1, 52.0, 14.1.

2-(4-(2-chloro-6-fluorobenzyl)piperazin-1-yl)acetohydrazide (1{7})

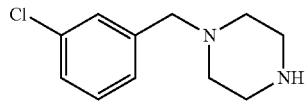 [SMILES: Clc1cccc(CN2CCNCC2)c1]

Synthesized according to General Procedure C: 6{7} (8.65 g, 27.5 mmol, 1 equiv.), anhydrous hydrazine (2.6 mL, 82.4 mmol, 3 equiv.), ethanol (37.9 mL). Purification by silica gel column chromatography (4:1 EtOAc:MeOH) afforded 1{7} (8.27 g, 92%) as a white solid. $^1$H-NMR (400 MHz, CDCl$_3$): δ 8.14 (br s, 1H) 7.22-7.15 (m, 2H), 6.99-6.94 (m, 1H), 3.83 (br s, 2H) 3.70 (d, 2H, J=2.0 Hz), 3.04 (s, 2H), 2.55 (br s, 4H), 2.50 (br s, 4H). $^{13}$C-NMR (100 MHz, CDCl$_3$): δ 170.5, 162.0 (d, J$_{C-F}$=247.6 Hz), 136.5 (d, J$_{C-F}$=5.9 Hz), 129.2 (br), 125.4 (br), 123.5 (d, J$_{C-F}$=18.1 Hz), 113.9 (br), 60.5, 53.5, 52.6, 52.1.

1-(3-chlorobenzyl)piperazine (5{8})

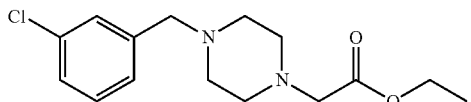

Synthesized according to General Procedure A: 3-chlorobenzyl chloride (4{8}, 5 mL, 39.3 mmol, 1 equiv.), piperazine (20.3 g, 235.7 mmol, 6 equiv.), THF (85.4 mL). Purification with flash column chromatography on silica gel (4:1 EtOAc:MeOH) afforded 5{8} (5.41 g, 65%) as a light yellow liquid. $^1$H-NMR (400 MHz, CDCl$_3$): δ 7.28 (br s, 1H) 7.19-7.12 (m, 3H), 3.39 (s, 2H), 2.82 (t, 4H, J=5.6 Hz), 2.34 (br s, 4H), 1.54 (br s, 1H). $^{13}$C-NMR (100 MHz, CDCl$_3$): δ 140.2, 133.9, 129.2, 128.8, 127.0, 126.9, 62.8, 54.3, 45.9.

Ethyl 2-(4-(3-chlorobenzyl)piperazin-1-yl)acetate (6{8})

Synthesized according to General Procedure B: 5{8} (5.22 g, 24.7 mmol, 1 equiv.), ethyl chloroacetate (2.90 mL, 27.1 mmol, 1.1 equiv.), NaHCO$_3$ (2.59 g, 30.8 mmol, 1.25 equiv.), acetone (49.4 mL). Purification with flash column chromatography on silica gel (1:1 hexanes:EtOAc) afforded 6{8} (6.84 g, 93%) as a yellow liquid. $^1$H-NMR (400 MHz, CDCl$_3$): δ 7.30 (br s, 1H) 7.21-7.15 (m, 3H), 4.16 (q, 2H, J=7.2 Hz) 3.46 (s, 2H), 3.18 (s, 2H), 2.58 (br s, 4H), 2.49 (br s, 4H), 1.24 (t, 3H, 7.2 Hz). $^{13}$C-NMR (100 MHz, CDCl$_3$): δ 170.2, 140.2, 134.0, 129.3, 128.9, 127.1, 127.1, 62.2, 60.5, 59.4, 52.9, 52.7, 14.2.

2-(4-(3-chlorobenzyl)piperazin-1-yl)acetohydrazide (1{8})

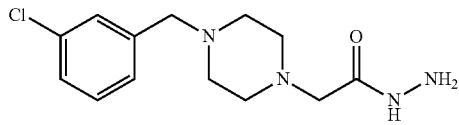 [SMILES: NNC(=O)CN1CCN(Cc2cccc(Cl)c2)CC1]

Synthesized according to General Procedure C: 6{8} (6.78 g, 22.8 mmol, 1 equiv.), anhydrous hydrazine (2.9 mL, 91.4 mmol, 4 equiv.), ethanol (31.4 mL). Purification by silica gel column chromatography (4:1 EtOAc:MeOH) afforded 1{8} (5.04 g, 78%) as a light yellow oil. $^1$H-NMR (500 MHz, CDCl$_3$): δ 8.15 (br s, 1H), 7.27 (br s, 1H) 7.21-7.12 (m, 3H), 3.82 (br s, 2H) 3.42 (s, 2H), 3.03 (s, 2H), 2.49 (br s, 4H), 2.41 (br s, 4H). $^{13}$C-NMR (125 MHz, CDCl$_3$): δ 170.3, 140.0, 134.0, 129.3, 128.8, 127.1, 126.9, 62.0, 60.4, 53.4, 52.8.

1-(4-bromobenzyl)piperazine (5{9})

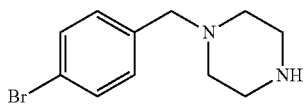 [SMILES: Brc1ccc(CN2CCNCC2)cc1]

Synthesized according to General Procedure A: 4-bromobenzyl bromide (4{9}, 7 g, 28.0 mmol, 1 equiv.), piperazine (14.5 g, 168.0 mmol, 6 equiv.), THF (61.2 mL). Purification with flash column chromatography on silica gel (4:1 EtOAc:MeOH) afforded 5{9} (6.73 g, 94%) as a white solid. $^1$H-NMR (400 MHz, CDCl$_3$): δ 7.42 (d, 2H, J=8.4 Hz) 7.19 (d, 2H, J=8.4 Hz), 3.42 (s, 2H) 2.87 (t, 4H, J=4.8 Hz), 2.38 (br s, 4H), 2.07 (br s, 1H). $^{13}$C-NMR (100 MHz, CDCl$_3$): δ 137.1, 131.3, 130.9, 120.8, 62.8, 54.2, 45.9.

Ethyl 2-(4-(4-bromobenzyl)piperazin-1-yl)acetate (6{9})

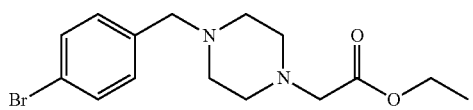 [SMILES: CCOC(=O)CN1CCN(Cc2ccc(Br)cc2)CC1]

Synthesized according to General Procedure B: 5{9} (6.39 g, 25.0 mmol, 1 equiv.), ethyl chloroacetate (2.9 mL, 27.5 mmol, 1.1 equiv.), NaHCO$_3$ (2.63 g, 31.3 mmol, 1.25 equiv.), acetone (50 mL). Purification with flash column chromatography on silica gel (1:1 hexanes:EtOAc) afforded 6{9} (6.56 g, 77%) as a beige solid. $^1$H-NMR (500 MHz, CDCl$_3$): δ 7.41 (d, 2H, J=8.0 Hz) 7.18 (d, 2H, J=8.5 Hz), 4.16 (q, 2H, J=7.0 Hz), 3.44 (s, 2H) 3.18 (s, 2H), 2.58 (br s, 4H), 2.49 (br s, 4H), 1.25 (t, 3H, J=7.0 Hz). $^{13}$C-NMR (125 MHz, CDCl$_3$): δ 170.2, 137.1, 131.2, 130.7, 120.7, 62.1, 60.5, 59.4, 52.9, 52.7, 14.2.

2-(4-(4-bromobenzyl)piperazin-1-yl)acetohydrazide (1{9})

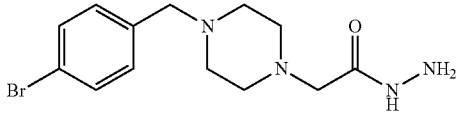 [SMILES: NNC(=O)CN1CCN(Cc2ccc(Br)cc2)CC1]

Synthesized according to General Procedure C: 6{9} (6.23 g, 18.3 mmol, 1 equiv.), anhydrous hydrazine (2.3 mL, 73.1 mmol, 4 equiv.), ethanol (25.2 mL). Purification by silica gel column chromatography (4:1 EtOAc:MeOH) afforded 1{9} (4.64 g, 78%) as a white solid. $^1$H-NMR (500 MHz, CDCl$_3$): δ 8.13 (br s, 1H), 7.39 (d, 2H, J=8.5 Hz) 7.15 (d, 2H, J=8.5 Hz), 3.83 (br s, 2H), 3.41 (s, 2H) 3.04 (s, 2H), 2.49 (br s, 4H), 2.41 (br s, 4H). $^{13}$C-NMR (125 MHz, CDCl$_3$): δ 170.3, 136.9, 131.2, 130.5, 120.8, 61.9, 60.4, 53.5, 52.9.

1-(3,4-bis(benzyloxy)benzyl)piperazine (5{10})

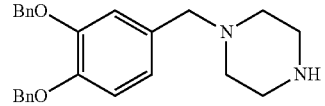 [SMILES: c1ccc(COc2ccc(CN3CCNCC3)cc2OCc2ccccc2)cc1]

Synthesized according to General Procedure A: 3,4-bis(benzyloxy)benzyl chloride (4{10}, 2 g, 5.90 mmol, 1 equiv.), piperazine (3.05 g, 35.4 mmol, 6 equiv.), THF (28 mL). Purification with flash column chromatography on silica gel (gradient, 4:1 to 1:4 EtOAc:MeOH) afforded 5{10} (2.12 g, 92%) as a beige solid. $^1$H-NMR (500 MHz, CDCl$_3$): δ 7.46 (d, 4H, J=7.5 Hz), 7.38-7.34 (m, 4H) 7.32-7.28 (m, 2H), 6.96 (d, 1H, J=2.0 Hz), 6.88 (d, 1H, J=8.0 Hz), 6.80 (dd, 1H, J=2.0, 8.0 Hz), 5.18 (s, 2H), 5.15 (s, 2H), 3.38 (s, 2H), 2.84 (t, 4H, J=5.0 Hz), 2.33 (br s, 4H), 1.74 (br s, 1H). $^{13}$C-NMR (125 MHz, CDCl$_3$): δ 148.5, 147.9, 137.4, 137.3, 131.3, 128.4, 128.3, 127.6, 127.6, 127.3, 127.2, 122.0, 116.1, 114.6, 71.3, 71.1, 63.1, 54.3, 46.0.

Ethyl 2-(4-(3,4-bis(benzyloxy)benzyl)piperazin-1-yl)acetate (6{10})

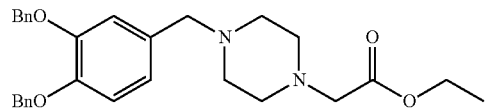 [SMILES: CCOC(=O)CN1CCN(Cc2ccc(OCc3ccccc3)c(OCc3ccccc3)c2)CC1]

Synthesized according to General Procedure B: 5{10} (2.07 g, 5.33 mmol, 1 equiv.), ethyl chloroacetate (0.63 mL, 5.87 mmol, 1.1 equiv.), NaHCO$_3$ (0.56 g, 6.67 mmol, 1.25 equiv.), acetone (10.7 mL), chloroform (15.0 mL). Purification with flash column chromatography on silica gel (1:1 hexanes:EtOAc) afforded 6{10} (2.10 g, 83%) as a beige solid. $^1$H-NMR (500 MHz, CDCl$_3$): δ 7.45 (d, 4H, J=7.5 Hz), 7.37-7.34 (m, 4H) 7.31-7.28 (m, 2H), 6.95 (d, 1H, J=1.5 Hz), 6.88 (d, 1H, J=8.0 Hz), 6.79 (dd, 1H, J=1.5, 8.0 Hz), 5.17 (s, 2H), 5.14 (s, 2H), 4.19 (q, 2H, J=7.0 Hz), 3.41 (s, 2H), 3.20 (s, 2H), 2.56 (br s, 4H), 2.45 (br s, 4H), 1.27 (t, 3H, J=7.0 Hz). ¹³C-NMR (125 MHz, CDCl₃): δ 170.2, 148.5, 148.0, 137.4, 137.3, 131.3, 128.3, 128.3, 127.6, 127.6, 127.3, 127.2, 122.0, 116.0, 114.6, 71.2, 71.1, 62.4, 60.5, 59.4, 53.0, 52.5, 14.2.

2-(4-(3,4-bis(benzyloxy)benzyl)piperazin-1-yl)acetohydrazide (1{10})

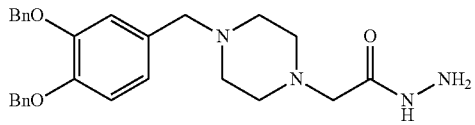 [SMILES: NNC(=O)CN1CCN(Cc2ccc(OCc3ccccc3)c(OCc3ccccc3)c2)CC1]

Synthesized according to General Procedure C: 6{10} (2.02 g, 4.26 mmol, 1 equiv.), anhydrous hydrazine (0.40 mL, 12.8 mmol, 3 equiv.), ethanol (8.6 mL). Purification by silica gel column chromatography (4:1 EtOAc:MeOH) afforded 1{10} (3.00 g, 81%) as a white solid. ¹H-NMR (500 MHz, CDCl₃): δ 8.13 (br s, 1H), 7.45-7.44 (m, 4H), 7.37-7.33 (m, 4H) 7.31-7.27 (m, 2H), 6.92 (d, 1H, J=2.0 Hz), 6.87 (d, 1H, J=8.0 Hz), 6.77 (dd, 1H, J=2.0, 8.0 Hz), 5.17 (s, 2H), 5.15 (s, 2H), 3.84 (br s, 2H), 3.39 (s, 2H), 3.06 (s, 2H), 2.48 (br s, 4H), 2.37 (br s, 4H). ¹³C-NMR (125 MHz, CDCl₃): δ 170.5, 148.6, 148.1, 137.3, 137.3, 131.1, 128.4, 128.3, 127.7, 127.6, 127.3, 127.2, 122.0, 116.0, 114.6, 71.3, 71.1, 62.3, 60.5, 53.6, 52.8.

1-(3-phenoxybenzyl)piperazine (5{11})

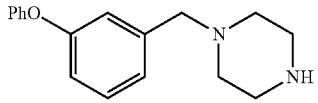 [SMILES: c1ccc(Oc2cccc(CN3CCNCC3)c2)cc1]

Synthesized according to General Procedure A: 3-phenoxybenzyl chloride (4{11}, 5 g, 22.9 mmol, 1 equiv.), piperazine (11.8 g, 137.2 mmol, 6 equiv.), THF (6.14 mL). Purification with flash column chromatography on silica gel (gradient, 4:1 to 1:4 EtOAc:MeOH) afforded 5{11} (5.72 g, 93%) as a light yellow oil. ¹H-NMR (500 MHz, CDCl₃): δ 7.35-7.32 (m, 2H) 7.28 (d, 1H, J=8.5 Hz), 7.12-7.08 (m, 2H), 7.05 (br s, 1H), 7.02 (d, 2H, J=8.0 Hz), 6.90 (dd, 1H, J=2.0, 8.0 Hz), 3.48 (s, 2H), 2.88 (t, 4H, J=5.0 Hz), 2.42 (br s, 4H), 1.66 (br s, 1H). ¹³C-NMR (125 MHz, CDCl₃): δ 157.2, 156.9, 140.2, 129.5, 129.2, 123.8, 122.9, 119.5, 118.5, 117.3, 63.1, 54.3, 45.9.

Ethyl 2-(4-(3-phenoxybenzyl)piperazin-1-yl)acetate (6{11})

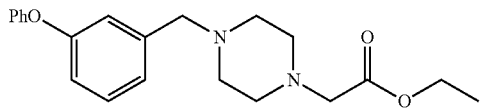 [SMILES: CCOC(=O)CN1CCN(Cc2cccc(Oc3ccccc3)c2)CC1]

Synthesized according to General Procedure B: 5{11} (5.44 g, 20.3 mmol, 1 equiv.), ethyl chloroacetate (2.4 mL, 22.3 mmol, 1.1 equiv.), NaHCO₃ (2.13 g, 25.3 mmol, 1.25 equiv.), acetone (40.6 mL). Purification with flash column chromatography on silica gel (1:1 hexanes:EtOAc) afforded 6{11} (6.50 g, 91%) as an orange oil. ¹H-NMR (500 MHz, CDCl₃): δ 7.29 (t, 2H, J=8.0 Hz) 7.23 (t, 1H, J=8.0 Hz), 7.07-7.03 (m, 2H), 7.00 (br s, 1H), 6.97 (d, 2H, J=8.0 Hz), 6.85 (dd, 1H, J=2.0, 8.0 Hz), 4.15 (q, 2H, J=7.0 Hz), 3.47 (s, 2H), 3.17 (s, 2H), 2.57 (br s, 4H), 2.50 (br s, 4H), 1.24 (t, 3H, J=7.0 Hz). ¹³C-NMR (125 MHz, CDCl₃): δ 170.0, 157.1, 156.9, 140.1, 129.5, 129.2, 123.8, 122.9, 119.4, 118.5, 117.3, 62.3, 60.3, 59.3, 52.8, 52.5, 14.1.

2-(4-(3-phenoxybenzyl)piperazin-1-yl)acetohydrazide (1{11})

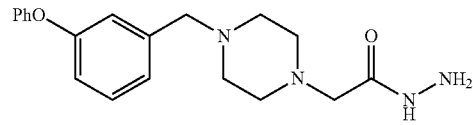 [SMILES: NNC(=O)CN1CCN(Cc2cccc(Oc3ccccc3)c2)CC1]

Synthesized according to General Procedure C: 6{11} (6.28 g, 17.7 mmol, 1 equiv.), anhydrous hydrazine (1.7 mL, 53.1 mmol, 3 equiv.), ethanol (35.6 mL). Purification by silica gel column chromatography (gradient, 4:1 to 3:2 EtOAc:MeOH) afforded 1{11} (5.11 g, 85%) as a light yellow oil. ¹H-NMR (500 MHz, CDCl₃): δ 8.14 (br s, 1H), 7.32 (t, 2H, J=8.0 Hz) 7.26 (t, 1H, J=8.0 Hz), 7.09 (t, 1H, J=7.5 Hz), 7.04 (d, 1H, J=7.5 Hz), 7.00-6.98 (m, 3H), 6.88 (dd, 1H, J=2.0, 8.0 Hz), 3.84 (br s, 2H), 3.48 (s, 2H), 3.06 (s, 2H), 2.52 (br s, 4H), 2.45 (br s, 4H). ¹³C-NMR (125 MHz, CDCl₃): δ 170.4, 157.2, 157.1, 140.1, 129.6, 129.4, 123.8, 123.1, 119.4, 118.7, 117.5, 62.4, 60.5, 53.6, 52.9.

1-([1,1'-biphenyl]-2-ylmethyl)piperazine (5{12})

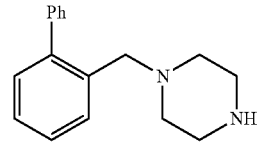 [SMILES: c1ccc(-c2ccccc2CN2CCNCC2)cc1]

Synthesized according to General Procedure A: 2-phenylbenzyl bromide (4{12}, 5 g, 20.2 mmol, 1 equiv.), piperazine (10.5 g, 121.4 mmol, 6 equiv.), THF (44.2 mL). Purification with flash column chromatography on silica gel (4:1 EtOAc:MeOH) afforded 5{12} (3.92 g, 77%) as a white solid. ¹H-NMR (500 MHz, CDCl₃): δ 7.55 (dd, 1H, J=1.5, 7.0 Hz), 7.42-7.38 (m, 4H) 7.36-7.32 (m, 2H), 7.30 (dd, 1H, J=1.5, 7.0 Hz), 7.27 (dd, 1H, J=1.5, 7.0 Hz), 3.40 (s, 2H), 2.83 (t, 4H, J=5.0 Hz), 2.33 (br s, 4H), 1.58 (br s, 1H). ¹³C-NMR (125 MHz, CDCl₃): δ 142.6, 141.4, 135.5, 129.9, 129.8, 129.4, 127.8, 126.9, 126.7, 126.6, 60.3, 54.1, 46.1.

Ethyl 2-(4-([1,1'-biphenyl]-2-ylmethyl)piperazin-1-yl)acetate (6{12})

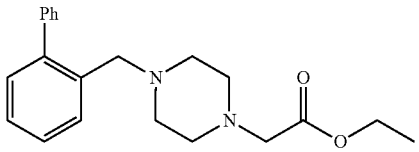 [SMILES: CCOC(=O)CN1CCN(Cc2ccccc2-c2ccccc2)CC1]

Synthesized according to General Procedure B: 5{12} (3.79 g, 15.0 mmol, 1 equiv.), ethyl chloroacetate (1.8 mL, 16.5 mmol, 1.1 equiv.), NaHCO$_3$ (1.58 g, 18.8 mmol, 1.25 equiv.), acetone (30.0 mL). Purification with flash column chromatography on silica gel (1:1 hexanes:EtOAc) afforded 6{12} (4.57 g, 90%) as an orange oil. $^1$H-NMR (500 MHz, CDCl$_3$): δ 7.51 (dd, 1H, J=2.0, 7.0 Hz), 7.39-7.36 (m, 4H) 7.35-7.28 (m, 3H), 7.26 (dd, 1H, J=2.0, 7.0 Hz), 4.17 (q, 2H, J=7.0 Hz), 3.42 (s, 2H), 3.17 (s, 2H), 2.54 (br s, 4H), 2.44 (br s, 4H), 1.26 (t, 3H, J=7.0 Hz). $^{13}$C-NMR (125 MHz, CDCl$_3$): δ 170.2, 142.7, 141.3, 135.5, 130.0, 130.0, 129.5, 127.7, 127.0, 126.7, 60.5, 59.6, 59.5, 53.1, 52.4, 14.2.

2-(4-([1,1'-biphenyl]-2-ylmethyl)piperazin-1-yl)acetohydrazide (1{12})

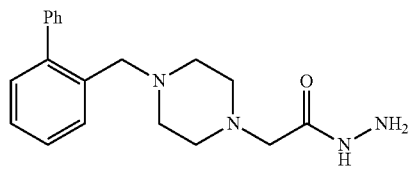

Synthesized according to General Procedure C: 6{12} (4.34 g, 13.4 mmol, 1 equiv.), anhydrous hydrazine (1.3 mL, 40.1 mmol, 3 equiv.), ethanol (27.0 mL). Purification by silica gel column chromatography (4:1 EtOAc:MeOH) afforded 1{12} (4.02 g, 93%) as a beige solid. $^1$H-NMR (500 MHz, CDCl$_3$): δ 8.12 (br s, 1H), 7.50 (dd, 1H, J=2.0, 7.0 Hz), 7.41-7.34 (m, 5H) 7.33-7.29 (m, 2H), 7.26-7.24 (m, 1H), 3.83 (br s, 2H), 3.40 (s, 2H), 3.04 (s, 2H), 2.47 (br s, 4H), 2.36 (br s, 4H). $^{13}$C-NMR (125 MHz, CDCl$_3$): δ 170.4, 142.6, 141.3, 135.3, 130.0, 129.8, 129.4, 127.8, 127.0, 126.8, 60.5, 59.5, 53.7, 52.7.

1-(4-methylbenzyl)piperazine (5{13})

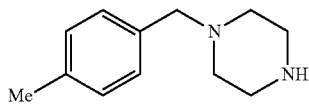 [SMILES: Cc1ccc(CN2CCNCC2)cc1]

Synthesized according to General Procedure A: 4-methylbenzyl chloride (4{13}, 6.1 mL, 46.2 mmol, 1 equiv.), piperazine (23.9 g, 277.4 mmol, 6 equiv.), THF (100.9 mL). Purification with flash column chromatography on silica gel (4:1 EtOAc:MeOH) afforded 5{13} (6.56 g, 96%) as a white solid. $^1$H-NMR (500 MHz, CDCl$_3$): δ 7.18 (d, 2H, J=8.0 Hz), 7.09 (d, 2H, J=7.5 Hz), 3.42 (s, 2H), 2.84 (t, 4H, J=5.0 Hz), 2.37 (br s, 4H), 2.31 (s, 3H), 1.54 (br s, 1H). $^{13}$C-NMR (125 MHz, CDCl$_3$): δ 136.3, 134.7, 129.0, 128.6, 63.2, 54.3, 45.9, 20.9.

Ethyl 2-(4-(4-methylbenzyl)piperazin-1-yl)acetate (6{13})

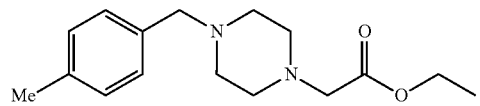 [SMILES: CCOC(=O)CN1CCN(Cc2ccc(C)cc2)CC1]

Synthesized according to General Procedure B: 5{13} (8.27 g, 43.4 mmol, 1 equiv.), ethyl chloroacetate (5.1 mL, 47.8 mmol, 1.1 equiv.), NaHCO$_3$ (4.56 g, 54.3 mmol, 1.25 equiv.), acetone (86.8 mL). Purification with flash column chromatography on silica gel (1:1 hexanes:EtOAc) afforded 6{13} (8.92 g, 74%) as an orange liquid. $^1$H-NMR (400 MHz, CDCl$_3$): δ 7.16 (d, 2H, J=8.0 Hz), 7.07 (d, 2H, J=8.0 Hz), 4.13 (q, 2H, J=7.2 Hz), 3.43 (s, 2H), 3.15 (s, 2H), 2.55 (br s, 4H), 2.48 (br s, 4H), 2.28 (s, 3H), 1.22 (t, 3H, J=7.2 Hz). $^{13}$C-NMR (100 MHz, CDCl$_3$): δ 170.0, 136.3, 134.6, 128.7, 62.4, 60.3, 59.2, 52.8, 52.4, 20.9, 14.0.

2-(4-(4-methylbenzyl)piperazin-1-yl)acetohydrazide (1{13})

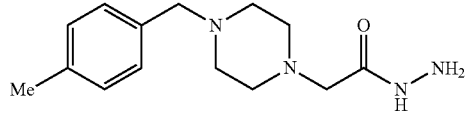 [SMILES: Cc1ccc(CN2CCN(CC(=O)NN)CC2)cc1]

Synthesized according to General Procedure C: 6{13} (7.66 g, 27.7 mmol, 1 equiv.), anhydrous hydrazine (2.6 mL, 83.2 mmol, 3 equiv.), ethanol (55.4 mL). Purification by silica gel column chromatography (4:1 EtOAc:MeOH) afforded 1{13} (6.10 g, 84%) as a beige solid. $^1$H-NMR (500 MHz, CDCl$_3$): δ 8.14 (br s, 1H), 7.18 (d, 2H, J=8.0 Hz), 7.12 (d, 2H, J=8.0 Hz), 3.84 (br s, 2H), 3.46 (s, 2H), 3.06 (s, 2H), 2.52 (br s, 4H), 2.45 (br s, 4H), 2.33 (s, 3H). $^{13}$C-NMR (125 MHz, CDCl$_3$): δ 170.5, 136.7, 134.6, 129.1, 128.9, 62.5, 60.5, 53.6, 52.9, 21.1.

1-(2,3,4,5,6-pentamethylbenzyl)piperazine (5{14})

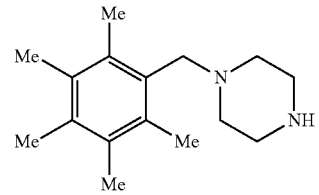 [SMILES: Cc1c(C)c(C)c(CN2CCNCC2)c(C)c1C]

Synthesized according to General Procedure A: 2,3,4,5,6-pentamethylbenzyl chloride (4{14}, 5 g, 25.4 mmol, 1 equiv.), piperazine (13.1 g, 152.5 mmol, 6 equiv.), THF (55.5 mL). Purification with flash column chromatography on silica gel (4:1 EtOAc:MeOH) afforded 5{14} (5.31 g, 85%) as a white solid. $^1$H-NMR (400 MHz, CDCl$_3$): δ 3.52 (s, 2H), 2.80 (t, 4H, J=4.8 Hz), 2.45 (br s, 4H), 2.32 (s, 6H), 2.25 (s, 3H), 2.23 (s, 6H), 1.63 (br s, 1H). $^{13}$C-NMR (125 MHz, CDCl$_3$): δ 133.9, 133.7, 132.3, 131.9, 57.2, 54.1, 46.5, 17.0, 16.8, 16.6.

Ethyl 2-(4-(2,3,4,5,6-pentamethylbenzyl)piperazin-1-yl)acetate (6{14})

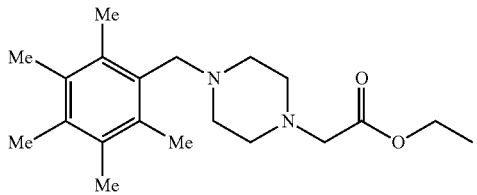 [SMILES: CCOC(=O)CN1CCN(Cc2c(C)c(C)c(C)c(C)c2C)CC1]

Synthesized according to General Procedure B: 5{14} (1.95 g, 7.92 mmol, 1 equiv.), ethyl chloroacetate (0.94 mL, 8.71 mmol, 1.1 equiv.), NaHCO$_3$ (0.83 g, 9.90 mmol, 1.25 equiv.), acetone (52 mL), chloroform (10 mL). Purification with flash column chromatography on silica gel (1:1 hexanes:EtOAc) afforded 6{14} (2.50 g, 95%) as a light yellow solid. $^1$H-NMR (400 MHz, CDCl$_3$): δ 4.21 (q, 4H, J=7.2 Hz), 3.58 (s, 2H), 3.20 (s, 2H), 2.59 (br s, 8H), 2.33 (s, 6H), 2.27 (s, 3H), 2.25 (s, 6H), 1.29 (t, 3H, J=7.2 Hz). $^{13}$C-NMR (100 MHz, CDCl$_3$): δ 170.3, 133.8, 133.7, 132.2, 131.8, 60.4, 59.5, 56.4, 53.4, 52.2, 17.0, 16.7, 16.5, 14.2.

2-(4-(2,3,4,5,6-pentamethylbenzyl)piperazin-1-yl)acetohydrazide (1{14})

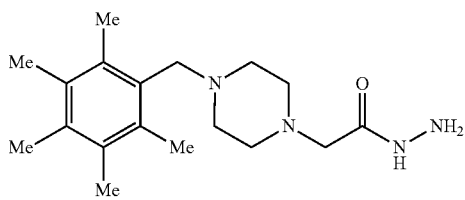 [SMILES: Cc1c(C)c(C)c(CN2CCN(CC(=O)NN)CC2)c(C)c1C]

Synthesized according to General Procedure C: 6{14} (2.40 g, 7.23 mmol, 1 equiv.), anhydrous hydrazine (0.68 mL, 21.7 mmol, 3 equiv.), ethanol (14.5 mL). Recrystallization from EtOH afforded 1{14} (1.88 g, 82%) as a light yellow crystalline solid. $^1$H-NMR (500 MHz, CDCl$_3$): δ 8.19 (br s, 1H), 3.85 (d, 2H, J=5.0 Hz), 3.55 (s, 2H), 3.05 (s, 2H), 2.47 (br s, 8H), 2.30 (s, 6H), 2.25 (s, 3H), 2.23 (s, 6H). $^{13}$C-NMR (125 MHz, CDCl$_3$): δ 170.7, 133.9, 133.9, 132.4, 131.6, 60.6, 56.4, 54.0, 52.5, 17.0, 16.8, 16.6.

1-(4-(trifluoromethyl)benzyl)piperazine (5{15})

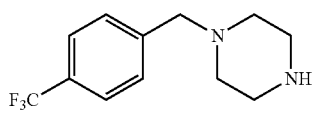

Synthesized according to General Procedure A: 4-trifluoromethylbenzyl chloride (4{15}, 5 g, 25.7 mmol, 1 equiv.), piperazine (13.3 g, 154.2 mmol, 6 equiv.), THF (56.1 mL). Purification with flash column chromatography on silica gel (4:1 EtOAc:MeOH) afforded 5{15} (3.97 g, 67%) as a light yellow liquid. $^1$H-NMR (400 MHz, CDCl$_3$): δ 7.52 (d, 2H, J=8.0 Hz), 7.40 (d, 2H, J=8.0 Hz), 3.48 (s, 2H), 2.84 (t, 4H, J=4.8 Hz), 2.36 (br s, 4H), 1.55 (br s, 1H). $^{13}$C-NMR (100 MHz, CDCl$_3$): δ 142.4, 129.1 (q, J$_{C-F}$=32.1 Jz) 129.1 (br), 125.0 (br), 124.1 (q, J$_{C-F}$=338.0 Hz), 62.9, 54.4, 45.9. $^{19}$F-NMR (375 MHz, CDCl$_3$): δ −62.5.

Ethyl 2-(4-(4-(trifluoromethyl)benzyl)piperazin-1-yl)acetate (6{15})

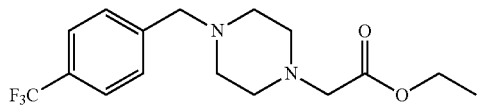 [SMILES: CCOC(=O)CN1CCN(Cc2ccc(C(F)(F)F)cc2)CC1]

Synthesized according to General Procedure B: 5{15} (3.85 g, 16.6 mmol, 1 equiv.), ethyl chloroacetate (2.0 mL, 18.3 mmol, 1.1 equiv.), NaHCO$_3$ (1.74 g, 20.7 mmol, 1.25 equiv.), acetone (33.2 mL). Purification with flash column chromatography on silica gel (1:1 hexanes:EtOAc) afforded 6{15} (4.89 g, 89%) as a yellow liquid. $^1$H-NMR (500 MHz, CDCl$_3$): δ 7.53 (d, 2H, J=8.0 Hz), 7.41 (d, 2H, J=8.0 Hz), 4.15 (q, 2H, J=7.0 Hz), 3.53 (s, 2H), 3.18 (s, 2H), 2.58 (br s, 4H), 2.50 (br s, 4H), 1.24 (t, 3H, J=7.0 Hz). $^{13}$C-NMR (125 MHz, CDCl$_3$): δ 170.1, 142.4, 129.2 (q, J$_{C-F}$=32.1 Hz), 129.1, 125.0 (q, J$_{C-F}$=3.8 Hz), 124.1 (q, J$_{C-F}$=270.8 Hz), 62.2, 60.5, 59.3, 52.9, 52.7, 14.1. $^{19}$F-NMR (375 MHz, CDCl$_3$): δ −62.8.

2-(4-(4-(trifluoromethyl)benzyl)piperazin-1-yl)acetohydrazide (1{15})

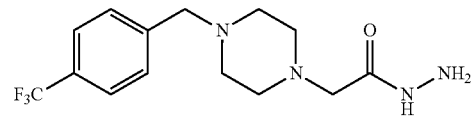 [SMILES: NNC(=O)CN1CCN(Cc2ccc(C(F)(F)F)cc2)CC1]

Synthesized according to General Procedure C: 6{15} (4.76 g, 14.4 mmol, 1 equiv.), anhydrous hydrazine (1.4 mL, 43.2 mmol, 3 equiv.), ethanol (28.9 mL). Purification by silica gel column chromatography (4:1 EtOAc:MeOH) afforded 1{15} (3.70 g, 81%) as a white solid. $^1$H-NMR (500 MHz, CDCl$_3$): δ 8.13 (br s, 1H), 7.55 (d, 2H, J=8.0 Hz), 7.41 (d, 2H, J=8.0 Hz), 3.84 (br s, 2H), 3.53 (s, 2H), 3.07 (s, 2H), 2.53 (br s, 4H), 2.45 (br s, 4H). $^{13}$C-NMR (125 MHz, CDCl$_3$): δ 170.3, 142.2, 129.3 (q, J$_{C-F}$=32.0 Hz), 129.0, 125.1 (q, J$_{C-F}$=3.8 Hz), 124.1 (q, J$_{C-F}$=270.5 Hz) 129.1, 62.2, 60.5, 53.6, 53.0. $^{19}$F-NMR (470 MHz, CDCl$_3$): δ −62.8.

1-(3,4,5-trimethoxybenzyl)piperazine (5{16})

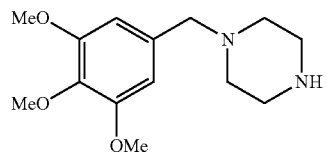 [SMILES: COc1cc(CN2CCNCC2)cc(OC)c1OC]

Synthesized according to General Procedure A: 3,4,5-trimethoxybenzyl chloride (4{16}, 5 g, 23.1 mmol, 1 equiv.), piperazine (11.9 g, 138.5 mmol, 6 equiv.), THF (50.5 mL). Purification with flash column chromatography on silica gel (4:1 EtOAc:MeOH) afforded 5{16} (5.59 g, 91%) as a white solid. ¹H-NMR (500 MHz, CDCl₃): δ 6.46 (s, 2H), 3.75 (s, 6H), 3.72 (s, 3H), 3.30 (s, 2H), 2.78 (t, 4H, J=5.0 Hz), 2.29 (br s, 4H), 1.55 (br s, 1H). ¹³C-NMR (125 MHz, CDCl₃): δ 152.7, 136.4, 133.7, 105.4, 63.6, 60.5, 55.7, 54.2, 45.8.

Ethyl 2-(4-(3,4,5-trimethoxybenzyl)piperazin-1-yl)acetate (6{16})

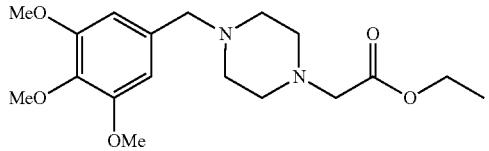 [SMILES: CCOC(=O)CN1CCN(Cc2cc(OC)c(OC)c(OC)c2)CC1]

Synthesized according to General Procedure B: 5{16} (5.47 g, 20.5 mmol, 1 equiv.), ethyl chloroacetate (2.4 mL, 22.6 mmol, 1.1 equiv.), NaHCO₃ (2.16 g, 25.7 mmol, 1.25 equiv.), acetone (41.0 mL). Purification with flash column chromatography on silica gel (1:1 hexanes:EtOAc) afforded 6{16} (6.14 g, 85%) as a brown oil. ¹H-NMR (500 MHz, CDCl₃): δ 6.50 (s, 2H), 4.12 (q, 2H, J=7.0 Hz), 3.80 (s, 6H), 3.77 (s, 3H), 3.39 (s, 2H), 3.15 (s, 2H), 2.56 (br s, 4H), 2.47 (br s, 4H), 1.21 (t, 3H, J=7.0 Hz). ¹³C-NMR (125 MHz, CDCl₃): δ 170.1, 152.8, 136.6, 133.8, 105.5, 62.9, 60.6, 60.4, 59.3, 55.9, 52.9, 52.6, 14.1.

2-(4-(3,4,5-trimethoxybenzyl)piperazin-1-yl)acetohydrazide (1{16})

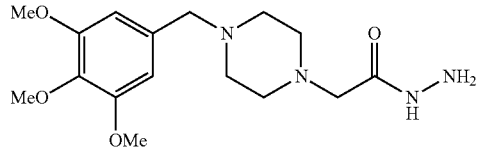 [SMILES: COc1cc(CN2CCN(CC(=O)NN)CC2)cc(OC)c1OC]

Synthesized according to General Procedure C: 6{16} (5.99 g, 17.0 mmol, 1 equiv.), anhydrous hydrazine (1.6 mL, 51.0 mmol, 3 equiv.), ethanol (34.2 mL). Purification by silica gel column chromatography (4:1 EtOAc:MeOH) afforded 1{16} (4.93 g, 86%) as a white solid. ¹H-NMR (500 MHz, CDCl₃): δ 8.14 (br s, 1H), 6.47 (s, 2H), 3.83 (br s, 2H), 3.78 (s, 6H), 3.76 (s, 3H), 3.36 (s, 2H), 3.01 (s, 2H), 2.48 (br s, 4H), 2.39 (br s, 4H). ¹³C-NMR (125 MHz, CDCl₃): δ 170.2, 152.8, 136.6, 133.6, 105.4, 62.8, 60.6, 60.4, 55.9, 53.4, 52.8.

1-(4-(trifluoromethoxy)benzyl)piperazine (5{17})

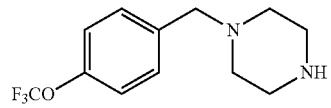

Synthesized according to General Procedure A: 4-trifluoromethoxybenzyl bromide (4{17}, 5 g, 19.6 mmol, 1 equiv.), piperazine (10.1 g, 117.6 mmol, 6 equiv.), THF (42.8 mL). Purification with flash column chromatography on silica gel (4:1 EtOAc:MeOH) afforded 5{17} (4.75 g, 93%) as a yellow liquid. ¹H-NMR (500 MHz, CDCl₃): δ 7.28 (d, 2H, J=8.0 Hz), 7.08 (d, 2H, J=8.0 Hz), 3.40 (s, 2H), 2.81 (t, 4H, J=5.0 Hz), 2.33 (br s, 4H), 1.51 (br s, 1H). ¹³C-NMR (125 MHz, CDCl₃): δ 148.0, 136.9, 130.1, 120.5, 120.3 (q, J_{C-F}=255.5 Hz), 62.6, 54.3, 45.9. ¹⁹F-NMR (375 MHz, CDCl₃): −58.4.

Ethyl 2-(4-(4-(trifluoromethoxy)benzyl)piperazin-1-yl)acetate (6{17})

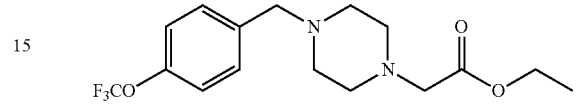

Synthesized according to General Procedure B: 5{17} (4.15 g, 17.8 mmol, 1 equiv.), ethyl chloroacetate (2.1 mL, 19.6 mmol, 1.1 equiv.), NaHCO₃ (1.87 g, 22.3 mmol, 1.25 equiv.), acetone (35.6 mL). Purification with flash column chromatography on silica gel (1:1 hexanes:EtOAc) afforded 6{17} (5.64 g, 92%) as an orange liquid. ¹H-NMR (500 MHz, CDCl₃): δ 7.28 (d, 2H, J=8.0 Hz), 7.09 (d, 2H, J=8.0 Hz), 4.12 (q, 2H, J=7.0 Hz), 3.45 (s, 2H), 3.11 (s, 2H), 2.55 (br s, 4H), 2.46 (br s, 4H), 1.20 (t, 3H, J=7.0 Hz). ¹³C-NMR (125 MHz, CDCl₃): δ 170.0, 148.0, 136.8, 130.1, 120.5, 120.3 (q, J_{C-F}=255.5 Hz), 61.8, 60.4, 59.3, 52.8, 52.6, 14.0. ¹⁹F-NMR (470 MHz, CDCl₃): −58.4.

2-(4-(4-(trifluoromethoxy)benzyl)piperazin-1-yl)acetohydrazide (1{17})

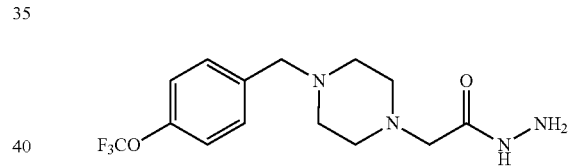

Synthesized according to General Procedure C: 6{17} (5.57 g, 16.1 mmol, 1 equiv.), anhydrous hydrazine (1.5 mL, 48.3 mmol, 3 equiv.), ethanol (32.4 mL). Purification by silica gel column chromatography (4:1 EtOAc:MeOH) afforded 1{17} (4.67 g, 87%) as a beige solid. ¹H-NMR (500 MHz, CDCl₃): δ 8.15 (br s, 1H), 7.28 (d, 2H, J=8.0 Hz), 7.11 (d, 2H, J=8.0 Hz), 3.83 (br s, 2H), 3.45 (s, 2H), 3.03 (s, 2H), 2.49 (br s, 4H), 2.41 (br s, 4H). ¹³C-NMR (125 MHz, CDCl₃): δ 170.3, 148.1, 136.7, 130.1, 120.5, 120.3 (q, J_{C-F}=255.5 Hz), 61.8, 60.4, 53.5, 52.9. ¹⁹F-NMR (470 MHz, CDCl₃): −58.3.

1-(4-(benzyloxy)benzyl)piperazine (5{18})

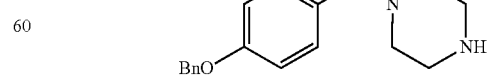

Synthesized according to General Procedure A: 4-benzyloxybenzyl chloride (4{18}, 3.7 g, 15.9 mmol, 1 equiv.), piperazine (8.22 g, 95.4 mmol, 6 equiv.), THF (55 mL). Purification with flash column chromatography on silica gel (4:1 EtOAc:MeOH) afforded 5{18} (3.84 g, 86%) as a white solid. $^1$H-NMR (500 MHz, CDCl$_3$): δ 7.43 (d, 2H, J=7.0 Hz), 7.38 (t, 2H, J=7.5 Hz), 7.32 (t, 1H, J=7.5 Hz), 7.23 (d, 2H, J=8.5 Hz), 6.93 (d, 2H, J=8.5 Hz), 5.04 (s, 2H), 3.43 (s, 2H), 2.87 (t, 4H, J=5.0 Hz), 2.39 (br s, 4H), 1.59 (br s, 1H). $^{13}$C-NMR (125 MHz, CDCl$_3$): δ 157.8, 137.0, 130.3, 128.4, 127.8, 127.3, 114.4, 69.9, 63.0, 54.3, 46.0.

Ethyl 2-(4-(4-(benzyloxy)benzyl)piperazin-1-yl)acetate (6{18})

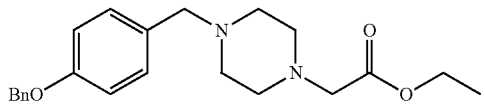 [SMILES: CCOC(=O)CN1CCN(Cc2ccc(OCc3ccccc3)cc2)CC1]

Synthesized according to General Procedure B: 5{18} (3.81 g, 13.5 mmol, 1 equiv.), ethyl chloroacetate (1.6 mL, 14.8 mmol, 1.1 equiv.), NaHCO$_3$ (1.42 g, 16.9 mmol, 1.25 equiv.), acetone (27.0 mL). Purification with flash column chromatography on silica gel (1:1 hexanes:EtOAc) afforded 6{18} (3.85 g, 79%) as a beige solid. $^1$H-NMR (500 MHz, CDCl$_3$): δ 7.42 (d, 2H, J=7.0 Hz), 7.37 (t, 2H, J=7.0 Hz), 7.31 (t, 1H, J=7.0 Hz), 7.22 (d, 2H, J=8.0 Hz), 6.92 (d, 2H, J=8.5 Hz), 5.03 (s, 2H), 4.17 (q, 2H, J=7.0 Hz), 3.45 (s, 2H), 3.19 (s, 2H), 2.59 (br s, 4H), 2.51 (br s, 4H), 1.26 (t, 3H, J=7.0 Hz). $^{13}$C-NMR (125 MHz, CDCl$_3$): δ 170.1, 157.8, 136.9, 130.2, 130.2, 128.4, 127.7, 127.3, 114.3, 69.8, 62.2, 60.4, 59.4, 52.9, 52.5, 14.1.

2-(4-(4-(benzyloxy)benzyl)piperazin-1-yl)acetohydrazide (1{18})

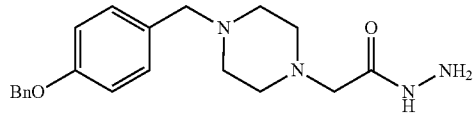 [SMILES: NNC(=O)CN1CCN(Cc2ccc(OCc3ccccc3)cc2)CC1]

Synthesized according to General Procedure C: 6{18} (3.85 g, 10.5 mmol, 1 equiv.), anhydrous hydrazine (0.99 mL, 31.4 mmol, 3 equiv.), ethanol (21.1 mL). Purification by silica gel column chromatography (4:1 EtOAc:MeOH) afforded 1{18} (3.00 g, 81%) as a white solid. $^1$H-NMR (500 MHz, CDCl$_3$): δ 8.15 (br s, 1H), 7.43 (d, 2H, J=7.0 Hz), 7.38 (t, 2H, J=7.5 Hz), 7.32 (t, 1H, J=7.5 Hz), 7.21 (d, 2H, J=8.5 Hz), 6.92 (d, 2H, J=8.5 Hz), 5.04 (s, 2H), 3.84 (br s, 2H), 3.44 (s, 2H), 3.06 (s, 2H), 2.52 (br s, 4H), 2.44 (br s, 4H). $^{13}$C-NMR (125 MHz, CDCl$_3$): δ 170.4, 157.9, 136.9, 130.2, 130.0, 128.5, 127.8, 127.4, 114.4, 69.9, 62.1, 60.5, 53.6, 52.8.

1-(4-isopropylbenzyl)piperazine (5{19})

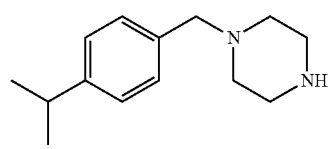 [SMILES: CC(C)c1ccc(CN2CCNCC2)cc1]

Synthesized according to General Procedure A: 4-isopropylbenzyl chloride (4{19}, 5 g, 29.6 mmol, 1 equiv.), piperazine (15.3 g, 177.9 mmol, 6 equiv.), THF (64.9 mL). Purification with flash column chromatography on silica gel (4:1 EtOAc:MeOH) afforded 5{19} (5.82 g, 90%) as a white solid. $^1$H-NMR (500 MHz, CDCl$_3$): δ 7.21 (d, 2H, J=8.0 Hz), 7.14 (d, 2H, J=8.0 Hz), 4.15 (q, 2H, J=7.0 Hz), 3.43 (s, 2H), 2.89-2.84 (m, 5H), 2.39 (br s, 4H), 2.25 (br s, 1H), 1.22 (d, 6H, J=6.5 Hz). $^{13}$C-NMR (125 MHz, CDCl$_3$): δ 147.3, 135.0, 128.9, 125.9, 63.2, 54.1, 45.7, 33.5, 23.8.

Ethyl 2-(4-(4-isopropylbenzyl)piperazin-1-yl)acetate (6{19})

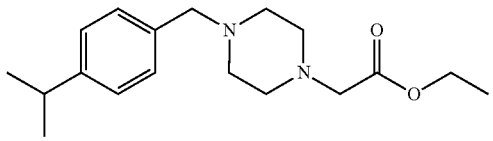 [SMILES: CCOC(=O)CN1CCN(Cc2ccc(C(C)C)cc2)CC1]

Synthesized according to General Procedure B: 5{19} (5.76 g, 26.4 mmol, 1 equiv.), ethyl chloroacetate (3.1 mL, 29.0 mmol, 1.1 equiv.), NaHCO$_3$ (2.77 g, 33.0 mmol, 1.25 equiv.), acetone (52.8 mL). Purification with flash column chromatography on silica gel (1:1 hexanes:EtOAc) afforded 6{19} (7.28 g, 90%) as an orange liquid. $^1$H-NMR (500 MHz, CDCl$_3$): δ 7.20 (d, 2H, J=8.0 Hz), 7.13 (d, 2H, J=8.5 Hz), 4.15 (q, 2H, J=7.0 Hz), 3.46 (s, 2H), 3.16 (s, 2H), 2.85 (sept, 1H, J=7.0 Hz), 2.57 (br s, 4H), 2.50 (br s, 4H), 1.23 (t, 3H, J=7.0 Hz), 1.21 (d, 6H, J=7.0 Hz). $^{13}$C-NMR (125 MHz, CDCl$_3$): δ 170.0, 147.4, 135.0, 129.0, 126.0, 62.5, 60.3, 59.3, 52.9, 52.5, 33.6, 23.9, 14.1.

2-(4-(4-isopropylbenzyl)piperazin-1-yl)acetohydrazide (1{19})

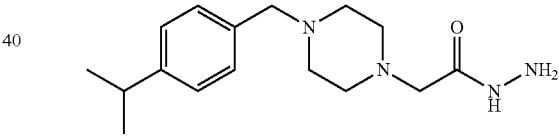

Synthesized according to General Procedure C: 6{19} (7.15 g, 23.5 mmol, 1 equiv.), anhydrous hydrazine (2.2 mL, 70.4 mmol, 3 equiv.), ethanol (47.4 mL). Purification by silica gel column chromatography (4:1 EtOAc:MeOH) afforded 1{19} (6.19 g, 91%) as a white solid. $^1$H-NMR (500 MHz, CDCl$_3$): δ 8.17 (br s, 1H), 7.19 (d, 2H, J=8.0 Hz), 7.15 (d, 2H, J=8.0 Hz), 3.81 (br s, 2H), 3.46 (s, 2H), 3.05 (s, 2H), 2.87 (sept, 1H, J=7.0 Hz), 2.51 (br s, 4H), 2.44 (br s, 4H), 1.22 (d, 6H, J=7.0 Hz). $^{13}$C-NMR (125 MHz, CDCl$_3$): δ 170.4, 147.6, 134.9, 129.0, 126.1, 62.5, 60.5, 53.5, 52.8, 33.6, 23.9.

1-(4-(tert-butyl)benzyl)piperazine (5{20})

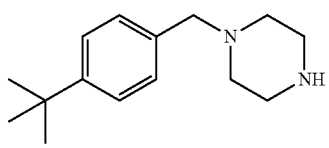 [SMILES: CC(C)(C)c1ccc(CN2CCNCC2)cc1]

Synthesized according to General Procedure A: 4-tert-butylbenzyl bromide (4{20}, 4.05 mL, 22.0 mmol, 1 equiv.), piperazine (11.4 g, 132.1 mmol, 6 equiv.), THF (48.1 mL). Purification with flash column chromatography on silica gel (4:1 EtOAc:MeOH) afforded 5{20} (3.75 g, 73%) as a beige solid. ¹H-NMR (500 MHz, CDCl₃): δ 7.30 (d, 2H, J=8.5 Hz), 7.22 (d, 2H, J=8.5 Hz), 3.44 (s, 2H), 2.85 (t, 4H, J=5.0 Hz), 2.38 (br s, 4H), 1.54 (br s, 1H), 1.29 (s, 9H). ¹³C-NMR (125 MHz, CDCl₃): δ 149.6, 134.7, 128.7, 124.8, 63.1, 54.3, 45.9, 34.2, 31.2.

Ethyl 2-(4-(4-(tert-butyl)benzyl)piperazin-1-yl)acetate (6{20})

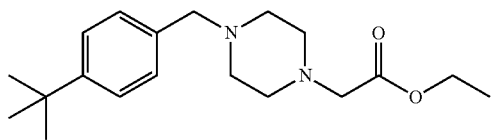 [SMILES: CCOC(=O)CN1CCN(Cc2ccc(C(C)(C)C)cc2)CC1]

Synthesized according to General Procedure B: 5{20} (3.46 g, 14.9 mmol, 1 equiv.), ethyl chloroacetate (1.8 mL, 16.4 mmol, 1.1 equiv.), NaHCO₃ (1.56 g, 18.6 mmol, 1.25 equiv.), acetone (29.8 mL), chloroform (10 mL). Purification with flash column chromatography on silica gel (1:1 hexanes:EtOAc) afforded 6{20} (4.25 g, 90%) as an orange oil. ¹H-NMR (500 MHz, CDCl₃): δ 7.31 (d, 2H, J=8.5 Hz), 7.21 (d, 2H, J=8.5 Hz), 4.16 (q, 2H, J=7.0 Hz), 3.48 (s, 2H), 3.18 (s, 2H), 2.58 (br s, 4H), 2.51 (br s, 4H), 1.29 (s, 9H), 1.24 (t, 3H, J=7.0 Hz). ¹³C-NMR (125 MHz, CDCl₃): δ 170.1, 149.7, 134.7, 128.8, 124.9, 62.5, 60.4, 59.4, 53.0, 52.6, 34.3, 31.3, 14.1.

2-(4-(4-(tert-butyl)benzyl)piperazin-1-yl)acetohydrazide (1{20})

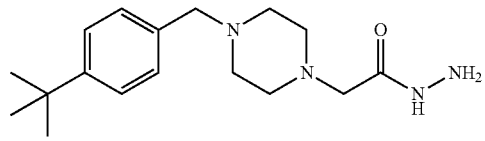 [SMILES: CC(C)(C)c1ccc(CN2CCN(CC(=O)NN)CC2)cc1]

Synthesized according to General Procedure C: 6{20} (4.12 g, 12.9 mmol, 1 equiv.), anhydrous hydrazine (1.2 mL, 38.8 mmol, 3 equiv.), ethanol (26.0 mL). Purification by silica gel column chromatography (4:1 EtOAc:MeOH) afforded 1{20} (3.36 g, 84%) as a beige solid. ¹H-NMR (500 MHz, CDCl₃): δ 8.17 (br s, 1H), 7.31 (d, 2H, J=8.5 Hz), 7.20 (d, 2H, J=8.5 Hz), 3.85 (br s, 2H), 3.46 (s, 2H), 3.05 (s, 2H), 2.52 (br s, 4H), 2.45 (br s, 4H), 1.30 (s, 9H). ¹³C-NMR (125 MHz, CDCl₃): δ 170.4, 149.9, 134.5, 128.7, 125.0, 62.4, 60.5, 53.5, 52.9, 34.3, 31.3.

1-(anthracen-9-ylmethyl)piperazine (5{21})

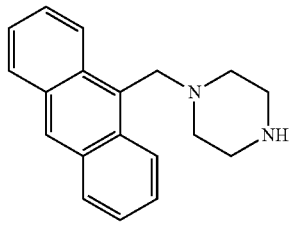 [SMILES: c1ccc2c(CN3CCNCC3)c3ccccc3cc2c1]

Synthesized according to General Procedure A: 9-(chloromethyl)anthracene (4{21}, 5 g, 18.7 mmol, 1 equiv.), piperazine (9.4 g, 109.0 mmol, 6 equiv.), THF (40.0 mL). Purification with flash column chromatography on silica gel (4:1 EtOAc:MeOH) afforded 5{21} (4.75 g, 93%) as a white solid. ¹H-NMR (500 MHz, CDCl₃): δ 8.50 (dd, 2H, J=0.5, 9.0 Hz), 8.41 (s, 1H), 8.00 (td, 2H, J=1.0, 8.5 Hz), 7.52 (ddd, 2H, J=1.5, 6.5, 8.0 Hz), 7.47 (ddd, 2H, J=1.5, 6.5, 8.5 Hz), 4.42 (s, 2H), 2.81 (t, 4H, J=5.0 Hz), 2.59 (br s, 4H), 1.87 (br s, 1H). ¹³C-NMR (125 MHz, CDCl₃): δ 131.4, 131.3, 129.6, 128.9, 127.3, 125.5, 125.1, 124.8, 54.8, 54.5, 46.1.

Ethyl 2-(4-(anthracen-9-ylmethyl)piperazin-1-yl)acetate (6{21})

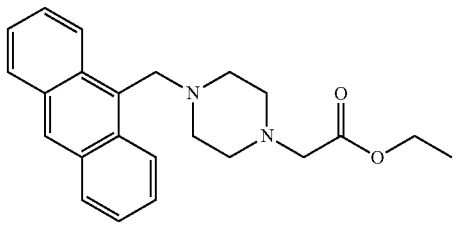 [SMILES: CCOC(=O)CN1CCN(Cc2c3ccccc3cc3ccccc23)CC1]

Synthesized according to General Procedure B: 5{21} (5.64 g, 20.4 mmol, 1 equiv.), ethyl chloroacetate (2.4 mL, 22.5 mmol, 1.1 equiv.), NaHCO₃ (2.14 g, 25.5 mmol, 1.25 equiv.), acetone (40.8 mL), chloroform (40.0 mL). Purification with flash column chromatography on silica gel (1:1 hexanes:EtOAc) afforded 6{21} (6.91 g, 93%) as an orange oil. ¹H-NMR (500 MHz, CDCl₃): δ 8.50 (d, 2H, J=8.0 Hz), 8.38 (s, 1H), 7.98 (d, 2H, J=8.5 Hz), 7.53 (t, 2H, J=8.0 Hz), 7.46 (t, 2H, J=7.0 Hz), 4.44 (s, 2H), 4.18 (q, 2H, J=7.0 Hz), 3.16 (s, 2H), 2.72 (br s, 4H), 2.54 (br s, 4H), 1.26 (t, 3H, J=7.0 Hz). ¹³C-NMR (125 MHz, CDCl₃): δ 170.0, 131.1, 131.1, 129.4, 128.7, 127.2, 125.3, 124.9, 124.6, 60.3, 59.2, 53.9, 53.0, 52.7, 14.0.

2-(4-(anthracen-9-ylmethyl)piperazin-1-yl)acetohydrazide (1{21})

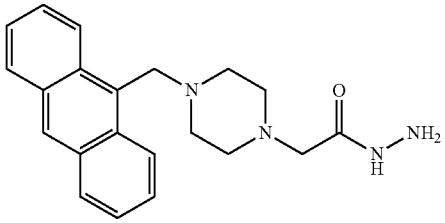 [SMILES: NNC(=O)CN1CCN(Cc2c3ccccc3cc3ccccc23)CC1]

Synthesized according to General Procedure C: 6{21} (6.82 g, 18.8 mmol, 1 equiv.), anhydrous hydrazine (1.8 mL, 56.4 mmol, 3 equiv.), ethanol (38.0 mL). Purification by silica gel column chromatography (4:1 EtOAc:MeOH) afforded 1{21} (3.56 g, 54%) as an orange semi-solid. $^1$H-NMR (500 MHz, CDCl$_3$): δ 8.46 (d, 2H, J=8.5 Hz), 8.42 (s, 1H), 8.21 (br s, 1H), 8.01 (d, 2H, J=8.5 Hz), 7.53 (ddd, 2H, J=1.5, 6.5, 8.0 Hz), 7.47 (ddd, 2H, J=1.0, 6.5, 8.0 Hz), 4.45 (s, 2H), 3.87 (br s, 2H), 3.04 (s, 2H), 2.64 (br s, 4H), 2.47 (br s, 4H). $^{13}$C-NMR (125 MHz, CDCl$_3$): δ 170.5, 131.3, 131.3, 129.2, 128.9, 127.5, 125.6, 124.9, 124.8, 60.4, 54.0, 53.7, 53.1.

1-(3,5-di-tert-butylbenzyl)piperazine (5{22})

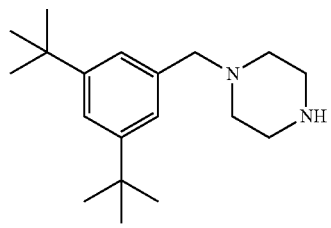 [SMILES: CC(C)(C)c1cc(CN2CCNCC2)cc(C(C)(C)C)c1]

Synthesized according to General Procedure A: 3,5-di-tert-butylbenzyl bromide (4{22}, 5 g, 17.7 mmol, 1 equiv.), piperazine (9.1 g, 105.9 mmol, 6 equiv.), THF (38.7 mL). Purification with flash column chromatography on silica gel (4:1 EtOAc:MeOH) afforded 5{22} (4.15 g, 82%) as a white solid. $^1$H-NMR (500 MHz, CDCl$_3$): δ 7.31 (t, 1H, J=2.0 Hz), 7.15 (d, 2H, J=2.0 Hz), 3.51 (s, 2H), 2.89 (t, 4H, J=5.0 Hz), 2.42 (br s, 4H), 1.73 (br s, 1H), 1.33 (s, 18H). $^{13}$C-NMR (125 MHz, CDCl$_3$): δ 150.3, 136.8, 123.3, 120.7, 64.1, 54.3, 46.1, 34.7, 31.5.

Ethyl 2-(4-(3,5-di-tert-butylbenzyl)piperazin-1-yl)acetate (6{22})

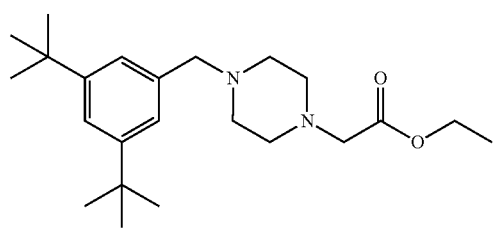 [SMILES: CCOC(=O)CN1CCN(Cc2cc(C(C)(C)C)cc(C(C)(C)C)c2)CC1]

Synthesized according to General Procedure B: 5{22} (4.02 g, 13.9 mmol, 1 equiv.), ethyl chloroacetate (1.6 mL, 15.3 mmol, 1.1 equiv.), NaHCO$_3$ (1.46 g, 17.4 mmol, 1.25 equiv.), acetone (27.8 mL). Purification with flash column chromatography on silica gel (1:1 hexanes:EtOAc) afforded 6{22} (4.64 g, 89%) as a light orange liquid. $^1$H-NMR (500 MHz, CDCl$_3$): δ 7.30 (t, 1H, J=2.0 Hz), 7.13 (d, 2H, J=2.0 Hz), 4.18 (q, 2H, J=7.0), 3.54 (s, 2H), 3.20 (s, 2H), 2.61 (br s, 4H), 2.54 (br s, 4H), 1.32 (s, 18H), 1.27 (t, 3H, J=7.0 Hz). $^{13}$C-NMR (125 MHz, CDCl$_3$): δ 170.3, 150.4, 136.7, 123.3, 120.8, 63.3, 60.5, 59.6, 53.2, 52.5, 34.7, 31.5, 14.2.

2-(4-(3,5-di-tert-butylbenzyl)piperazin-1-yl)acetohydrazide (1{22})

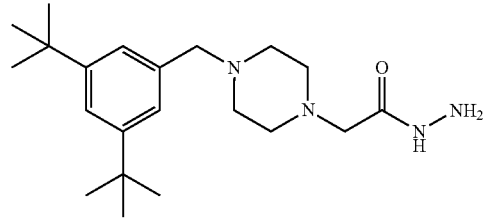 [SMILES: CC(C)(C)c1cc(CN2CCN(CC(=O)NN)CC2)cc(C(C)(C)C)c1]

Synthesized according to General Procedure C: 6{22} (4.57 g, 12.2 mmol, 1 equiv.), anhydrous hydrazine (1.1 mL, 36.6 mmol, 3 equiv.), ethanol (24.7 mL). Purification by silica gel column chromatography (4:1 EtOAc:MeOH) afforded 1{22} (2.88 g, 66%) as a beige solid. $^1$H-NMR (500 MHz, CDCl$_3$): δ 8.17 (br s, 1H), 7.31 (t, 1H, J=1.5 Hz), 7.13 (d, 2H, J=1.5 Hz), 3.84 (br s, 2H), 3.51 (s, 2H), 3.08 (s, 2H), 2.55 (br s, 4H), 2.47 (br s, 4H), 1.32 (s, 18H). $^{13}$C-NMR (125 MHz, CDCl$_3$): δ 170.5, 150.5, 136.7, 123.2, 120.9, 63.3, 60.6, 53.7, 52.9, 34.7, 31.5.

1-benzhydrylpiperazine (5{23})

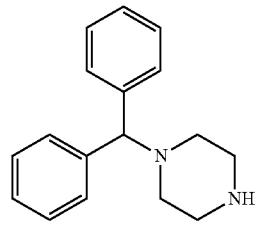 [SMILES: c1ccc(C(c2ccccc2)N2CCNCC2)cc1]

Synthesized according to General Procedure A: chlorodiphenylmethane (4{23}, 5 mL, 28.1 mmol, 1 equiv.), piperazine (14.5 g, 168.7 mmol, 6 equiv.), THF (61.4 mL). Purification with flash column chromatography on silica gel (4:1 EtOAc:MeOH) afforded 5{23} (5.12 g, 72%) as a light yellow solid. $^1$H-NMR (500 MHz, CDCl$_3$): δ 7.43 (d, 4H, J=7.0 Hz), 7.28 (t, 4H, J=7.5 Hz), 7.18 (t, 2H, J=7.5 Hz), 4.22 (s, 1H), 2.88 (t, 4H, J=5.0 Hz), 2.36 (br s, 4H), 1.46 (br s, 1H). $^{13}$C-NMR (125 MHz, CDCl$_3$): δ 142.6, 128.3, 127.9, 126.7, 76.7, 53.3, 46.3.

Ethyl 2-(4-benzhydrylpiperazin-1-yl)acetate (6{23})

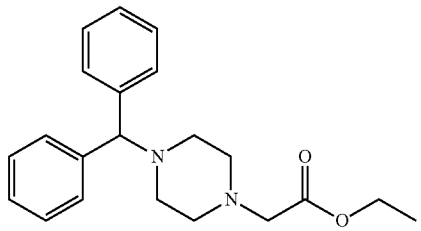 [SMILES: CCOC(=O)CN1CCN(C(c2ccccc2)c2ccccc2)CC1]

Synthesized according to General Procedure B: 5{23} (5.12 g, 20.3 mmol, 1 equiv.), ethyl chloroacetate (2.4 mL, 22.3 mmol, 1.1 equiv.), NaHCO$_3$ (2.13 g, 25.3 mmol, 1.25 equiv.), acetone (40.6 mL). Purification with flash column chromatography on silica gel (1:1 hexanes:EtOAc) afforded 6{23} (5.74 g, 87%) as a brown oil. $^1$H-NMR (500 MHz, CDCl$_3$): δ 7.43 (d, 4H, J=7.0 Hz), 7.27 (t, 4H, J=7.5 Hz), 7.17 (t, 2H, J=7.5 Hz), 4.26 (s, 1H), 4.18 (t, 2H, J=7.0 Hz), 3.22 (s, 2H), 2.63 (br s, 4H), 2.49 (br s, 4H), 1.26 (t, 3H, J=7.0 Hz). $^{13}$C-NMR (125 MHz, CDCl$_3$): δ 170.1, 142.5, 128.3, 127.8, 126.8, 76.0, 60.4, 59.3, 53.1, 51.5, 14.1.

2-(4-benzhydrylpiperazin-1-yl)acetohydrazide (1{23})

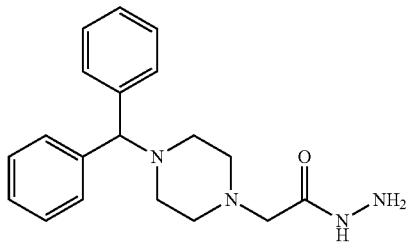 [SMILES: NNC(=O)CN1CCN(C(c2ccccc2)c2ccccc2)CC1]

Synthesized according to General Procedure C: 6{23} (5.68 g, 17.4 mmol, 1 equiv.), anhydrous hydrazine (1.6 mL, 52.2 mmol, 3 equiv.), ethanol (35.2 mL). Purification by silica gel column chromatography (4:1 EtOAc:MeOH) afforded 1{23} (3.60 g, 64%) as a light yellow solid. $^1$H-NMR (500 MHz, CDCl$_3$): δ 8.13 (br s, 1H), 7.41 (dd, 4H, J=1.5, 8.5 Hz), 7.28-7.25 (m, 4H), 7.20-7.16 (m, 2H), 4.23 (s, 1H), 3.82 (br s, 2H), 3.08 (s, 2H), 2.54 (br s, 4H), 2.40 (br s, 4H). $^{13}$C-NMR (125 MHz, CDCl$_3$): δ 170.5, 142.2, 128.5, 127.8, 127.0, 76.0, 60.5, 53.9, 51.8.

1-(naphthalen-1-ylmethyl)piperazine (5{24})

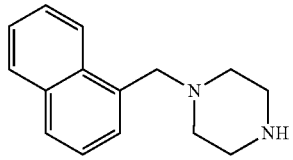 [SMILES: c1ccc2c(CN3CCNCC3)cccc2c1]

Synthesized according to General Procedure A: 1-(chloromethyl)naphthalene (4{24}, 5 mL, 33.4 mmol, 1 equiv.), piperazine (17.3 g, 200.6 mmol, 6 equiv.), THF (73.0 mL).

Purification with flash column chromatography on silica gel (4:1 EtOAc:MeOH) afforded 5{24} (6.58 g, 87%) as a beige solid. $^1$H-NMR (500 MHz, CDCl$_3$): δ 8.32 (d, 1H, J=8.0 Hz), 7.85 (d, 1H, J=8.0 Hz), 7.78 (d, 1H, J=8.0 Hz), 7.54-7.47 (m, 2H), 7.44-7.39 (m, 2H), 3.89 (s, 2H), 2.87 (t, 4H, J=5.0 Hz), 2.48 (br s, 4H), 1.68 (br s, 1H). $^{13}$C-NMR (125 MHz, CDCl$_3$): δ 134.3, 134.1, 132.8, 128.6, 128.1, 127.6, 125.9, 125.8, 125.3, 125.0, 62.0, 55.0, 46.4.

Ethyl 2-(4-(naphthalen-1-ylmethyl)piperazin-1-yl)acetate (6{24})

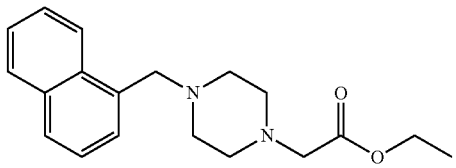 [SMILES: CCOC(=O)CN1CCN(Cc2cccc3ccccc23)CC1]

Synthesized according to General Procedure B: 5{24} (6.45 g, 28.5 mmol, 1 equiv.), ethyl chloroacetate (3.4 mL, 27.1 mmol, 1.1 equiv.), NaHCO$_3$ (2.99 g, 35.6 mmol, 1.25 equiv.), acetone (67.0 mL), chloroform (20 mL). Purification with flash column chromatography on silica gel (1:1 hexanes:EtOAc) afforded 6{24} (8.45 g, 95%) as an orange oil. $^1$H-NMR (500 MHz, CDCl$_3$): δ 8.31 (d, 1H, J=8.0 Hz), 7.84 (d, 1H, J=8.0 Hz), 7.77 (d, 1H, J=8.0 Hz), 7.53-7.46 (m, 2H), 7.44-7.38 (m, 2H), 4.18 (q, 2H, J=7.0 Hz), 3.92 (s, 2H), 3.19 (s, 2H), 2.60 (br s, 8H), 1.27 (t, 3H, J=7.0 Hz). $^{13}$C-NMR (125 MHz, CDCl$_3$): δ 170.1, 133.8, 133.6, 132.4, 128.2, 127.7, 127.2, 125.5, 125.4, 124.9, 124.6, 60.9, 60.4, 59.3, 53.0, 52.9, 14.1.

2-(4-(naphthalen-1-ylmethyl)piperazin-1-yl)acetohydrazide (1{24})

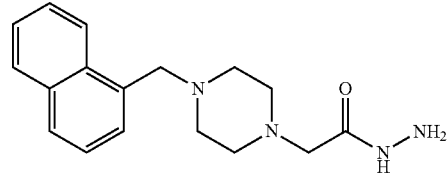 [SMILES: NNC(=O)CN1CCN(Cc2cccc3ccccc23)CC1]

Synthesized according to General Procedure C: 6{24} (8.29 g, 26.5 mmol, 1 equiv.), anhydrous hydrazine (2.5 mL, 79.6 mmol, 3 equiv.), ethanol (53.4 mL). Purification by silica gel column chromatography (4:1 EtOAc:MeOH) afforded 1{24} (6.86 g, 87%) as a brown oil. $^1$H-NMR (500 MHz, CDCl$_3$): δ 8.70 (d, 1H, J=8.0 Hz), 8.19 (br s, 1H), 7.84 (d, 1H, J=7.5 Hz), 7.77 (dd, 1H, J=3.0, 6.5 Hz), 7.52-7.46 (m, 2H), 7.41-7.38 (m, 2H), 3.90 (s, 2H), 3.87 (br s, 2H), 3.06 (s, 2H), 2.51 (br s, 8H). $^{13}$C-NMR (125 MHz, CDCl$_3$): δ 170.5, 133.7, 133.7, 132.4, 128.3, 127.9, 127.3, 125.6, 125.5, 125.0, 124.6, 60.9, 60.5, 53.6, 53.2.

1-(naphthalen-2-ylmethyl)piperazine (5{25})

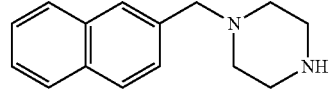 [SMILES: c1ccc2cc(CN3CCNCC3)ccc2c1]

Synthesized according to General Procedure A: 2-(bromomethyl)naphthalene (4{25}, 5 g, 22.6 mmol, 1 equiv.), piperazine (11.7 g, 135.7 mmol, 6 equiv.), THF (49.4 mL). Purification with flash column chromatography on silica gel (4:1 EtOAc:MeOH) afforded 5{25} (4.67 g, 91%) as a beige solid. $^1$H-NMR (500 MHz, CDCl$_3$): δ 7.82-7.79 (m, 3H), 7.74 (s, 1H) 7.50 (dd, 1H, J=1.5, 8.5 Hz), 7.48-7.42 (m, 2H), 3.64 (s, 2H), 2.88 (t, 4H, J=5.0 Hz), 2.45 (br s, 4H), 1.52 (br s, 1H). $^{13}$C-NMR (125 MHz, CDCl$_3$): δ 135.6, 133.2, 132.6, 127.7, 127.5, 127.5, 127.5, 127.4, 125.8, 125.4, 63.7, 54.5, 46.0.

Ethyl 2-(4-(naphthalen-2-ylmethyl)piperazin-1-yl)acetate (6{25})

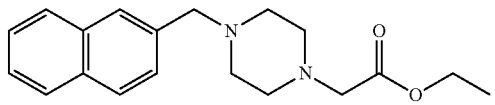 [SMILES: CCOC(=O)CN1CCN(Cc2ccc3ccccc3c2)CC1]

Synthesized according to General Procedure B: 5{25} (4.56 g, 20.2 mmol, 1 equiv.), ethyl chloroacetate (2.4 mL, 22.2 mmol, 1.1 equiv.), NaHCO$_3$ (2.12 g, 25.2 mmol, 1.25 equiv.), acetone (40.4 mL). Purification with flash column chromatography on silica gel (1:1 hexanes:EtOAc) afforded 6{25} (5.88 g, 93%) as an orange oil. $^1$H-NMR (500 MHz, CDCl$_3$): δ 7.82-7.78 (m, 3H), 7.73 (s, 1H) 7.49 (dd, 1H, J=1.5, 8.5 Hz), 7.47-7.42 (m, 2H), 4.18 (q, 2H, J=7.0 Hz), 3.67 (s, 2H), 3.20 (s, 2H), 2.61 (br s, 4H), 2.58 (br s, 4H), 1.26 (t, 3H, J=7.0 Hz). $^{13}$C-NMR (125 MHz, CDCl$_3$): δ 170.2, 135.6, 133.2, 132.6, 127.7, 127.6, 127.5, 127.5, 127.3, 125.8, 125.5, 63.0, 60.5, 59.4, 53.0, 52.8, 14.1.

2-(4-(naphthalen-2-ylmethyl)piperazin-1-yl)acetohydrazide (1{25})

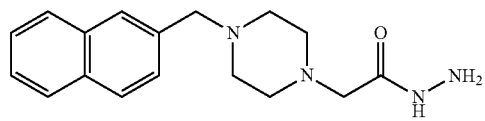 [SMILES: NNC(=O)CN1CCN(Cc2ccc3ccccc3c2)CC1]

Synthesized according to General Procedure C: 6{25} (5.74 g, 18.4 mmol, 1 equiv.), anhydrous hydrazine (1.7 mL, 55.2 mmol, 3 equiv.), ethanol (37.2 mL). Purification by silica gel column chromatography (4:1 EtOAc:MeOH) afforded 1{25} (4.49 g, 82%) as a white solid. $^1$H-NMR (500 MHz, CDCl$_3$): δ 8.17 (br s, 1H), 7.82-7.78 (m, 3H), 7.71 (s, 1H), 7.47-7.42 (m, 3H), 3.86 (br s, 2H), 3.64 (s, 2H), 3.06 (s, 2H), 2.53 (br s, 8H). $^{13}$C-NMR (125 MHz, CDCl$_3$): δ 170.4, 135.4, 133.1, 132.6, 127.8, 127.5, 127.5, 127.2, 125.9, 125.5, 62.9, 60.5, 53.5, 53.0.

1-((4-chlorophenyl)(phenyl)methyl)piperazine (5{26})

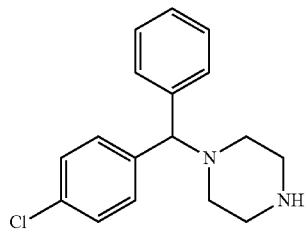 [SMILES: Clc1ccc(C(c2ccccc2)N2CCNCC2)cc1]

Synthesized according to General Procedure A: chloro(4-chlorophenyl)phenylmethane (4{26}, 5 mL, 26.1 mmol, 1 equiv.), piperazine (13.5 g, 156.7 mmol, 6 equiv.), THF (57.0 mL). Purification with flash column chromatography on silica gel (4:1 EtOAc:MeOH) afforded 5{26} (6.34 g, 85%) as a yellow liquid. $^1$H-NMR (500 MHz, CDCl$_3$): δ 7.39-7.37 (m, 4H), 7.30-7.24 (m, 4H) 7.20 (t, 1H, J=7.5 Hz), 4.21 (s, 1H), 2.89 (t, 4H, J=5.0 Hz), 2.36 (br s, 4H), 1.82 (br s, 1H). $^{13}$C-NMR (125 MHz, CDCl$_3$): δ 142.0, 141.2, 132.4, 129.2, 128.5, 128.5, 127.8, 127.0, 75.9, 53.2, 46.2.

Ethyl 2-(4-((4-chlorophenyl)(phenyl)methyl)piperazin-1-yl)acetate (6{26})

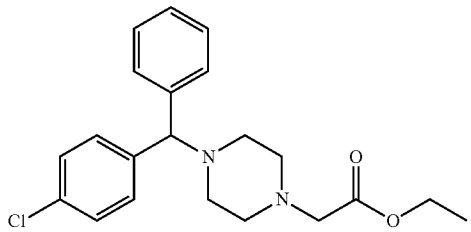 [SMILES: CCOC(=O)CN1CCN(C(c2ccccc2)c2ccc(Cl)cc2)CC1]

Synthesized according to General Procedure B: 5{26} (6.34 g, 22.1 mmol, 1 equiv.), ethyl chloroacetate (2.6 mL, 24.3 mmol, 1.1 equiv.), NaHCO$_3$ (2.32 g, 27.6 mmol, 1.25 equiv.), acetone (44.2 mL). Purification with flash column chromatography on silica gel (1:1 hexanes:EtOAc) afforded 6{26} (7.25 g, 90%) as an orange oil. $^1$H-NMR (500 MHz, CDCl$_3$): δ 7.37-7.34 (m, 4H), 7.28-7.22 (m, 4H) 7.19-7.16 (m, 1H), 4.22 (s, 1H), 4.17 (q, 2H, J=7.0 Hz), 3.21 (s, 2H), 2.61 (br s, 4H), 2.45 (br s, 4H), 1.25 (t, 3H, J=7.0 Hz). $^{13}$C-NMR (125 MHz, CDCl$_3$): δ 170.1, 142.0, 141.2, 132.4, 129.1, 128.5, 128.5, 127.7, 127.0, 75.2, 60.5, 59.3, 53.1, 51.4, 14.2.

2-(4-((4-chlorophenyl)(phenyl)methyl)piperazin-1-yl)acetohydrazide (1{26})

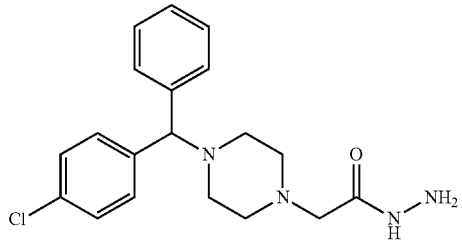 [SMILES: NNC(=O)CN1CCN(C(c2ccccc2)c2ccc(Cl)cc2)CC1]

Synthesized according to General Procedure C: 6{26} (7.25 g, 19.4 mmol, 1 equiv.), anhydrous hydrazine (1.8 mL, 58.3 mmol, 3 equiv.), ethanol (39.2 mL). Purification by silica gel column chromatography (4:1 EtOAc:MeOH) afforded 1{26} (6.54 g, 94%) as a yellow oil. $^1$H-NMR (500 MHz, CDCl$_3$): δ 8.15 (br s, 1H), 7.35-7.32 (m, 4H), 7.27-7.22 (m, 4H) 7.19-7.16 (m, 1H), 4.20 (s, 1H), 3.84 (br s, 2H), 3.06 (s, 2H), 2.52 (br s, 4H), 2.38 (br s, 4H). $^{13}$C-NMR (125 MHz, CDCl$_3$): δ 170.3, 141.7, 140.9, 132.5, 129.0, 128.5, 128.5, 127.6, 127.1, 75.1, 60.4, 53.7, 51.6.

1-(2-iodobenzyl)piperazine (5{27})

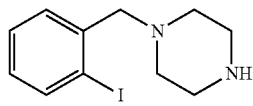

Synthesized according to General Procedure A: 2-iodobenzyl bromide (4{27}, 4.92 g, 16.8 mmol, 1 equiv.), piperazine (8.70 g, 101.0 mmol, 6 equiv.), THF (36.7 mL). Purification with flash column chromatography on silica gel (4:1 EtOAc:MeOH) afforded 5{27} (4.43 g, 89%) as a light yellow liquid. $^1$H-NMR (400 MHz, CDCl$_3$): δ 7.80 (dd, 1H, J=1.2, 8.0 Hz) 7.39 (dd, 1H, J=1.2, 7.6 Hz), 7.30-7.26 (m, 1H), 6.91 (dt, 1H, J=1.2, 7.2 Hz), 3.47 (s, 2H), 2.86 (t, 4H, J=4.8 Hz), 2.46 (br s, 4H), 1.76 (br s, 1H). $^{13}$C-NMR (100 MHz, CDCl$_3$): δ 140.4, 139.3, 130.2, 128.6, 127.8, 100.6, 66.9, 54.3, 46.0.

Ethyl 2-(4-(2-iodobenzyl)piperazin-1-yl)acetate (6{27})

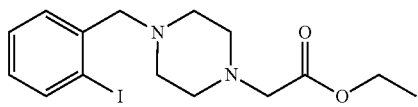 [SMILES: CCOC(=O)CN1CCN(Cc2ccccc2I)CC1]

Synthesized according to General Procedure B: 5{27} (4.36 g, 14.4 mmol, 1 equiv.), ethyl chloroacetate (1.7 mL, 15.9 mmol, 1.1 equiv.), NaHCO$_3$ (1.52 g, 18.1 mmol, 1.25 equiv.), acetone (28.8 mL). Purification with flash column chromatography on silica gel (1:1 hexanes:EtOAc) afforded 6{27} (4.92 g, 88%) as a yellow liquid. $^1$H-NMR (400 MHz, CDCl$_3$): δ 7.78 (dd, 1H, J=1.2, 8.0 Hz), 7.39 (dd, 1H, J=1.6, 7.6 Hz), 7.28-7.24 (m, 1H), 6.91 (dt, 1H, J=1.6, 7.6 Hz), 4.15 (q, 2H, J=7.2 Hz), 3.49 (s, 2H), 3.18 (s, 2H), 2.57 (br s, 8H), 1.24 (t, 3H, J=7.2 Hz). $^{13}$C-NMR (100 MHz, CDCl$_3$): δ 170.1, 140.3, 139.2, 130.1, 128.6, 127.8, 100.5, 66.2, 60.4, 59.4, 52.9, 52.5, 52.4.

2-(4-(2-iodobenzyl)piperazin-1-yl)acetohydrazide (1{27})

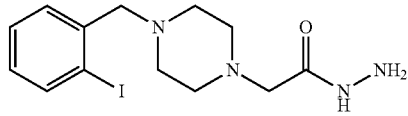 [SMILES: NNC(=O)CN1CCN(Cc2ccccc2I)CC1]

Synthesized according to General Procedure C: 6{27} (4.87 g, 12.5 mmol, 1 equiv.), anhydrous hydrazine (1.2 mL, 37.6 mmol, 3 equiv.), ethanol (25.0 mL). Purification by silica gel column chromatography (4:1 EtOAc:MeOH) afforded 1{27} (4.08 g, 87%) as a light yellow solid. $^1$H-NMR (400 MHz, CDCl$_3$): δ 8.17 (br s, 1H), 7.82 (dd, 1H, J=1.2, 7.6 Hz), 7.37 (dd, 1H, J=1.6, 7.6 Hz), 7.29 (dt, 1H, J=1.2, 7.2), 6.91 (dt, 1H, J=1.6, 7.6 Hz), 3.85 (br s, 2H), 3.52 (s, 2H), 3.08 (s, 2H), 2.54 (br s, 8H). $^{13}$C-NMR (125 MHz, CDCl$_3$): δ 170.5, 140.2, 139.5, 130.2, 128.7, 128.0, 100.6, 61.2, 60.6, 53.7, 52.9.

1-(4-vinylbenzyl)piperazine (8)

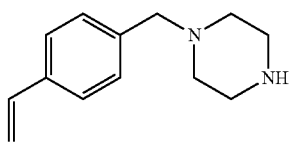

Synthesized according to General Procedure A: 4-vinylbenzyl chloride (7, 5.56 g, 32.8 mmol, 1 equiv.), piperazine (16.9 g, 196.6 mmol, 6 equiv.), THF (71.8 mL). Purification with flash column chromatography on silica gel (gradient, 4:1 to 1:4 EtOAc:MeOH) afforded 8 (5.39 g, 81%) as a white solid. $^1$H-NMR (500 MHz, CDCl$_3$): δ 7.32 (d, 2H, J=8.0 Hz), 7.24 (d, 2H, J=8.0 Hz), 6.66 (dd, 1H, J=11.0, 18.0 Hz), 5.69 (dd, 1H, J=0.5, 18.0 Hz), 5.18 (dd, 1H, J=0.5, 11.0 Hz), 3.43 (s, 2H), 2.84 (t, 4H, J=5.0 Hz), 2.63 (br s, 1H), 2.37 (br s, 4H). $^{13}$C-NMR (125 MHz, CDCl$_3$): δ 137.5, 136.4, 136.2, 129.1, 125.8, 113.3, 63.1, 54.0, 45.7.

Ethyl 2-(4-(4-vinylbenzyl)piperazin-1-yl)acetate (9)

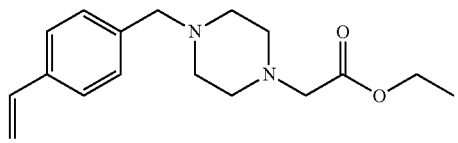 [SMILES: C=Cc1ccc(CN2CCN(CC(=O)OCC)CC2)cc1]

Synthesized according to General Procedure B: 8 (5.33 g, 26.4 mmol, 1 equiv.), ethyl chloroacetate (3.1 mL, 29.0 mmol, 1.1 equiv.), NaHCO$_3$ (2.77 g, 33.0 mmol, 1.25 equiv.), acetone (52.8 mL), chloroform (30.0 mL). Purification with flash column chromatography on silica gel (1:1 hexanes:EtOAc) afforded 9 (3.31 g, 70%) as an orange oil. $^1$H-NMR (500 MHz, CDCl$_3$): δ 7.35 (d, 2H, J=8.0 Hz), 7.26 (d, 2H, J=8.0 Hz), 6.69 (dd, 1H, J=11.0, 17.5 Hz), 5.72 (dd, 1H, J=0.5, 17.5 Hz), 5.21 (dd, 1H, J=1.0, 11.0 Hz), 4.17 (q, 2H, J=7.0 Hz), 3.49 (s, 2H), 3.19 (s, 2H), 2.59 (br s, 4H), 2.52 (br s, 4H), 1.26 (t, 3H, J=7.0 Hz). $^{13}$C-NMR (125 MHz, CDCl$_3$): δ 170.2, 137.7, 136.5, 136.4, 129.3, 126.0, 113.4, 62.6, 60.5, 59.5, 53.0, 52.7, 14.2.

2-(4-(4-ethylbenzyl)piperazin-1-yl)acetohydrazide (1{28})

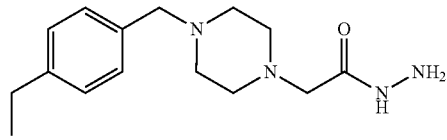 [SMILES: CCc1ccc(CN2CCN(CC(=O)NN)CC2)cc1]

Synthesized according to General Procedure C: 9 (3.23 g, 11.2 mmol, 1 equiv.), anhydrous hydrazine (1.1 mL, 33.6 mmol, 3 equiv.), ethanol (22.6 mL). Purification by silica gel column chromatography (4:1 EtOAc:MeOH) afforded 1{28} (1.92 g, 62%) as a white solid. $^1$H-NMR (500 MHz, CDCl$_3$): δ 8.14 (br s, 1H), 7.20 (d, 2H, J=8.0 Hz), 7.14 (d, 2H, J=8.0 Hz), 3.84 (d, 2H, J=4.0 Hz), 3.47 (s, 2H), 3.06 (s, 2H), 2.63 (q, 2H, J=7.5 Hz), 2.53 (br s, 4H), 2.45 (br s, 4H), 1.22 (t, 3H, J=7.5 Hz). $^{13}$C-NMR (125 MHz, CDCl$_3$): δ 170.5, 143.1, 134.9, 129.1, 127.7, 62.6, 60.5, 53.6, 52.9, 28.5, 15.5.

Ethyl 2-(4-(2-((phenylsulfonyl)methyl)benzyl)piperazin-1-yl)acetate (6{29})

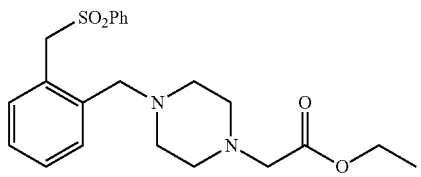

To a round-bottom flask were added 2-[(Phenylsulfonyl)methyl]benzyl bromide (4{29}, 1.0 g, 3.08 mmol, 1.0 equiv.), 10 (1.06 g, 6.16 mmol, 2.0 equiv.), K$_2$CO$_3$ (1.70 g, 12.32 mmol, 4.0 equiv.), and 3:2 THF:acetone (15 mL). The reaction mixture was stirred at reflux overnight. The reaction mixture was cooled to room temperature. The solid was filtered and washed with acetone. The filtrate was concentrated and purified by silica gel column chromatography (gradient, 25-50% EtOAc/hexanes) to afford 6{29} (920.1 mg, 72%) as an off-white solid. $^1$H-NMR (500 MHz, CDCl$_3$): δ 7.64 (dd, 2H, J=0.5, 8.0 Hz), 7.60-7.57 (m, 1H), 7.44 (t, 2H, J=8.0 Hz), 7.21 (t, 1H, J=8.0 Hz), 7.12 (d, 2H, J=7.5 Hz), 6.98 (d, 1H, J=7.5 Hz), 4.81 (s, 2H), 4.14 (q, 2H, J=7.0), 3.31 (s, 2H), 3.15 (s, 2H), 2.50 (br s, 4H), 2.36 (br s, 4H), 1.22 (t, 3H, J=7.0 Hz). $^{13}$C-NMR (125 MHz, CDCl$_3$): δ 170.1, 138.6, 138.1, 133.6, 132.4, 131.0, 128.8, 128.5, 128.4, 127.9, 127.3, 61.1, 60.4, 59.2, 58.9, 52.8, 52.6, 14.1.

2-(4-(2-((phenylsulfonyl)methyl)benzyl)piperazin-1-yl)acetohydrazide (1{29})

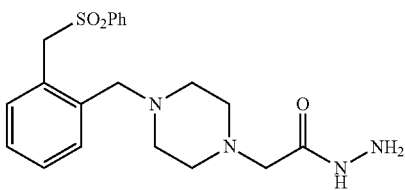

Synthesized according to General Procedure C: 6{29} (1.16 g, 2.77 mmol, 1 equiv.), anhydrous hydrazine (0.26 mL, 8.32 mmol, 3 equiv.), ethanol (15.6 mL), methanol (10 mL). Purification by silica gel column chromatography (4:1 EtOAc:MeOH) afforded 1{29} (0.88 g, 79%) as a white solid. $^1$H-NMR (500 MHz, CDCl$_3$): δ 8.10 (br s, 1H), 7.66 (dd, 2H, J=0.5, 8.0 Hz), 7.64-7.61 (m, 1H), 7.47 (t, 2H, J=8.0 Hz), 7.24 (dt, 1H, J=1.0, 7.5 Hz), 7.17-7.12 (m, 2H), 6.95 (d, 1H, J=7.5 Hz), 4.80 (s, 2H), 3.83 (br s, 2H), 3.40 (s, 2H), 3.04 (s, 2H), 2.47 (br s, 4H), 2.35 (br s, 4H). $^{13}$C-NMR (125 MHz, CDCl$_3$): δ 170.4, 138.6, 138.0, 133.7, 132.6, 131.1, 128.9, 128.7, 128.5, 128.0, 127.5, 61.1, 60.5, 59.1, 53.6, 53.0.

Ethyl 2-(4-phenylpiperazin-1-yl)acetate (6{30})

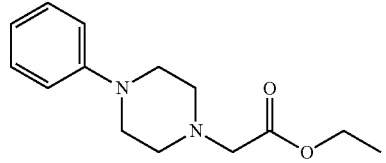 [SMILES: CCOC(=O)CN1CCN(c2ccccc2)CC1]

Synthesized according to General Procedure B: 1-phenylpiperazine (5{30}, 1 mL, 6.55 mmol, 1 equiv.), ethyl chloroacetate (0.77 mL, 7.20 mmol, 1.1 equiv.), NaHCO$_3$ (0.69 g, 8.18 mmol, 1.25 equiv.), acetone (13.1 mL). Purification with flash column chromatography on silica gel (1:1 hexanes:EtOAc) afforded 6{30} (1.50 g, 93%) as a light yellow liquid. $^1$H-NMR (500 MHz, CDCl$_3$): δ 7.20 (dd, 2H, J=7.0, 8.5 Hz), 6.87 (dd, 2H, J=1.0, 9.0 Hz), 6.80 (t, 1H, J=7.0 Hz), 4.15 (q, 2H, J=7.0 Hz), 3.20 (s, 2H), 3.19 (t, 4H, J=5.0 Hz), 2.68 (t, 4H, J=5.0 Hz), 1.23 (t, 3H, J=7.0 Hz). $^{13}$C-NMR (125 MHz, CDCl$_3$): δ 169.6, 150.8, 128.6, 119.2, 115.6, 60.1, 58.9, 52.5, 48.5, 13.8.

2-(4-phenylpiperazin-1-yl)acetohydrazide (1{30})

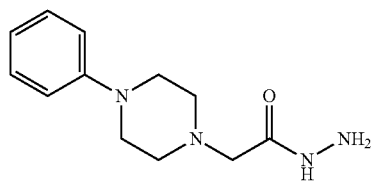 [SMILES: NNC(=O)CN1CCN(c2ccccc2)CC1]

Synthesized according to General Procedure C: 6{30} (1.23 g, 6.06 mmol, 1 equiv.), anhydrous hydrazine (0.96 mL, 18.2 mmol, 3 equiv.), ethanol (12.1 mL). Purification by silica gel column chromatography (4:1 EtOAc:MeOH) afforded 1{30} (1.23 g, 87%) as a yellow oil. ¹H-NMR (500 MHz, CDCl₃): δ 8.20 (br s, 1H), 7.29-7.26 (m, 2H), 6.92 (d, 2H, J=8.0 Hz), 6.88 (t, 1H, J=7.0 Hz), 3.51 (br s, 2H), 3.20 (t, 4H, J=5.0 Hz), 3.16 (s, 2H), 2.70 (t, 4H, J=5.0 Hz), 1.23 (t, 3H, J=7.0 Hz). ¹³C-NMR (125 MHz, CDCl₃): δ 170.2, 150.9, 129.1, 120.0, 116.1, 60.5, 53.6, 49.2.

2-phenyl-2-(p-tolyl)-1,3-dioxolane (12)

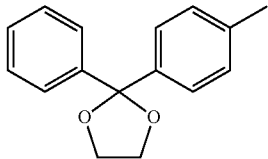 [SMILES: Cc1ccc(C2(c3ccccc3)OCCO2)cc1]

To a round-bottom flask were added 4-methylbenzophenone (11, 5.0 g, 25.5 mmol, 1.0 equiv.), ethylene glycol (57 mL, 1020 mmol, 40.0 equiv.), para-toluenesulfonic acid monohydrate (147 mg, 0.77 mmol, 0.03 equiv.), and toluene (65 mL, 0.4 M). The biphasic reaction mixture was stirred vigorously at reflux with a Dean-Stark trap for 4 days. The reaction mixture was cooled to room temperature. The reaction mixture was washed with saturated NaHCO₃ (2×50 mL) and brine (2×50 mL), dried over MgSO₄, filtered, and concentrated. Recrystallization from hexanes yielded 12 (4.58 g, 75%) as a white solid. ¹H-NMR (500 MHz, CDCl₃) δ 7.58-7.55 (m, 2H), 7.45-7.40 (d, 2H, J=8.0 Hz), 7.38-7.35 (m, 2H), 7.33-7.30 (m, 1H), 7.18 (d, 2H, J=8.0 Hz), 4.09 (s, 4H), 2.37 (s, 3H). ¹³C-NMR (125 MHz, CDCl₃): δ 142.2, 139.1, 137.7, 128.7, 128.0, 127.9, 126.1, 126.0, 109.4, 64.8, 21.1.

2-(4-(bromomethyl)phenyl)-2-phenyl-1,3-dioxolane (13)

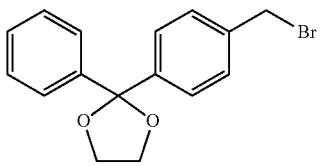 [SMILES: BrCc1ccc(C2(c3ccccc3)OCCO2)cc1]

To a round-bottom flask were added 12 (3.54 g, 14.7 mmol, 1.0 equiv.), N-bromosuccinimide (2.9 g, 16.2 mmol, 1.1 equiv.), AIBN (48 mg, 0.29 mmol, 0.02 equiv.), and CCl₄ (60 mL, 0.25 M). The reaction mixture was stirred at reflux for 6.5 hours. The reaction mixture was cooled to room temperature. The succinimide was filtered and washed with CCl₄. The filtrate was concentrated and crystallized from EtOAc/hexanes to yield 13 (2.57 g, 55%) as a white solid. ¹H-NMR (500 MHz, CDCl₃) δ 7.56-7.53 (m, 4H), 7.38-7.35 (m, 4H), 7.33-7.29 (m, 1H), 4.48 (s, 2H), 4.08 (s, 4H). ¹³C-NMR (125 MHz, CDCl₃): δ 142.4, 141.8, 137.4, 128.8, 128.1, 128.1, 126.5, 125.9, 109.0, 64.8, 33.1.

Ethyl 2-(4-(4-(2-phenyl-1,3-dioxolan-2-yl)benzyl)piperazin-1-yl)acetate (14)

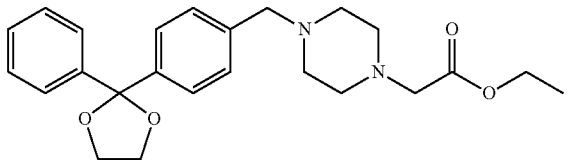 [SMILES: CCOC(=O)CN1CCN(Cc2ccc(C3(c4ccccc4)OCCO3)cc2)CC1]

To a round-bottom flask were added 13 (2.57 g, 8.05 mmol, 1.0 equiv.), 10 (2.09 g, 12.1 mmol, 1.5 equiv.), K₂CO₃ (3.35 g, 24.2 mmol, 3.0 equiv.), and acetone (40 mL, 0.2 M). The reaction mixture was stirred overnight at reflux. The reaction mixture was cooled to room temperature. The solid was filtered and washed with acetone. The filtrate was concentrated and purified by silica gel column chromatography (gradient, 50-100% EtOAc/hexanes) to yield 14 (2.54 g, 77%) as a yellow oil. ¹H-NMR (500 MHz, CDCl₃) δ 7.52-7.50 (m, 2H), 7.44 (d, 2H, J=8.5 Hz), 7.34-7.25 (m, 5H), 4.17 (q, 2H, J=7.0 Hz), 4.09-4.06 (m, 2H), 4.05-4.02 (m, 2H), 2.57 (br s, 4H), 2.50 (br s, 4H), 1.26 (t, 3H, J=7.0 Hz). ¹³C-NMR (125 MHz, CDCl₃): δ 170.3, 142.1, 140.9, 137.9, 128.9, 128.1, 128.0, 126.1, 126.0, 109.4, 64.8, 62.6, 60.6, 59.5, 53.1, 52.7, 14.2.

2-(4-(4-(2-phenyl-1,3-dioxolan-2-yl)benzyl)piperazin-1-yl)acetohydrazide (15)

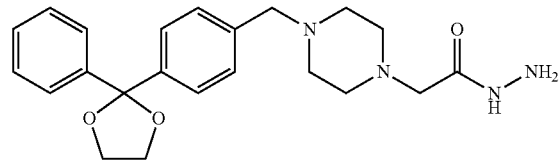 [SMILES: NNC(=O)CN1CCN(Cc2ccc(C3(c4ccccc4)OCCO3)cc2)CC1]

Synthesized according to General Procedure C: 14 (2.54 g, 6.19 mmol, 1 equiv.), anhydrous hydrazine (0.78 mL, 24.8 mmol, 4 equiv.), ethanol (12 mL). 15 (1.82 g, 74%) was obtained as a white solid, which was used without further purification after extraction. ¹H-NMR (500 MHz, CDCl₃): δ 8.14 (br s, 1H), 7.52-7.50 (m, 2H), 7.44 (d, 2H, J=8.0 Hz), 7.33-7.30 (m, 2H), 7.28-7.23 (m, 3H), 4.07-4.04 (m, 2H), 4.03-4.00 (m, 2H), 3.85 (br s, 2H), 3.46 (s, 2H), 3.04 (s, 2H), 2.50 (br s, 4H), 2.43 (br s, 4H). ¹³C-NMR (125 MHz, CDCl₃): δ 170.4, 142.0, 140.9, 137.7, 128.7, 128.0, 127.9, 126.0, 125.9, 109.2, 64.7, 62.4, 60.5, 53.5, 52.9.

2-(4-(4-benzoylbenzyl)piperazin-1-yl)acetohydrazide (1{31})

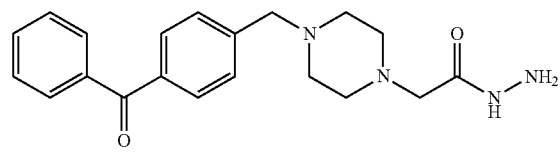 [SMILES: NNC(=O)CN1CCN(Cc2ccc(C(=O)c3ccccc3)cc2)CC1]

To a stirred solution of 15 (1.82 g, 4.57 mmol, 1.0 equiv.) in MeOH (14 mL, 0.33 M) was added 10% aqueous HCl (14 mL). The reaction mixture was stirred overnight at room temperature. The MeOH was evaporated, and the resulting aqueous solution was made basic (pH>12) by the addition of 1M NaOH. The aqueous solution was extracted with DCM (4×25 mL). The combined organic layers were washed with brine (25 mL), dried over MgSO$_4$, filtered, and concentrated to yield 1{31} (726 mg, 45%) as a yellow oily solid, which was used without further purification. $^1$H-NMR (500 MHz, CDCl$_3$): δ 8.16 (br s, 1H), 7.75-7.71 (m, 4H), 7.53 (t, 1H, J=7.5 Hz), 7.42 (t, 2H, J=7.5 Hz), 7.38 (d, 2H, J=8.0 Hz), 3.85 (br s, 2H), 3.53 (s, 2H), 3.03 (s, 2H), 2.51 (br s, 4H), 2.45 (br s, 4H). $^{13}$C-NMR (125 MHz, CDCl$_3$): δ 196.2, 170.2, 142.9, 137.4, 136.2, 132.2, 130.0, 129.8, 128.6, 128.1, 62.2, 60.4, 53.4, 52.9.

5-(1-benzyl-1H-1,2,3-triazol-4-yl)-2-hydroxybenzaldehyde (2{27})

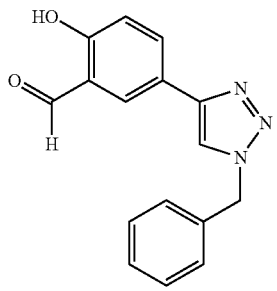 [SMILES: O=Cc1cc(-c2cn(Cc3ccccc3)nn2)ccc1O]

5-ethynylsalicylaldehyde (2{26}, 50 mg, 0.34 mmol, 1.0 equiv.) and benzyl azide (91 mg, 86 μL, 0.68 mmol, 2.0 equiv.) were suspended in 1:1 t-BuOH:H$_2$O (1.2 mL). Sodium L-ascorbate (24 mg in 100 μL H$_2$O, 0.34 mmol, 1.0 equiv.) was added, followed by copper (II) sulfate pentahydrate (67 mg in 200 μL H$_2$O, 0.10 mmol, 0.33 equiv.). The reaction mixture was stirred at room temperature overnight. The reaction mixture was diluted with H$_2$O (10 mL), and the aqueous layer was extracted with DCM (3×10 mL). The combined organic layers were washed with brine (10 mL), dried over MgSO$_4$, filtered, and concentrated. The crude product was purified by silica gel column chromatography (25-50% EtOAc/hexanes) to yield 2{27} (47.5 mg, 0.17 mmol, 50.0%) as an off-white solid. $^1$H-NMR (500 MHz, CDCl$_3$): δ 11.03 (s, 1H), 9.92 (s, 1H), 8.07 (d, 1H, J=2.5 Hz), 7.86 (dd, 1H, J=2.0, 8.0 Hz), 7.65 (s, 1H), 7.41-7.35 (m, 3H), 7.31 (dd, 2H, J=2.0, 7.5 Hz), 7.01 (d, 1H, J=8.5 Hz), 5.57 (s, 2H). $^{13}$C-NMR (125 MHz, CDCl$_3$): δ 196.5, 161.3, 134.4, 134.2, 130.6, 129.1, 128.8, 128.1, 124.9, 122.9, 120.6, 118.9, 118.1, 54.3.

N'-(3,5-di-tert-butyl-2-hydroxybenzylidene)-2-(4-(4-methoxybenzyl)piperazin-1-yl)acetohydrazide (3{2,7})

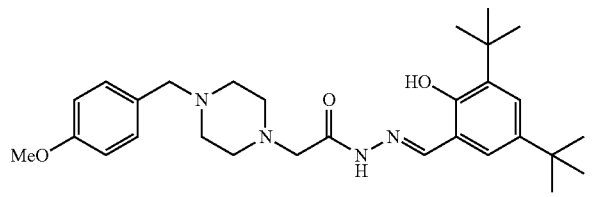 [SMILES: COc1ccc(CN2CCN(CC(=O)N/N=C/c3cc(C(C)(C)C)cc(C(C)(C)C)c3O)CC2)cc1]

To a stirred solution of hydrazide 1{2} (112 mg, 0.40 mmol, 1.0 equiv.) and aldehyde 2{7} (94 mg, 0.40 mmol, 1.0 equiv.) in EtOH (3 mL, 0.15 M) was added 1.2 M HCl (7 mol %). The reaction mixture was stirred at reflux overnight. The reaction mixture was cooled to room temperature, and a white crystalline solid formed upon cooling. The crystals were filtered and washed with cold EtOH to yield 3{2,7} (118 mg, 0.24 mmol, 59.0%) as a white solid. $^1$H-NMR (500 MHz, CDCl$_3$): δ 11.32 (br s, 1H), 9.98 (br s, 1H), 8.44 (s, 1H), 7.38 (d, 1H, J=2.0 Hz), 7.23 (d, 2H, J=9.0 Hz), 7.05 (d, 1H, J=2.5 Hz), 6.87 (d, 2H, J=8.5 Hz), 3.81 (s, 3H), 3.49 (s, 2H), 3.19 (s, 2H), 2.62 (br s, 4H), 2.51 (br s, 4H), 1.44 (s, 9H), 1.30 (s, 9H). $^{13}$C-NMR (125 MHz, CDCl$_3$): δ 165.6, 158.7, 155.5, 152.4, 140.7, 136.8, 130.2, 129.6, 126.8, 125.6, 116.3, 113.6, 62.2, 60.9, 55.2, 53.6, 52.8, 35.0, 34.1, 31.4, 29.3. HRMS (ESI): 495.3340 (M+1); calcd. for C$_{29}$H$_{43}$N$_4$O$_3$: 495.3335.

N'-(3,5-di-tert-butyl-2-hydroxybenzylidene)-2-(4-(2,5-dimethoxybenzyl)piperazin-1-yl)acetohydrazide (3{4,7})

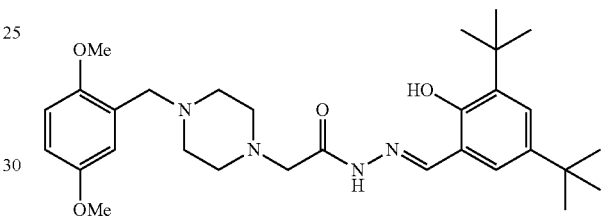

To a stirred solution of hydrazide 1{4} (100 mg, 0.32 mmol, 1.0 equiv.) and aldehyde 2{7} (75 mg, 0.32 mmol, 1.0 equiv.) in EtOH (2.2 mL, 0.15 M) was added 1.2 M HCl (7 mol %). The reaction mixture was stirred at reflux overnight. The reaction mixture was cooled to room temperature and concentrated. The crude product was purified by silica gel column chromatography (gradient, 0-10% MeOH/EtOAc) to yield 3{4,7} (106.2 mg, 0.20 mmol, 63.2%) as a white solid. $^1$H-NMR (500 MHz, CDCl$_3$): δ 11.34 (br s, 1H), 10.02 (br s, 1H), 8.43 (s, 1H), 7.38 (d, 1H, J=2.5 Hz), 7.05 (d, 1H, J=2.0 Hz), 6.97 (d, 1H, J=3.0 Hz), 6.82 (d, 1H, J=8.0 Hz), 6.77 (dd, 1H, J=3.0, 8.0 Hz), 3.79 (s, 3H), 3.78 (s, 3H), 3.59 (s, 2H), 3.19 (s, 2H), 2.64 (br s, 4H), 2.59 (br s, 4H), 1.44 (s, 9H), 1.30 (s, 9H). $^{13}$C-NMR (125 MHz, CDCl$_3$): δ 165.7, 155.5, 153.5, 152.5, 152.0, 140.7, 136.8, 127.1, 126.8, 125.6, 116.5, 116.3, 112.2, 111.6, 60.9, 56.1, 55.8, 55.7, 53.7, 52.9, 35.1, 34.1, 31.4, 29.4. HRMS (ESI): 525.3449 (M+1); calcd. for C$_{30}$H$_{45}$N$_4$O$_4$: 525.3441.

2-(4-(4-(benzyloxy)benzyl)piperazin-1-yl)-N'-(3,5-di-tert-butyl-2-hydroxybenzylidene)acetohydrazide (3{18,7})

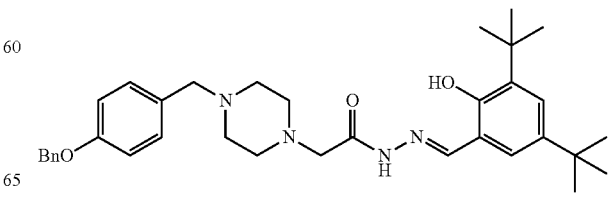

To a stirred solution of hydrazide 1{18} (100 mg, 0.29 mmol, 1.0 equiv.) and aldehyde 2{7} (68 mg, 0.29 mmol, 1.0 equiv.) in EtOH (2 mL, 0.15 M) was added 1.2 M HCl (7 mol %). The reaction mixture was stirred at reflux overnight. The reaction mixture was cooled to room temperature and concentrated. The crude product was purified by silica gel column chromatography (gradient, 0-10% MeOH/EtOAc) to yield 3{18,7} (97.4 mg, 0.17 mmol, 58.7%) as a white solid. $^1$H-NMR (500 MHz, CDCl$_3$): δ 11.38 (br s, 1H), 10.03 (br s, 1H), 8.43 (s, 1H), 7.45 (d, 2H, J=7.0 Hz), 7.42-7.39 (m, 3H), 7.34 (t, 1H, J=7.0 Hz), 7.24 (d, 2H, J=8.5 Hz), 7.07 (d, 1H, J=2.0 Hz), 6.96 (d, 2H, J=8.5 Hz), 5.07 (s, 2H), 3.50 (s, 2H), 3.20 (s, 2H), 2.63 (br s, 4H), 2.53 (br s, 4H), 1.46 (s, 9H), 1.32 (s, 9H). $^{13}$C-NMR (125 MHz, CDCl$_3$): δ 165.7, 158.0, 155.5, 152.5, 140.7, 137.0, 136.8, 130.2, 130.0, 128.5, 127.9, 127.4, 126.8, 125.6, 116.3, 114.5, 70.0, 62.2, 60.9, 53.6, 52.8, 35.1, 34.1, 31.4, 29.4. HRMS (ESI): 571.3652 (M+1); calcd. for C$_{35}$H$_{47}$N$_4$O$_3$: 571.3648.

N'-(3-allyl-2-hydroxybenzylidene)-2-(4-(4-(tert-butyl)benzyl)piperazin-1-yl)acetohydrazide (3{20,24})

To a stirred solution of hydrazide 1{25} (100 mg, 0.34 mmol, 1.0 equiv.) and aldehyde 2{7} (80 mg, 0.34 mmol, 1.0 equiv.) in EtOH (2.3 mL, 0.15 M) was added 1.2 M HCl (7 mol %). The reaction mixture was stirred at reflux overnight. The reaction mixture was cooled to room temperature and concentrated. The crude product was purified by silica gel column chromatography (gradient, 0-10% MeOH/EtOAc) to yield 3{25,7} (142.3 mg, 0.28 mmol, 81.3%) as a white solid. $^1$H-NMR (500 MHz, CDCl$_3$): δ 11.40 (br s, 1H), 10.05 (br s, 1H), 8.43 (s, 1H), 7.86-7.83 (m, 3H), 7.75 (s, 1H), 7.53-7.43 (m, 3H), 7.41 (d, 1H, J=2.5 Hz), 7.07 (d, 1H, J=2.5 Hz), 3.72 (s, 2H), 3.21 (s, 2H), 2.65 (br s, 4H), 2.59 (br s, 4H), 1.47 (s, 9H), 1.33 (s, 9H). $^{13}$C-NMR (125 MHz, CDCl$_3$): δ 165.6, 155.5, 152.4, 140.7, 136.8, 135.3, 133.2, 132.7, 127.9, 127.6, 127.6, 127.6, 127.3, 126.8, 126.0, 125.6, 125.6, 116.3, 62.9, 60.9, 53.6, 53.0, 35.0, 34.1, 31.4, 29.4. HRMS (ESI): 515.3389 (M+1); calcd. for C$_{32}$H$_{43}$N$_4$O$_2$: 515.3386.

N'-(3,5-di-tert-butyl-2-hydroxybenzylidene)-2-(4-(4-ethylbenzyl)piperazin-1-yl)acetohydrazide (3{28,7})

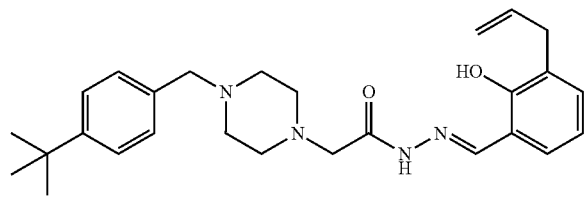 [SMILES: C=CCc1cccc(/C=N/NC(=O)CN2CCN(Cc3ccc(C(C)(C)C)cc3)CC2)c1O]

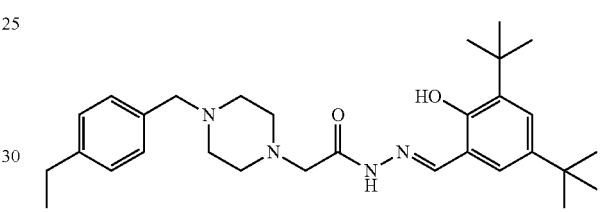

To a stirred solution of hydrazide 1{20} (100 mg, 0.33 mmol, 1.0 equiv.) and aldehyde 2{24} (53.5 mg, 0.33 mmol, 1.0 equiv.) in EtOH (2.2 mL, 0.15 M) was added 1.2 M HCl (7 mol %). The reaction mixture was stirred at reflux overnight. The reaction mixture was cooled to room temperature and concentrated. The crude product was purified by silica gel column chromatography (gradient, 0-10% MeOH/EtOAc) to yield 3{20,24} (102.0 mg, 0.23 mmol, 68.9%) as a light brown solid. $^1$H-NMR (500 MHz, CDCl$_3$): δ 11.31 (br s, 1H), 10.09 (br s, 1H), 8.38 (s, 1H), 7.36 (d, 2H, J=8.5 Hz), 7.25 (d, 2H, J=8.5 Hz), 7.19 (d, 1H, J=7.5 Hz), 7.08 (dd, 1H, J=1.5, 7.5 Hz), 6.85 (t, 1H, J=7.5 Hz), 6.04 (tdd, 1H, J=6.5, 10.0, 16.5 Hz), 5.12-5.06 (m, 2H), 3.52 (s, 2H), 3.47 (d, 2H, J=6.5 Hz), 3.20 (s, 2H), 2.63 (br s, 4H), 2.54 (br s, 4H), 1.33 (s, 9H). $^{13}$C-NMR (125 MHz, CDCl$_3$): δ 165.8, 156.3, 151.1, 150.0, 136.4, 134.6, 132.2, 129.1, 128.7, 128.1, 125.1, 118.9, 116.8, 115.6, 62.5, 60.9, 53.6, 53.0, 34.4, 33.8, 31.3. HRMS (ESI): 449.2915 (M+1); calcd. for C$_{27}$H$_{37}$N$_4$O$_2$: 449.2917.

N'-(3,5-di-tert-butyl-2-hydroxybenzylidene)-2-(4-(naphthalen-2-ylmethyl)piperazin-1-yl)acetohydrazide (3{25,7})

To a stirred solution of hydrazide 1{28} (26 mg, 0.094 mmol, 1.0 equiv.) and aldehyde 2{7} (22 mg, 0.094 mmol, 1.0 equiv.) in EtOH (1 mL) was added 1.2 M HCl (7 mol %). The reaction mixture was stirred at reflux overnight. The reaction mixture was cooled to room temperature and concentrated. The crude product was purified by silica gel column chromatography (gradient, 0-10% MeOH/EtOAc) to yield 3{28,7} (34.6 mg, 0.070 mmol, 75%) as a white solid. $^1$H-NMR (500 MHz, CDCl$_3$): δ 11.33 (br s, 1H), 10.00 (br s, 1H), 8.43 (s, 1H), 7.38 (d, 1H, J=2.0 Hz), 7.23 (d, 2H, J=8.0 Hz), 7.17 (d, 2H, J=8.0 Hz), 7.05 (d, 1H, J=2.5 Hz), 3.52 (s, 2H), 3.19 (s, 2H), 2.65 (q, 2H, J=7.5 Hz), 2.63 (br s, 4H), 2.53 (br s, 4H), 1.44 (s, 9H), 1.30 (s, 9H), 1.24 (t, 3H, J=7.5 Hz). $^{13}$C-NMR (125 MHz, CDCl$_3$): δ 165.7, 155.6, 152.6, 143.2, 140.7, 136.9, 134.9, 129.1, 127.8, 126.9, 125.6, 116.3, 62.6, 61.0, 53.7, 53.0, 35.1, 34.1, 31.5, 29.4, 28.5, 15.6. HRMS (ESI): 493.3550 (M+1); calcd. for C$_{30}$H$_{45}$N$_4$O$_2$: 493.3543.

Example 3. Biological Evaluation of 837 Analogues of PAC-1

Materials.

All reagents were obtained from Fisher unless otherwise indicated. All buffers were made with MilliQ purified water. Ac-DEVD-pNA was synthesized as previously described.[5] Luria broth (LB) was obtained from EMD. Doxorubicin was obtained from Sigma. Caspase Activity Buffer contains 50 mM HEPES, 300 mM NaCl, 1.5 mM TCEP, 0.01% TritonX-100 and is Chelex® treated. Ni NTA Binding Buffer contains 50 mM Tris (pH 8.0), 300 mM NaCl, and 10 mM imidazole. Ni NTA Wash Buffer contains 50 mM Tris (pH 8.0), 300 mM NaCl, and 50 mM imidazole. Ni NTA Elution Buffer contains 50 mM Tris (pH 8.0), 300 mM NaCl, and 500 mM

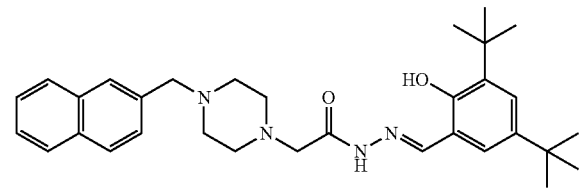 [SMILES: CC(C)(C)c1cc(/C=N/NC(=O)CN2CCN(Cc3ccc4ccccc4c3)CC2)c(O)c(C(C)(C)C)c1]

imidazole. Annexin V Binding Buffer contains 10 mM HEPES pH 7.4, 140 mM NaCl, 2.5 mM CaCl2, 0.1% BSA. The C-terminal 6×His-tagged procaspase-3 proteins were expressed as described below.

Cell Culture.

U-937 cells were obtained from the American Type Culture Collection and maintained at low passage number. Cultures were maintained in RPMI 1640 supplemented with 10% fetal bovine serum and 1% penicillin-streptomycin and grown at 37° C. and 5% $CO_2$.

Cell Death Assay for Initial Screen.

Compound (2 µL of a 10 mM DMSO solution) was added in singlet by direct addition to a well containing 998 µL U-937 cells (1×10$^6$) in RPMI 1640 media (10% FBS) at a final compound concentration of 20 µM. After incubation at 37° C. for 24 h, the cells were transferred to flow cytometry tubes, washed, and resuspended in Annexin V binding buffer. The cells were double stained with FITC-Annexin V and propidium iodide and a cell population of at least 10,000 events was collected by the LSR II flow cytometer. Percent viable cells (Annexin V—negative, propidium iodide—negative) were determined using FCS Express software.

72 Hour $IC_{50}$ Cell Death Assay.

U-937 human lymphoma cells were plated into the wells of 96 well plate at a density of 15,000 cells per well in 99 µL of RPMI 1640 growth media with 10% FBS and 1% pen-strep. To each well was added 1 µL of compound stock solutions in DMSO at varying concentrations such that the cells were treated with concentrations between 0 µM and 100 µM compound. Each concentration was tested in quintuplicate per plate. In each plate 5 wells received 20 µM doxorubicin as a positive death control and 5 wells received 1 of DMSO as a negative control. The plates were then incubated at 37° C. and 5% CO2 for 72 hours.

After the 72 hour incubation period, the plates were analyzed using a Sulforhodamine B assay (Vichai and Kirtikara, *Nat Protoc* 2006, 1, 1112-1116). Specifically, to each well of the plate 25 µL of a 50% (w/v) solution of trichloroacetic acid in $H_2O$ was added and the plates were incubated for 4 hours at 4° C. The plates were then washed gently with water five times. The plates were allowed to air dry after which 100 µL of a 0.057% (w/v) Sulforhodamine B in a 1% (v/v) acetic acid solution was added to each well for 30 minutes at room temperature. The plates were gently washed 5 times with 1% (v/v) acetic acid and air dried. 200 µL of 10 mM Tris base (pH 10.4) was added to each well and the plates were placed on an orbital shaker for thirty minutes. The level of SRB was quantified fluorometrically at excitation and emission wavelengths 488 and 585 nm, respectively, on a Molecular Devices plate reader and the percent cell death calculated and normalized to the positive control (100% cell death) and the negative control (0% cell death). The percent cell death was averaged for each compound concentration and plotted as a function of compound concentration. The data were fit to a logistical dose response curve using Table curve 2D and the $IC_{50}$ value was calculated. The experiment was repeated three times and the average of the calculated $IC_{50}$ values was reported. The standard error of the mean (SEM) was determined and reported for the triplicate experiments.

Induction of Apoptosis by Hit Compounds.

U-937 Cells (1 mL of 6×10$^5$ cells/mL) were treated with 10 µL of 750 µM DMSO solutions of the compounds to achieve a final concentration of 7.5 µM. The cells were incubated at 37° C. for 24 hours. The cells were harvested via centrifugation (200 g for 5 minutes), washed with PBS (2 mL), and resuspended in 450 µL Annexin V Binding Buffer. To each sample was added 3.5 µL of FITC conjugated Annexin V stain (Southern Biotech) and 3.5 µL of propidium iodide (Sigma) to a final concentration of 50 µg/mL. Cell populations were analyzed on a Benton Dickinson LSR II cell flow cytometer.

Recombinant Expression and Purification of Procaspase-3.

Techniques adapted from Hergenrother and coworkers (Putt et al., *Nat Chem Biol* 2006, 2, 543-550). A 20 mL volume of an overnight culture of *Rosetta E. coli* containing the procaspase-3 (wild-type) expression plasmid was seeded into 2 L of LB media containing ampicillin. The culture was grown to an OD600=1.0, at which point protein expression was induced via addition of IPTG (to 1 mM); the culture was allowed to grow for 30 additional minutes. Cells were then harvested (10 minute spins at 10,000×g and re-suspended in NTA binding buffer (300 mM NaCl, 50 mM Tris, 10 mM imidazole, pH 8.0). The cells were lysed on ice via sonication. The cell lysate was then spun at 35,000×g for 35 min. The supernatant was decanted and 1 mL of nickel-NTA resin was added. The cell lysate was incubated for 45 minutes at 4° C. The resin was loaded on a column, washed with 10 mL NTA binding buffer followed by 10 mL NTA wash buffer (300 mM NaCl, 50 mM Tris, 50 mM imidazole, pH 8.0). The proteins were eluted in 0.5 mL fractions with 10 mL of NTA elution buffer (300 mM NaCl, 50 mM Tris, 500 mM imidazole, pH 8.0). Fractions containing protein were pooled and further purified to remove any contaminating zinc by applying the protein to a PD-10 column (GE Healthcare) charged with Caspase Activity Buffer that had been treated with Chelex® resin. The resulting concentration was determined using the Edelhoch method and the molar absorptivity of procaspase-3 of 26150 $M^{-1}$ $cm^{-1}$. Protein stocks were flash-frozen in liquid nitrogen and stored at −80° C.

Procaspase-3 Activity Assay.

In a 384-well plate recombinantly expressed, zinc-free procaspase-3 (wild type, at 1 µM) in Caspase Activity Buffer (50 mM HEPES, 300 mM NaCl, 1.5 mM TCEP, 0.01% TritonX-100) was incubated at 37° C. in the presence of 3.5 µM $ZnSO_4$ and the basal activity was assessed via the addition of Ac-DEVD-pNA (final concentration in well of 200 µM). The absorbance at 405 nm was monitored with a SpectraMax plate reader (Molecular Devices). After the basal activity was determined, DMSO, PAC-1 and analogues were added to each sample to a final concentration of 25 µM. Activity of each treatment was assessed at 5, 20, 40 and 60 minutes via 5-minute kinetic reads. The slope of each data set was used to determine the activity of the protein. Activity was normalized to a percent activity at each time point using a zinc-free sample and a zinc-inhibited sample treated with DMSO.

Figure 5:
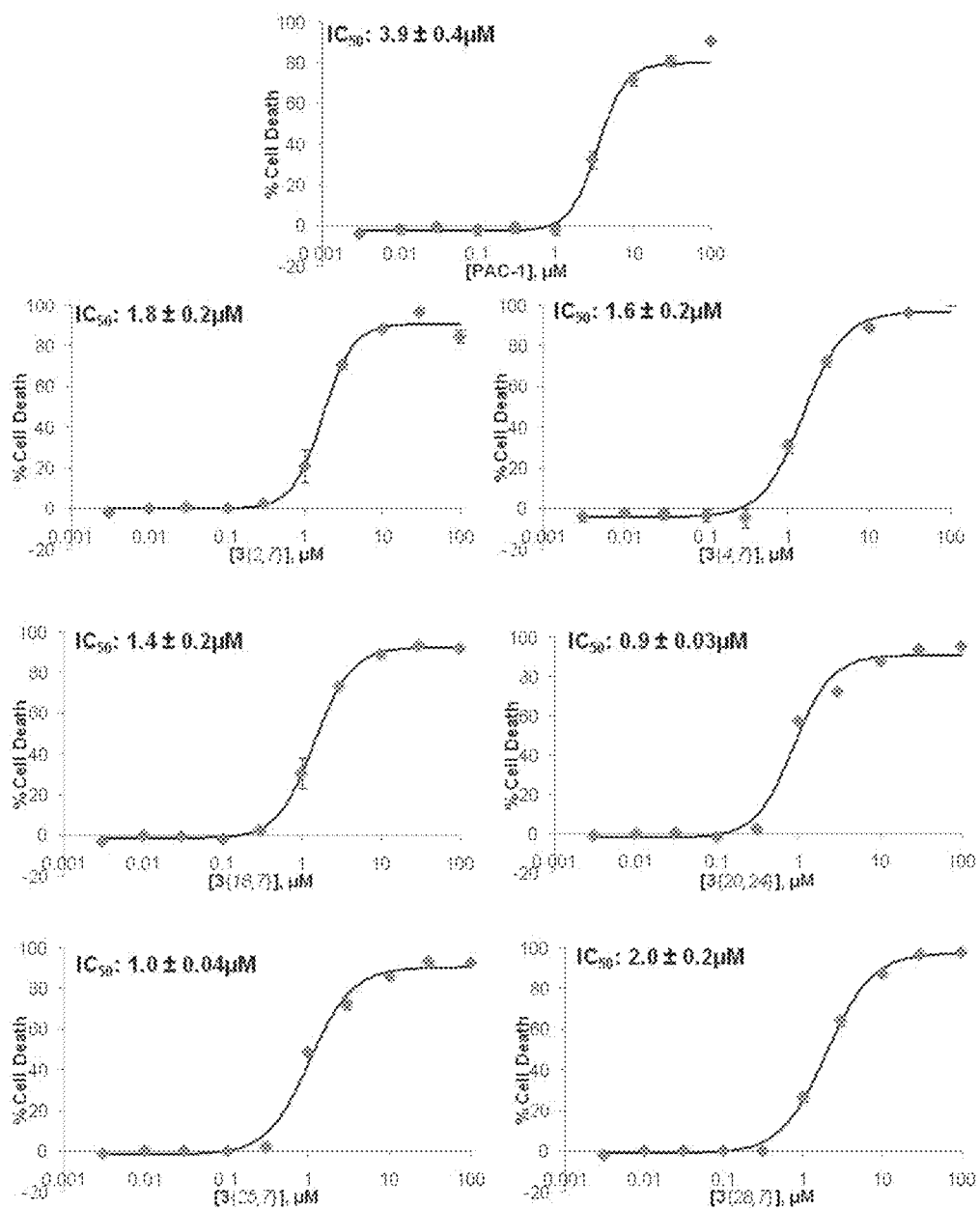
FIG. 5. Analysis of the cytotoxicity of PAC-1 and derivatives. Each graph shows the average of three dose response curves used to generate the IC$_{50}$ value for each derivative. The results of these experiments are summarized above in Table 1.

Analysis of the cytotoxicity of PAC-1 and derivatives is shown in FIG. 5. Each graph shows the average of three dose response curves used to generate the $IC_{50}$ value for each derivative. The results of these experiments are summarized above in Table 1.

Example 4. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method of treating cancer comprising exposing the cancer to an effective amount of a procaspase activator compound that activates procaspase-3 upon contacting procaspase-3, wherein the procaspase activator compound is a compound Formula I:

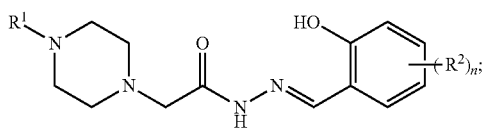

wherein
R¹ is a substituted (aryl)methylene;
n is 1, 2, 3, or 4; and
each R² is alkyl; or two R² groups form an ortho-fused benzo group;
wherein the (aryl)methylene substitution is methoxy, phenoxy, trifluoromethoxy, benzyloxy, or a combination thereof;
or a pharmaceutically acceptable salt or solvate thereof;
thereby killing the cancer cell or inhibiting the cancer cell from proliferating;
wherein the cancer is lymphoma.

2. The method of claim 1 wherein each R² is t-butyl.

3. The method of claim 1 wherein R¹ is:

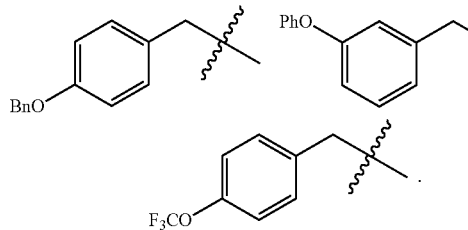

4. The method of claim 1 wherein the compound of Formula I is:

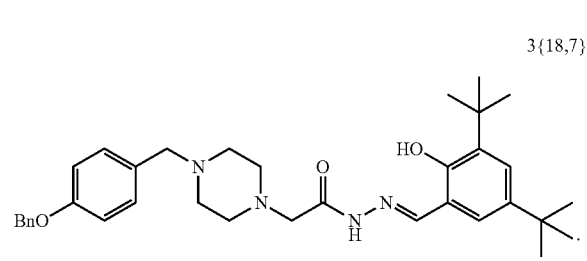 [SMILES: CC(C)(C)c1cc(/C=N/NC(=O)CN2CCN(Cc3ccc(OCc4ccccc4)cc3)CC2)c(O)c(C(C)(C)C)c1]

5. The method of claim 1 wherein the compound of Formula I is in the form of a composition comprising a pharmaceutically acceptable diluent, excipient, or carrier.

6. The method of claim 5 wherein the composition comprises a compound of Formula I at a concentration of about 10 nM to about 100 μM.

7. The method of claim 5 wherein the composition comprises a compound of Formula I at a concentration of about 200 nM to about 5 μM.

8. The method of claim 1 wherein the lethality of the compound of Formula I is selective for the cancer cell over non-cancerous cells.

9. A method of inducing apoptosis in a cancer cell comprising administering to a cancer cell an effective apoptotic amount of a compound of Formula I:

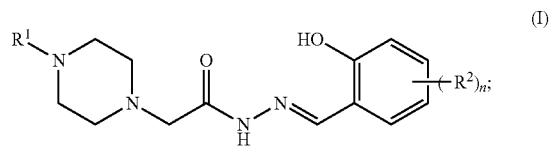

wherein
R¹ is a substituted (aryl)methylene;
n is 1, 2, 3, or 4; and
each R² is alkyl; or two R² groups form an ortho-fused benzo group;
wherein the (aryl)methylene substitution is methoxy, phenoxy, trifluoromethoxy, benzyloxy, or a combination thereof;
or a pharmaceutically acceptable salt or solvate thereof;
thereby killing the cancer cell or inhibiting the cancer cell from proliferating;
wherein the cancer cell is a lymphoma cell.

10. The method of claim 9 wherein each R² is t-butyl.

11. The method of claim 9 wherein R¹ is:

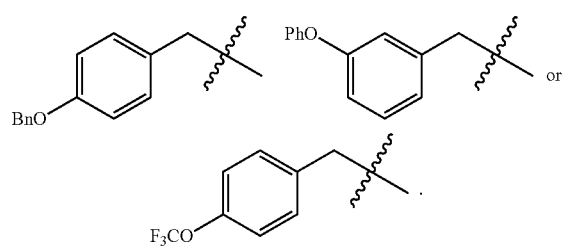

12. The method of claim 9 wherein the compound of Formula I is:

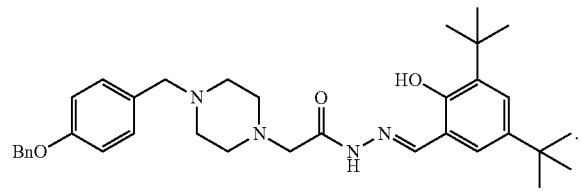

13. The method of claim 9 wherein the compound of Formula I is in the form of a composition comprising a pharmaceutically acceptable diluent, excipient, or carrier.

14. The method of claim 13 wherein the composition comprises a compound of Formula I at a concentration of about 10 nM to about 100 μM.

15. The method of claim 13 wherein the composition comprises a compound of Formula I at a concentration of about 200 nM to about 5 μM.

16. A method of treating lymphoma comprising exposing lymphoma cells to an effective amount of a procaspase activator compound that activates procaspase-3 upon contacting procaspase-3 and selectively induces apoptosis of the lymphoma cells, wherein the procaspase activator compound is:

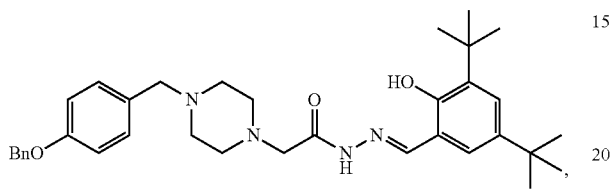

3{18, 7} or a pharmaceutically acceptable salt thereof;
thereby killing lymphoma cells or inhibiting lymphoma cells from proliferating.

* * * * *